United States Patent
Allen et al.

(10) Patent No.: US 9,822,118 B2
(45) Date of Patent: Nov. 21, 2017

(54) BICYCLIC HETEROARYL UREA, THIOUREA, GUANIDINE AND CYANOGUANIDINE COMPOUNDS AS TRKA KINASE INHIBITORS

(71) Applicant: Array BioPharma Inc., Boudler, CO (US)

(72) Inventors: Shelley Allen, Boulder, CO (US); Barbara J. Brandhuber, Boulder, CO (US); Kevin Ronald Condroski, San Diego, CA (US); Lily Huang, Austin, TX (US); Timothy Kercher, San Diego, CA (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/442,503

(22) PCT Filed: Nov. 13, 2013

(86) PCT No.: PCT/US2013/069886
§ 371 (c)(1),
(2) Date: May 13, 2015

(87) PCT Pub. No.: WO2014/078408
PCT Pub. Date: May 22, 2014

(65) Prior Publication Data
US 2016/0355517 A1    Dec. 8, 2016

Related U.S. Application Data

(60) Provisional application No. 61/725,945, filed on Nov. 13, 2012.

(51) Int. Cl.
| | | |
|---|---|---|
| C07D 487/04 | (2006.01) |
| C07D 231/56 | (2006.01) |
| C07D 471/04 | (2006.01) |
| C07D 491/048 | (2006.01) |
| C07D 495/04 | (2006.01) |
| C07D 403/12 | (2006.01) |
| C07D 519/00 | (2006.01) |

(52) U.S. Cl.
CPC ......... *C07D 487/04* (2013.01); *C07D 231/56* (2013.01); *C07D 403/12* (2013.01); *C07D 471/04* (2013.01); *C07D 491/048* (2013.01); *C07D 495/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 5,849,779 A | 12/1998 | Hirota et al. |
| 5,998,424 A | 12/1999 | Galemmo, Jr. et al. |
| 6,197,798 B1 | 3/2001 | Fink et al. |
| 6,410,533 B1 | 6/2002 | Hirth et al. |
| 7,223,782 B2 | 5/2007 | Atkinson et al. |
| 7,625,915 B2 | 12/2009 | Dumas et al. |
| 8,592,454 B2 | 11/2013 | Shirai et al. |
| 9,163,017 B2 | 10/2015 | Degoey |

FOREIGN PATENT DOCUMENTS

| | | |
|---|---|---|
| EP | 0761658 A1 | 12/1997 |
| EP | 1043995 B1 | 11/2006 |
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |

(Continued)

OTHER PUBLICATIONS

Felder "The generation of purinome-targeted libraries as a means to diversify ATP-mimetic chemical classes for lead finding" Molecular Diversity 2012, 16:27-51.*
Michelotti et. al. "Two classes of p38a MAP kinase inhibitors having a common diphenylether core but exhibiting divergent binding modes" 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4-—amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*

(Continued)

*Primary Examiner* — David K O'Dell
(74) *Attorney, Agent, or Firm* — Viksnins Harris Padys Malen LLP; Sarah S. Mastous

(57) ABSTRACT

Compounds of Formula I or stereoisomers, tautomers, or pharmaceutically acceptable salts, solvates or prodrugs thereof, wherein Ring A, Ring C and X are as defined herein, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

(I)

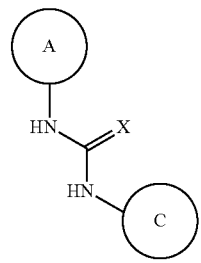

6 Claims, No Drawings

(56) References Cited

FOREIGN PATENT DOCUMENTS

| | | | |
|---|---|---|---|
| WO | 9923091 A1 | 5/1999 | |
| WO | 9932110 A1 | 7/1999 | |
| WO | 0039116 A1 | 7/2000 | |
| WO | 0043384 A1 | 7/2000 | |
| WO | 0112188 A1 | 2/2001 | |
| WO | 0202525 A2 | 1/2002 | |
| WO | 02088101 A2 | 11/2002 | |
| WO | 02090326 A1 | 11/2002 | |
| WO | 03037274 A2 | 5/2003 | |
| WO | 03045920 A1 | 6/2003 | |
| WO | 03051275 A2 | 6/2003 | |
| WO | 2004005262 A2 | 1/2004 | |
| WO | 2004032870 A2 | 4/2004 | |
| WO | 2004060305 A2 | 7/2004 | |
| WO | 2004060306 A2 | 7/2004 | |
| WO | 2004061084 A2 | 7/2004 | |
| WO | 2004111009 A1 | 12/2004 | |
| WO | 2005024755 A2 | 3/2005 | |
| WO | 2005048948 A2 | 6/2005 | |
| WO | 2005110994 A2 | 11/2005 | |
| WO | 2006014290 A2 | 2/2006 | |
| WO | 2006068591 A1 | 6/2006 | |
| WO | 2006070198 A1 | 7/2006 | |
| WO | 2006071940 A2 | 7/2006 | |
| WO | 2006081034 A2 | 8/2006 | |
| WO | 2006123257 A2 | 11/2006 | |
| WO | 2007008917 A2 | 1/2007 | |
| WO | 2007059202 A2 | 5/2007 | |
| WO | 2007061882 A2 | 5/2007 | |
| WO | 2007064872 A2 | 6/2007 | |
| WO | 2008016811 A2 | 2/2008 | |
| WO | 2008021859 A1 | 2/2008 | |
| WO | 2008033999 A2 | 3/2008 | |
| WO | 2008034008 A2 | 3/2008 | |
| WO | 2008046003 A2 | 4/2008 | |
| WO | 2008131276 A1 | 10/2008 | |
| WO | 2008150899 A1 | 12/2008 | |
| WO | 2009140128 A2 | 11/2009 | |
| WO | 2010032856 A1 | 3/2010 | |
| WO | 2010033941 A1 | 3/2010 | |
| WO | 2010040663 A1 | 4/2010 | |
| WO | 2010048314 A1 | 4/2010 | |
| WO | 2010059719 A2 | 5/2010 | |
| WO | 2010075376 A2 | 7/2010 | |
| WO | 2010077680 A2 | 7/2010 | |
| WO | 2010104488 A1 | 9/2010 | |
| WO | 2010125799 A1 | 11/2010 | |
| WO | 2011006074 A1 | 1/2011 | |
| WO | 2011032291 A1 | 3/2011 | |
| WO | 2011146336 A1 | 11/2011 | |
| WO | 2012158413 A2 | 11/2012 | |
| WO | 2013063214 A1 | 5/2013 | |
| WO | 2013096226 A1 | 6/2013 | |
| WO | 2013176970 A1 | 11/2013 | |
| WO | 2014052563 A1 | 4/2014 | |
| WO | 2014052566 A1 | 4/2014 | |
| WO | 2014078322 A1 | 5/2014 | |
| WO | 2014078323 A1 | 5/2014 | |
| WO | 2014078325 A1 | 5/2014 | |
| WO | 2014078328 A1 | 5/2014 | |
| WO | 2014078331 A1 | 5/2014 | |
| WO | 2014078372 A1 | 5/2014 | |
| WO | 2014078378 A1 | 5/2014 | |
| WO | 2014078408 A1 | 5/2014 | |
| WO | 2014078417 A1 | 5/2014 | |
| WO | 2014078454 A1 | 5/2014 | |
| WO | 2015039333 A1 | 3/2015 | |
| WO | 2015042085 A2 | 3/2015 | |

OTHER PUBLICATIONS

Gingrich "Synthesis, Modeling, and In Vitro Activity of (3'S)—epi-K-252a Analogues. Elucidating the Stereochemical Requirements of the 3'-Sugar Alcohol on trkA Tyrosine Kinase Activity" J. Med. Chem. 2005, 48, 3776-3783.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Patent Cooperation Treaty, International Searching Authority, Search Report and Written Opinion for PCT/US2013/069886, May 28, 2015, 7 Pages.
Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site Inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti—and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K, et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.
McCarthy, C. and Walker, E., Expert Opin. Ther. Patents (2014) 24(7):731-744.
Mcmahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.

(56) References Cited

OTHER PUBLICATIONS

Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et al., Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.
Tsuzuki, Y., et al., Tetrahedron Asymmetry 12 (2001), 2989-2997.
Wadhwa, S., et al., Journal of Biosciences, 2003, 28(2), 181-188.
Wang, T., et al., Expert Opinion in Therapeutic Patents (2009) 19(3)305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.

\* cited by examiner

BICYCLIC HETEROARYL UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069886, filed Nov. 13, 2013, which claims priority to United States Provisional Application Ser. No. 61/725,945, filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to bicyclic heteroaryl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) *BJU International*, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases.

Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

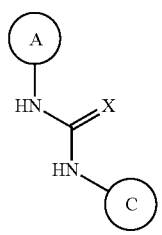

I or stereoisomers, tautomers, or pharmaceutically acceptable salts, solvates or prodrugs thereof, wherein Ring A, Ring C and X are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA.

Compounds of the invention such as those shown in Table A below, were found to be at least 1000 fold more selective for TrkA versus p38α.

One embodiment provides a compound of Formula I:

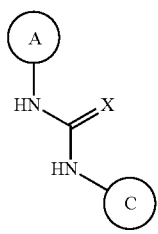

I or stereoisomers, tautomers, or pharmaceutically acceptable salts, solvates or prodrugs thereof, wherein:

X is O, S, NH or —N—CN;
Ring A is formula A-1, A-2, A-3 or A-4

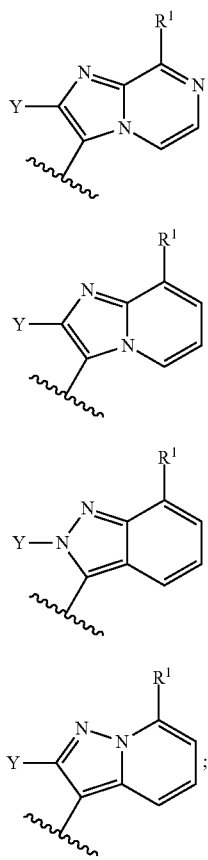

$R^1$ is H, halogen, (1-3C)alkyl [optionally substituted with 1-5 fluoros], (1-3C)alkoxy [optionally substituted with 1-5 fluoros], or (3-5C)cycloalkyl;

Y is $Ar^1$ or $hetAr^1$;

$Ar^1$ is phenyl optionally substituted with one or more substituents independently selected from halogen, (1-3C) alkyl [optionally substituted with 1-5 fluoros], and (1-3C) alkoxy [optionally substituted with 1-5 fluoros];

$hetAr^1$ is pyridyl optionally substituted with one or more substituents independently selected from halogen, (1-3C) alkyl [optionally substituted with 1-5 fluoros], and (1-3C) alkoxy [optionally substituted with 1-5 fluoros];

Ring C is formula C-1 or C-2

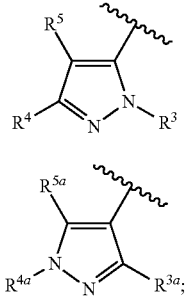

$R^3$ is (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more substituents independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more substituents independently selected from (1-6C)alkyl and halogen;

$R^4$ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C) alkoxy, trifluoro(1-6C)alkoxy, tetrafluoro(2-6C)alkoxy, pentafluoro(2-6C)alkoxy, cyano(1-6C)alkoxy, hydroxy(1-6C) alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2$(O)CH$_2$—, (1-4C alkoxycarbonyl)(1-6C) alkoxy, hydroxycarbonyl(1-6C)alkoxy, aminocarbonyl(1-6C)alkoxy, $hetCyc^2$C(=O)(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, $hetCyc^2$C(=O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, $hetCyc^3$, halogen, CN, trifluoromethylsulfonyl, N-(1-3C alkyl)oxadiazolonyl, or $hetAr^5$;

$hetCyc^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

$hetCyc^3$ is a 4-7 membered heterocycle having 1-2 ring heteroatoms independently selected from N and O and optionally substituted with one or more substituents independently selected from F, CN, (1-6C)alkyl, trifluoro(1-6C)

alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar$^a$ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

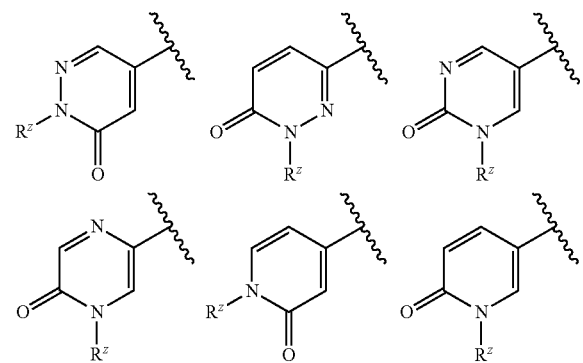

where R$^z$ is (3-4C)cycloalkyl or (1-3C)alkyl (optionally substituted with 1-3 fluoros), wherein each of said hetAr⁵ groups is optionally further substituted with one or more substituents independently selected from F and (1-3C)alkyl optionally substituted with 1-3 fluoros;

Ar⁴ is phenyl optionally substituted with one or more substituents independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more substituents independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R$^{3a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen;

R$^{4a}$ is hydrogen, (1-6C)alkyl, trifluoro(1-6C)alkyl, phenyl [optionally substituted with one or more substituents independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—] or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂-(3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R$^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C)alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where R is (1-4C)alkyl, (1-3C)alkyl, (1-6C)alkyl, or (2-6C)alkyl, respectively, as defined above. Examples include methoxy, ethoxy, and the like.

"(1-6C)Acyl" means a RC(=O)— radical where R is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C)alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" means a (1-6C)—O—C(=O)— group.

"Amino" means a —NRR' group where R and R' are independently selected from hydrogen or (1-3C)alkyl as defined herein. Examples include $H_2N-$, $CH_3NH-$, $(CH_3)_2 N$, and the like. "Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen and (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen and (1-3C)alkyl as defined herein.

"Aminocarbonyl" means a RRNCO— radical where R and R' are independently hydrogen or (1-6C)alkyl as defined herein. Examples include $H_2NCO-$, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"(1-3C)Alkylamido(1-6C)alkoxy" means a (1-6C)alkoxy as defined herein, wherein one of the carbon atoms is substituted with one alkylamido group, i.e., substituted with a (1-3C)C(=O)NH— group.

"(1-3C)Alkylsulfonamido" means a (1-3C) alkylSO$_2$NH— radical where (1-3C)alkyl is as defined herein "(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"(1-3C)Alkylsulfonyl" means a —SO$_2$R radical where R is (1-3C)alkyl as defined above, e.g., methylsulfonyl, and the like.

"(1-3C Alkylsulfonyl)(1-6C)alkoxy" means a (1-6C) alkoxy group as defined herein, wherein one of the carbon atoms is substituted with a (1-3C)alkylsulfonyl group.

"Hydroxycarbonyl" means HOC(=O)—.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" and "(3-5C)cycloalkyl mean a cyclic saturated monovalent hydrocarbon radical of three to six carbon atoms, or three to five carbon atoms, respectively, e.g., cyclopropyl, cyclobutyl, cyclopentyl, or cyclohexyl.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring-system having one or more ring heteroatoms as recited for the specific heteroaryl group, wherein the heteroaryl is optionally substituted with substituents as defined for that particular heteroaryl group.

"hetCyc$^2$C(=O)(1-6C)alkoxy" means a (1-6C)alkoxy as defined herein, wherein one of the carbon atoms is substituted with a hetCyc$^2$C(=O) group, wherein hetCyc$^2$ is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C) alkyl group as defined herein, wherein one of the carbon atoms is substituted with a hydroxy group.

"Hydroxytrifluoro(1-6C)alkoxy" means a trifluoro(1-6C) alkoxy group as defined herein, wherein one of the carbon atoms is substituted with a hydroxy group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido (H$_2$NSO$_2$NH—) group.

It should be noted that compounds of the invention may contain groups that may exist in tautomeric forms, such as heteroatom substituted heteroaryl or heterocyclic groups and the like, which are illustrated in the following general and specific examples:

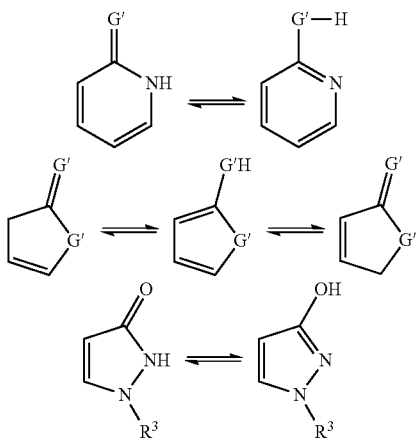

where G'=O, S, or NR, and though one form is named, described, displayed and/or claimed herein, all the tautomeric forms are intended to be inherently included in such name, description, display and/or claim.

In one embodiment of Formula I, X is O.
In one embodiment, X is S.
In one embodiment, X is —NH.
In one embodiment, X is —N—CN.
In one embodiment of Formula I, R$^1$ is H.
In one embodiment of Formula I, R$^1$ is halogen. In one embodiment, R$^1$ is F, Cl or Br.
In one embodiment of Formula I, R$^1$ is (1-3C)alkyl optionally substituted with 1-5 fluoros. In one embodiment, R$^1$ is methyl, ethyl, isopropyl, or trifluoromethyl.
In one embodiment of Formula I, R$^1$ is (1-3C)alkoxy optionally substituted with 1-5 fluoros. In one embodiment, R$^1$ is methoxy, ethoxy or trifluoromethoxy.
In one embodiment of Formula I, R$^1$ is (3-5C)cycloalkyl. In one embodiment of Formula I, R$^1$ is cyclopropyl.
In one embodiment of Formula I, R$^1$ is selected from H, halogen and (1-3C)alkyl [optionally substituted with 1-5 fluoros].
In one embodiment of Formula I, Y is Ar$^1$, where Ar$^1$ is phenyl optionally substituted with one or more substituents independently selected from halogen, (1-3C)alkyl [optionally substituted with 1-5 fluoros], and (1-3C)alkoxy [optionally substituted with 1-5 fluoros].
In one embodiment of Formula I, Y is phenyl optionally substituted with one or more substituents independently selected from halogen and (1-3C)alkoxy [optionally substituted with 1-5 fluoros].
In one embodiment of Formula I, Y is phenyl optionally substituted with one or more substituents independently selected from fluoro and methoxy.

In one embodiment of Formula I, Y is hetAr$^1$, where hetAr$^1$ is pyridyl optionally substituted with one or more substituents independently selected from halogen, (1-3C)alkyl [optionally substituted with 1-5 fluoros], and (1-3C)alkoxy [optionally substituted with 1-5 fluoros].
In one embodiment of Formula I, Y is pyridyl optionally substituted with one or more substituents independently selected from halogen and (1-3C)alkoxy [optionally substituted with 1-5 fluoros].
In one embodiment of Formula I, Y is pyridyl optionally substituted with one or more substituents independently selected from fluoro and methoxy.
In one embodiment of Formula I, Y is selected from phenyl or pyridyl, each of which is optionally substituted with one or more substituents independently selected from halogen and (1-3C)alkoxy [optionally substituted with 1-5 fluoros].
In one embodiment of Formula I, Ring A is formula A-1 or A-2.
In one embodiment of Formula I, Ring A is formula A-1

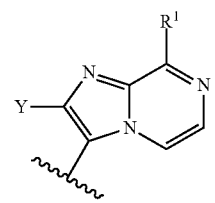

A-1 where R$^1$ and Y are as defined for Formula I.
In one embodiment of formula A-1, R$^1$ is H.
In one embodiment of formula A-1, R$^1$ is halogen. In one embodiment, R$^1$ is F, Cl or Br.
In one embodiment of formula A-1, R$^1$ is (1-3C)alkyl optionally substituted with 1-5 fluoros. In one embodiment, R$^1$ is methyl, ethyl, isopropyl, or trifluoromethyl.
In one embodiment of formula A-1, R$^1$ is (1-3C)alkoxy optionally substituted with 1-5 fluoros. In one embodiment, R$^1$ is methoxy, ethoxy or trifluoromethoxy.
In one embodiment of formula A-1, R$^1$ is (3-5C)cycloalkyl. In one embodiment of Formula I, R$^1$ is cyclopropyl.
In one embodiment of formula A-1, R$^1$ is selected from H, halogen and (1-3C)alkyl [optionally substituted with 1-5 fluoros].
In one embodiment of formula A-1, Y is Ar$^1$, where Ar$^1$ is phenyl optionally substituted with one or more substituents independently selected from halogen, (1-3C)alkyl [optionally substituted with 1-5 fluoros], and (1-3C)alkoxy [optionally substituted with 1-5 fluoros].
In one embodiment of formula A-1, Y is phenyl optionally substituted with one or more substituents independently selected from halogen and (1-3C)alkoxy [optionally substituted with 1-5 fluoros].
In one embodiment of formula A-1, Y is phenyl optionally substituted with one or more substituents independently selected from fluoro and methoxy.
In one embodiment of formula A-1, Y is hetAr$^1$, where hetAr$^1$ is pyridyl optionally substituted with one or more substituents independently selected from halogen, (1-3C)alkyl [optionally substituted with 1-5 fluoros], and (1-3C)alkoxy [optionally substituted with 1-5 fluoros].

In one embodiment of formula A-1, Y is pyridyl optionally substituted with one or more substituents independently selected from halogen and (1-3C)alkoxy [optionally substituted with 1-5 fluoros].

In one embodiment of formula A-1, Y is pyridyl optionally substituted with one or more substituents independently selected from fluoro and methoxy.

In one embodiment of formula A-1, Y is selected from phenyl or pyridyl, each of which is optionally substituted with one or more substituents independently selected from halogen and (1-3C)alkoxy [optionally substituted with 1-5 fluoros].

In one embodiment of formula A-1, R¹ is halogen or (1-3C)alkyl optionally substituted with 1-5 fluoros; and Y is phenyl or pyridyl optionally substituted with one or more substituents independently selected from halogen and (1-3C)alkoxy [optionally substituted with 1-5 fluoros].

In one embodiment, formula A-1 has the structure:

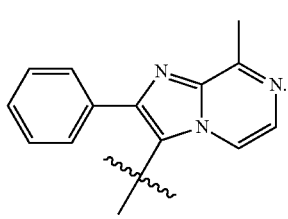 [SMILES: *c1c(-c2ccccc2)nc2c(C)nccn12]

In one embodiment of Formula I, Ring A is formula A-2

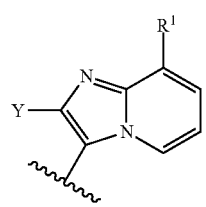

A-2 where R¹ and Y are as defined for Formula I.

In one embodiment of formula A-2, R¹ is H.

In one embodiment of formula A-2, R¹ is halogen. In one embodiment, R¹ is F, Cl or Br.

In one embodiment of formula A-2, R¹ is (1-3C)alkyl optionally substituted with 1-5 fluoros. In one embodiment, R¹ is methyl, ethyl, isopropyl, or trifluoromethyl.

In one embodiment of formula A-2, R¹ is (1-3C)alkoxy optionally substituted with 1-5 fluoros. In one embodiment, R¹ is methoxy, ethoxy or trifluoromethoxy.

In one embodiment of formula A-2, R¹ is (3-5C)cycloalkyl. In one embodiment of Formula I, R¹ is cyclopropyl.

In one embodiment of formula A-2, R¹ is selected from H, halogen and (1-3C)alkyl [optionally substituted with 1-5 fluoros].

In one embodiment of formula A-2, Y is Ar¹, where Ar¹ is phenyl optionally substituted with one or more substituents independently selected from halogen, (1-3C)alkyl [optionally substituted with 1-5 fluoros], and (1-3C)alkoxy [optionally substituted with 1-5 fluoros].

In one embodiment of formula A-2, Y is phenyl optionally substituted with one or more substituents independently selected from halogen and (1-3C)alkoxy [optionally substituted with 1-5 fluoros].

In one embodiment of formula A-2, Y is phenyl optionally substituted with one or more substituents independently selected from fluoro and methoxy.

In one embodiment of formula A-2, Y is hetAr¹, where hetAr¹ is pyridyl optionally substituted with one or more substituents independently selected from halogen, (1-3C)alkyl [optionally substituted with 1-5 fluoros], and (1-3C)alkoxy [optionally substituted with 1-5 fluoros].

In one embodiment of formula A-2, Y is pyridyl optionally substituted with one or more substituents independently selected from halogen and (1-3C)alkoxy [optionally substituted with 1-5 fluoros].

In one embodiment of formula A-2, Y is pyridyl optionally substituted with one or more substituents independently selected from fluoro and methoxy.

In one embodiment of formula A-2, Y is selected from phenyl or pyridyl, each of which is optionally substituted with one or more substituents independently selected from halogen and (1-3C)alkoxy [optionally substituted with 1-5 fluoros].

In one embodiment of formula A-2, R¹ is halogen or (1-3C)alkyl optionally substituted with 1-5 fluoros; and Y is phenyl or pyridyl optionally substituted with one or more substituents independently selected from halogen and (1-3C)alkoxy [optionally substituted with 1-5 fluoros].

In one embodiment, formula A-2 is selected from the structures:

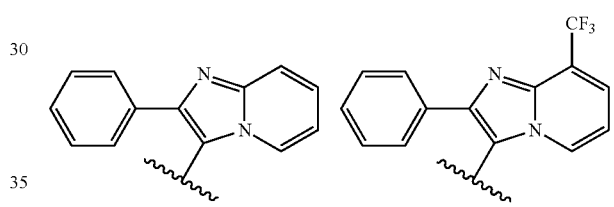

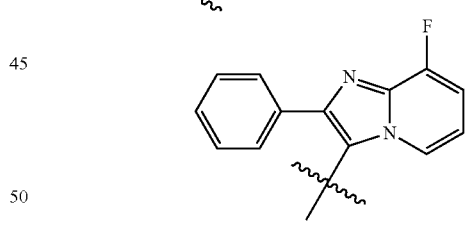

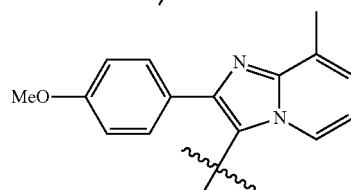

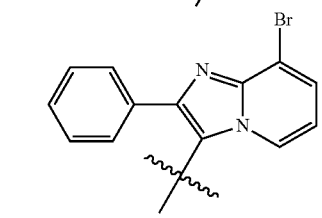

-continued

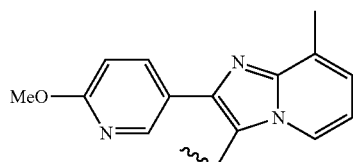

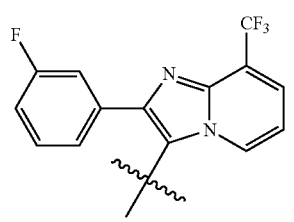

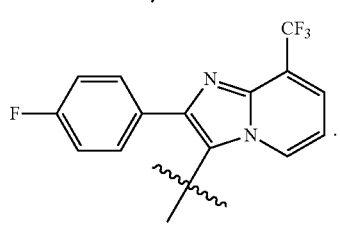

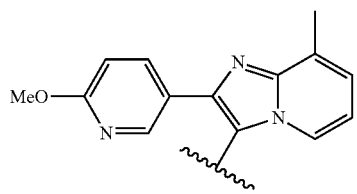

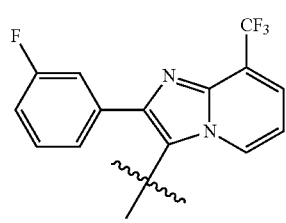

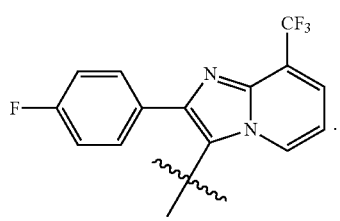

In one embodiment of Formula I, Ring A is formula A-3

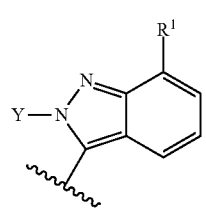

where $R^1$ and Y are as defined for Formula I.

In one embodiment of formula A-3, $R^1$ is H.

In one embodiment of formula A-3, $R^1$ is halogen. In one embodiment, $R^1$ is F, Cl or Br.

In one embodiment of formula A-3, $R^1$ is (1-3C)alkyl optionally substituted with 1-5 fluoros. In one embodiment, $R^1$ is methyl, ethyl, isopropyl, or trifluoromethyl.

In one embodiment of formula A-3, $R^1$ is (1-3C)alkoxy optionally substituted with 1-5 fluoros. In one embodiment, $R^1$ is methoxy, ethoxy or trifluoromethoxy.

In one embodiment of formula A-3, $R^1$ is (3-5C)cycloalkyl. In one embodiment of Formula I, $R^1$ is cyclopropyl.

In one embodiment of formula A-3, $R^1$ is selected from H, halogen and (1-3C)alkyl [optionally substituted with 1-5 fluoros].

In one embodiment of formula A-3, Y is $Ar^1$, where $Ar^1$ is phenyl optionally substituted with one or more substituents independently selected from halogen, (1-3C)alkyl [optionally substituted with 1-5 fluoros], and (1-3C)alkoxy [optionally substituted with 1-5 fluoros].

In one embodiment of formula A-3, Y is phenyl optionally substituted with one or more substituents independently selected from halogen and (1-3C)alkoxy [optionally substituted with 1-5 fluoros].

In one embodiment of formula A-3, Y is phenyl optionally substituted with one or more substituents independently selected from fluoro and methoxy.

In one embodiment of formula A-3, Y is $hetAr^1$, where $hetAr^1$ is pyridyl optionally substituted with one or more substituents independently selected from halogen, (1-3C) alkyl [optionally substituted with 1-5 fluoros], and (1-3C) alkoxy [optionally substituted with 1-5 fluoros].

In one embodiment of formula A-3, Y is pyridyl optionally substituted with one or more substituents independently selected from halogen and (1-3C)alkoxy [optionally substituted with 1-5 fluoros].

In one embodiment of formula A-3, Y is pyridyl optionally substituted with one or more substituents independently selected from fluoro and methoxy.

In one embodiment of Formula I, Y is selected from phenyl or pyridyl, each of which is optionally substituted with one or more substituents independently selected from halogen and (1-3C)alkoxy [optionally substituted with 1-5 fluoros].

In one embodiment of formula A-3, $R^1$ is hydrogen, halogen or (1-3C)alkyl optionally substituted with 1-5 fluoros; and Y is phenyl or pyridyl optionally substituted with one or more substituents independently selected from halogen and (1-3C)alkoxy [optionally substituted with 1-5 fluoros]. In one embodiment, formula A-3 has the structure:

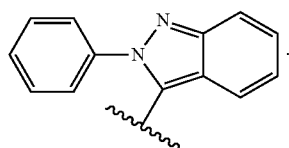 [SMILES: *c1c2ccccc2nn1-c1ccccc1]

In one embodiment of Formula I, Ring A is formula A-4

A-4 where $R^1$ and Y are as defined for Formula I.

In one embodiment of formula A-4, $R^1$ is H.

In one embodiment of formula A-4, $R^1$ is halogen. In one embodiment, $R^1$ is F, Cl or Br.

In one embodiment of formula A-4, $R^1$ is (1-3C)alkyl optionally substituted with 1-5 fluoros. In one embodiment, $R^1$ is methyl, ethyl, isopropyl, or trifluoromethyl.

In one embodiment of formula A-4, $R^1$ is (1-3C)alkoxy optionally substituted with 1-5 fluoros. In one embodiment, $R^1$ is methoxy, ethoxy or trifluoromethoxy.

In one embodiment of formula A-4, $R^1$ is (3-5C)cycloalkyl. In one embodiment of Formula I, $R^1$ is cyclopropyl.

In one embodiment of Formula I, $R^1$ is selected from H, halogen and (1-3C)alkyl [optionally substituted with 1-5 fluoros].

In one embodiment of formula A-4, Y is $Ar^1$, where $Ar^1$ is phenyl optionally substituted with one or more substituents independently selected from halogen, (1-3C)alkyl [optionally substituted with 1-5 fluoros], and (1-3C)alkoxy [optionally substituted with 1-5 fluoros].

In one embodiment of formula A-4, Y is phenyl optionally substituted with one or more substituents independently selected from halogen and (1-3C)alkoxy [optionally substituted with 1-5 fluoros].

In one embodiment of formula A-4, Y is phenyl optionally substituted with one or more substituents independently selected from fluoro and methoxy.

In one embodiment of formula A-4, Y is $hetAr^1$, where $hetAr^1$ is pyridyl optionally substituted with one or more substituents independently selected from halogen, (1-3C) alkyl [optionally substituted with 1-5 fluoros], and (1-3C) alkoxy [optionally substituted with 1-5 fluoros].

In one embodiment of formula A-4, Y is pyridyl optionally substituted with one or more substituents independently selected from halogen and (1-3C)alkoxy [optionally substituted with 1-5 fluoros].

In one embodiment of formula A-4, Y is pyridyl optionally substituted with one or more substituents independently selected from fluoro and methoxy.

In one embodiment of formula A-4, Y is selected from phenyl or pyridyl, each of which is optionally substituted with one or more substituents independently selected from halogen and (1-3C)alkoxy [optionally substituted with 1-5 fluoros].

In one embodiment of formula A-4, $R^1$ is halogen or (1-3C)alkyl optionally substituted with 1-5 fluoros; and Y is phenyl or pyridyl optionally substituted with one or more substituents independently selected from halogen and (1-3C)alkoxy [optionally substituted with 1-5 fluoros].

Reference will now be made to Ring C.

In one embodiment, Ring C is formula C-1:

C-1 where $R^3$, $R^4$ and $R^5$ are as defined for Formula I.

In one embodiment, $R^3$ is (1-6C)alkyl. In one embodiment, $R^3$ is methyl or ethyl.

In one embodiment, $R^3$ is hydroxy(1-6C)alkyl. An example of $R^3$ is 2-hydroxyethyl.

In one embodiment, $R^3$ is $Ar^2$, where $Ar^2$ is phenyl optionally substituted with one or more substituents independently selected from halogen and (1-6C)alkyl.

In one embodiment, $R^3$ when represented by $Ar^2$ is phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, $R^3$ when represented by $Ar^2$ is phenyl, 2-fluorophenyl, 3-fluorophenyl, 4-fluorophenyl, 2-methylphenyl, 3-methylphenyl or 4-methylphenyl. In one embodiment, $R^3$ is phenyl.

In one embodiment, $R^3$ is $hetCyc^1$, where $hetCyc^1$ is a 5-6-membered saturated or partially unsaturated heterocyclic ring having 1-2 ring heteroatoms independently selected from N and O. In one embodiment, $R^3$ is a pyrrolidinyl, tetrahydrofuranyl, imidazolidinyl, piperidinyl, piperazinyl, tetrahydropyranyl, or morpholinyl ring. In one embodiment, $R^3$ is tetrahydro-2H-pyran-4-yl.

In one embodiment, $R^3$ is (3-7C)cycloalkyl. In one embodiment $R^3$ is cyclohexyl.

In one embodiment, $R^3$ is $hetAr^2$, where $hetAr^2$ is 5-6 membered heteroaryl ring having 1-3 ring heteroatoms independently selected from N, O and S and optionally substituted with one or more substituents independently selected from (1-6C)alkyl and halogen. In one embodiment, $R^3$ is thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, $R^3$ is pyrazolyl, pyridyl or pyridazinyl optionally substituted with one or more substituents independently selected from (1-6C)alkyl and halogen. In one embodiment, $R^3$ is pyrazolyl, pyridyl or pyridazinyl optionally substituted with (1-6C)alkyl or halogen. In one embodiment, $R^3$ when represented by $hetAr^2$ is 1-methyl-1H-pyrazol-4-yl, pyrid-2-yl, pyrid-3-yl, pyrid-4-yl, pyridazinyl or 3-chloropyrid-5-yl.

In one embodiment, $R^3$ is selected from $Ar^2$ and $hetAr^2$.

In one embodiment, $R^3$ is $Ar^2$. In one embodiment, $R^3$ is phenyl.

In one embodiment, $R^4$ is OH.

In one embodiment, $R^4$ is (1-6C)alkyl. In one embodiment, $R^4$ is methyl, ethyl, isopropyl or tert-butyl.

In one embodiment, $R^4$ is monofluoro(1-6C)alkyl, difluoro(1-6C)alkyl, trifluoro(1-6C)alkyl, tetrafluoro(2-6C) alkyl or pentafluoro(2-6C)alkyl. In one embodiment, $R^4$ is fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl or 2,2,3,3,3-pentafluoropropyl In one embodiment, $R^4$ is trifluoro(1-6C)alkyl. In one embodiment, $R^4$ is $CF_3$.

In one embodiment, $R^4$ is cyano(1-6C)alkyl. In one embodiment, $R^4$ is cyanomethyl or 2-cyanopropan-2-yl.

In one embodiment, $R^4$ is hydroxy(1-6C)alkyl. In one embodiment, $R^4$ is hydroxymethyl, 2-hydroxyethyl, 2-hydroxypropyl, 2-hydroxy-2-methylpropyl or 1-hydroxy-2-methylpropan-2-yl.

In one embodiment, $R^4$ is dihydroxy(2-6C)alkyl. In one embodiment, $R^4$ is 2,3-dihydroxypropyl.

In one embodiment, $R^4$ is (1-3C alkoxy)(1-6C)alkyl. In one embodiment, $R^4$ is methoxymethyl, 2-methoxyethyl or 3-methoxypropyl.

In one embodiment, $R^4$ is amino(1-6C)alkyl. In one embodiment, $R^4$ is aminomethyl, 2-aminoethyl or 3-aminopropyl.

In one embodiment, $R^4$ is aminocarbonyl(1-6C)alkyl. In one embodiment, $R^4$ is aminocarbonylmethyl and 2-(aminocarbonyl)ethyl.

In one embodiment, $R^4$ is (1-3C)alkylsulfonamido(1-6C)alkyl. In one embodiment, $R^4$ is $CH_3SO_2NHCH_2$— or $CH_3SO_2NHCH_2CH_2$—.

In one embodiment, $R^4$ is hydroxycarbonyl(1-6C)alkyl. In one embodiment, $R^4$ is $HOC(=O)CH_2$— and $HOC(=O)CH_2CH_2$—.

In one embodiment, $R^4$ is hetAr³(1-6C)alkyl, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, $R^4$ when represented by hetAr³(1-6C)alkyl is (1-methyl-1H-1,2,4-triazol-3-yl)methyl or (5-methyl-1,3,4-oxadiazol-2-yl)methyl.

In one embodiment, $R^4$ is Ar³(1-6C)alkyl, where phenyl optionally substituted with (1-4C)alkoxy or hydroxy(1-4C)alkyl. In one embodiment, Ar³(1-6C)alkyl is benzyl.

In one embodiment, $R^4$ is (1-6C)alkoxy. Examples include methoxy and ethoxy.

In one embodiment, $R^4$ is monofluoro(1-6C)alkoxy, difluoro(1-6C)alkoxy, trifluoro(1-6C)alkoxy, tetrafluoro(2-6C)alkoxy or pentafluoro(2-6C)alkoxy. In one embodiment, $R^4$ is fluoromethoxy, 2-fluoroethoxy, 2,2-difluoromethoxy, trifluoromethoxy, 2,2,2-trifluoroethoxy or 2,2-difluoroethoxy. In one embodiment, $R^4$ is 2-fluoroethoxy.

In one embodiment, $R^4$ is cyano(1-6C)alkoxy. In one embodiment, $R^4$ is cyanomethoxy or 2-cyanoethoxy.

In one embodiment, $R^4$ is hydroxy(1-6C)alkoxy. In one embodiment, $R^4$ is 2-hydroxy-2-methylpropoxy, 2-hydroxyethoxy, 2-hydroxypropoxy, 2-hydroxy-2-methylpropoxy or 2-hydroxybutoxy.

In one embodiment, $R^4$ is dihydroxy(2-6C)alkoxy. In one embodiment, $R^4$ is 2,3-dihydroxypropoxy or 3-hydroxy-2-(hydroxymethyl)propoxy.

In one embodiment, $R^4$ is amino(2-6C)alkoxy. In one embodiment, $R^4$ is $H_2NCH_2CH_2O$—.

In one embodiment, $R^4$ is hetCyc²(1-6C)alkoxy, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or and 1,3-dioxolanyl optionally substituted with 1-2 groups independently selected from (1-6C)alkyl, (1-4C alkoxy)carbonyl and (1-6C)acyl. In one embodiment, $R^4$ when represented by hetCyc²(1-6C)alkoxy is oxetan-2-ylmethoxy, 2-(oxetan-2-yl)propoxy, 2-morpholinoethoxy, piperazinylethyoxy or piperidinylethoxy optionally substituted with 1-2 groups independently selected from (1-6C)alkyl, (1-4C alkoxy)carbonyl and (1-6C)acyl. In one embodiment, $R^4$ is represented by the structures:

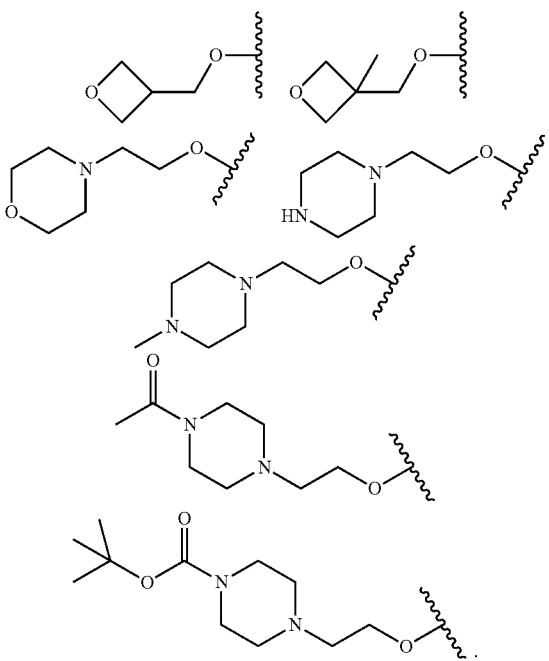

In one embodiment, $R^4$ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. In one embodiment, $R^4$ when represented by hetAr³(1-6C)alkoxy is (1-methyl-1H-1,2,4-triazol-3-yl)methoxy or (5-methyl-1,3,4-oxadiazol-2-yl)methoxy, which can be represented by the structures:

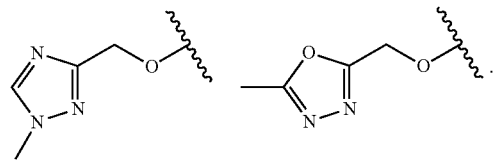

In one embodiment, $R^4$ is Ar³(1-6C)alkoxy, where $Ar^a$ is phenyl optionally substituted with (1-4C)alkoxy. In one embodiment, $R^4$ is phenylmethoxy or (4-methoxyphenyl)methoxy having the structures:

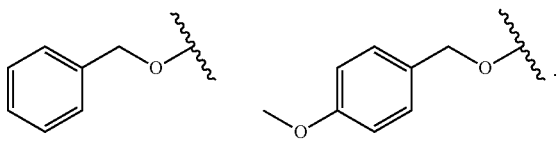 [SMILES: *OCc1ccccc1 ; *OCc1ccc(OC)cc1]

In one embodiment, R⁴ is (1-4C alkoxy)(1-6C)alkoxy. In one embodiment, R⁴ is (2-methoxy)ethoxy having the structure:

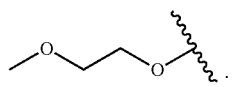 [SMILES: *OCCOC]

In one embodiment, R⁴ is (1-3Calkylsulfonyl)(1-6C)alkoxy. In one embodiment, R⁴ is (2-methylsulfonyl)ethoxy having the structure:

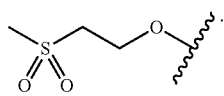 [SMILES: *OCCS(C)(=O)=O]

In one embodiment, R⁴ is (3-6C)cycloalkyl optionally substituted with F, OH, (1-6C alkyl), (1-6C)alkoxy or (1-3C alkoxy)(1-6C)alkyl. Examples include cyclopropyl, cyclobutyl, cyclopentyl, cyclohexyl, 2-hydroxycyclobutyl. In one embodiment, R⁴ is cyclopropyl or 2-hydroxycyclobutyl. In one embodiment, R⁴ is cyclopropyl.

In one embodiment, R⁴ is hetAr⁴, where hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(═O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂-(3-6C cycloalkyl)C(═O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C)alkyl, halogen, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(═O)—, (1-3C alkoxy)(1-6C)alkyl, (1-6C)alkoxy, (1-6C)alkylsulfonyl, NH₂, (1-6C alkyl)amino, di(1-6C alkyl)amino, fluoro(1-6C alkyl)amino, difluoro(1-6C alkyl)amino, trifluoro(1-6C alkyl)amino, (3-4C cycloalkyl)amino, (and 1-3C trifluoroalkoxy)(1-3C)trifluoroalkyl.

In one embodiment, R⁴ is hetAr⁴, where hetAr⁴ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ is hetAr⁴, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N and cyclopropylNH—.

In one embodiment, R⁴ when represented by hetAr⁴ is selected from the structures:

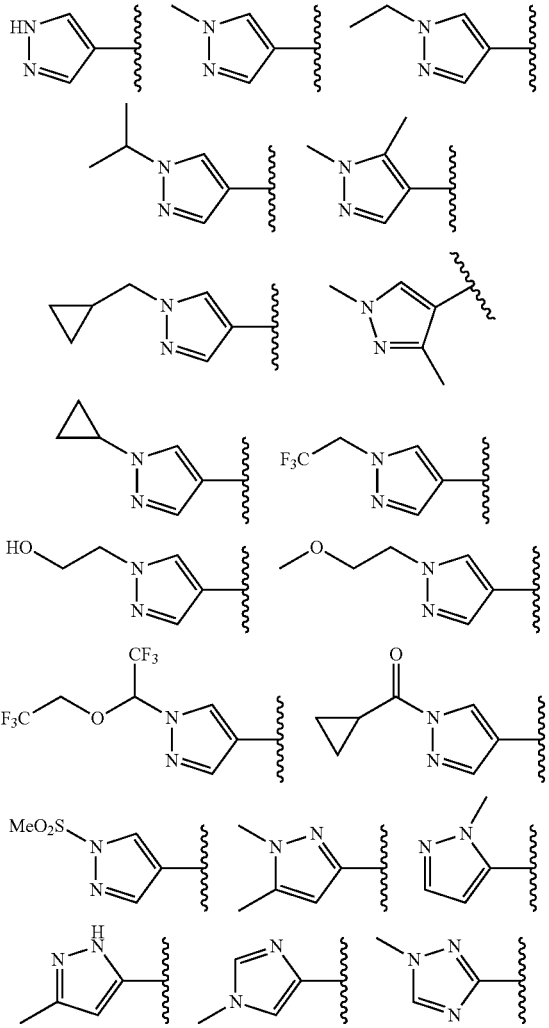

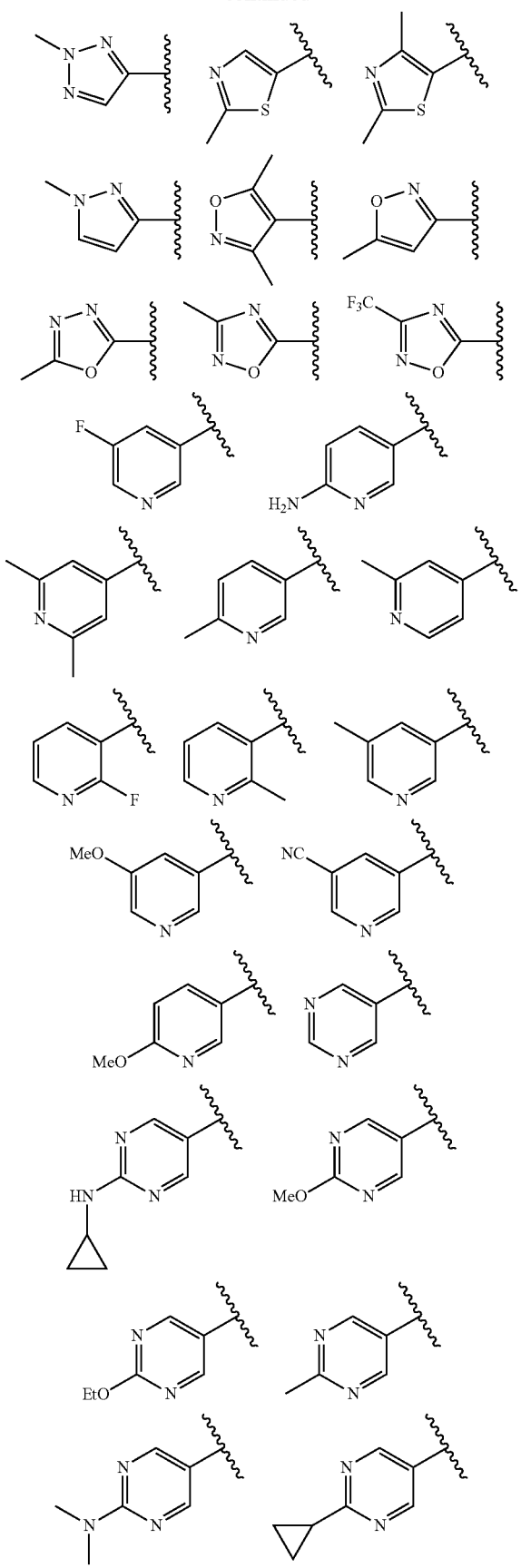

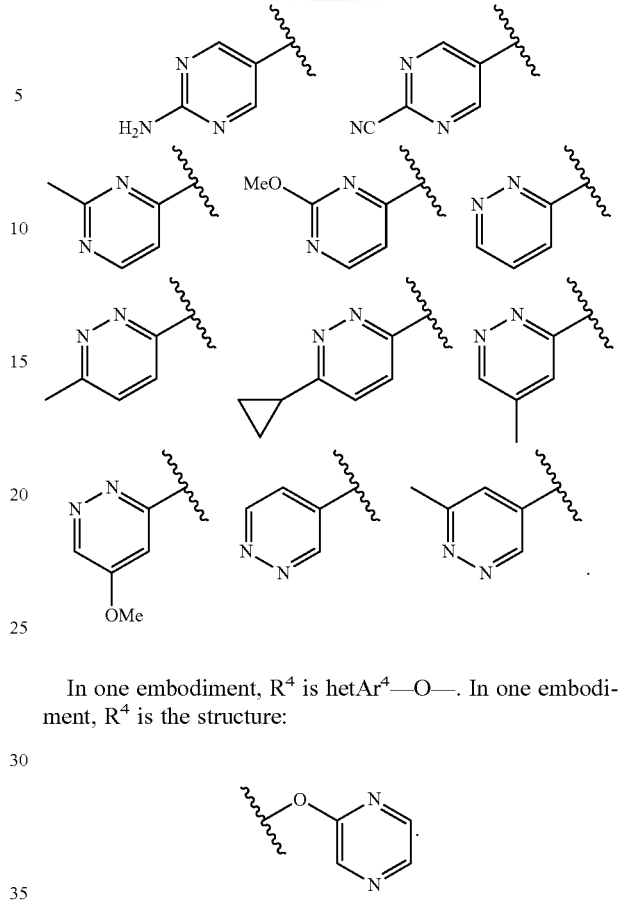

In one embodiment, R⁴ is hetAr⁴—O—. In one embodiment, R⁴ is the structure:

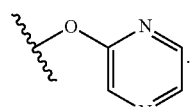

In one embodiment, R⁴ is Ar⁴, where Ar⁴ is phenyl optionally substituted with one or more substituents independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—. In one embodiment, Ar⁴ is phenyl optionally substituted with one or more substituents independently selected from methyl, F, Cl, CN, methoxy, CH₃OC(=O)—, aminocarbonyl, methylaminocarbonyl, dimethylaminocarbonyl, methylthio, CH₃SO₂—, HOC(=O)— and CH₃OCH₂CH₂OC(=O)—. In one embodiment, Ar⁴ is phenyl optionally substituted with one or two of said substituents. In one embodiment, Ar⁴ is selected from the structures:

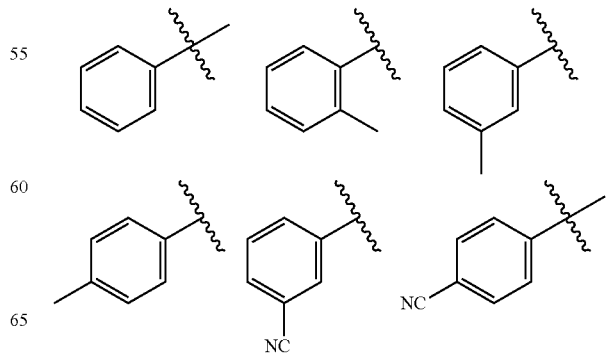

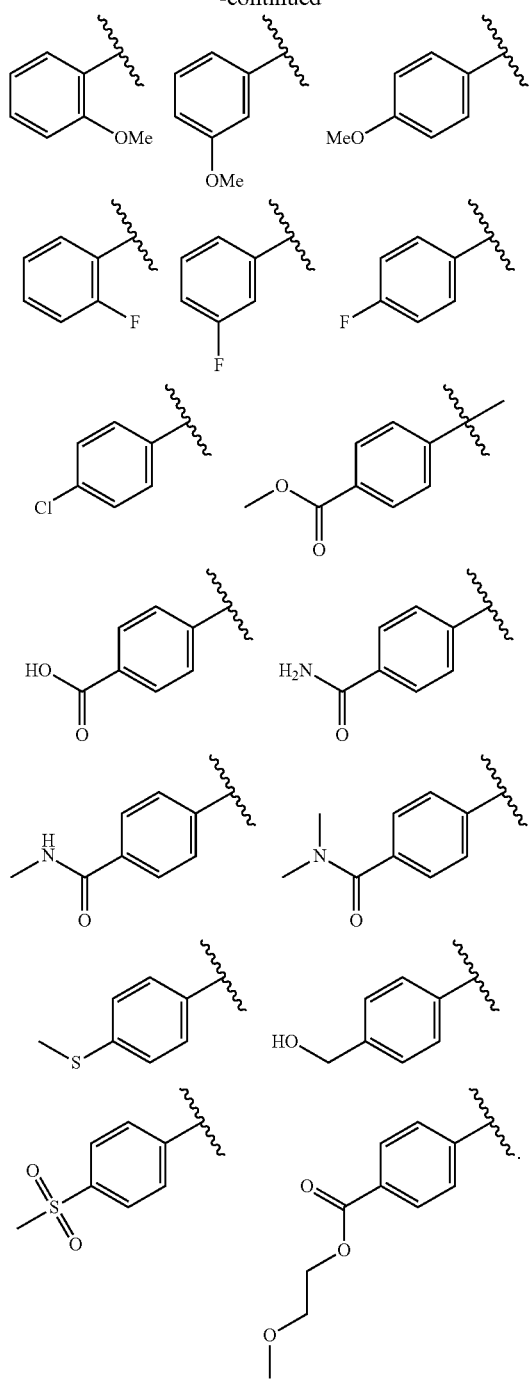

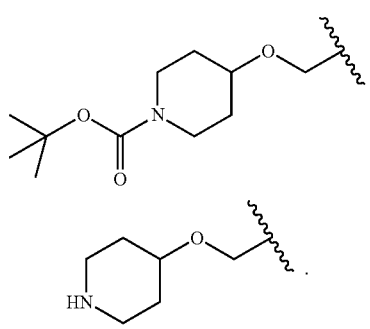

In one embodiment, R⁴ is (1-4C alkoxycarbonyl)(1-6C) alkoxy. In one embodiment, R⁴ is methoxycarbonyl(1-6C) alkoxy or ethyoxycarbonyl(1-6C)alkoxy. A particular example is ethoxycarbonylmethoxy.

In one embodiment, R⁴ is hydroxycarbonyl(1-6C)alkoxy. In one embodiment, R⁴ is hydroxycarbonylmethoxy.

In one embodiment, R⁴ is aminocarbonyl(1-6C)alkoxy. In one embodiment, R⁴ is H₂NC(=O)(1-6C)alkoxy, (1-6C alkyl)NHC(=O)(1-6C)alkoxy, or di(1-6Calkyl)NC(=O) (1-6C)alkoxy. In one embodiment, R⁴ is H₂NC(=O) CH₂O—, H₂NC(=O)CH₂CH₂O— or CH₃CH₂NC(=O) CH₂O—.

In one embodiment, R⁴ is hetCyc²C(=O)(1-6C)alkoxy, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O) (1-6C)alkoxy is the structure:

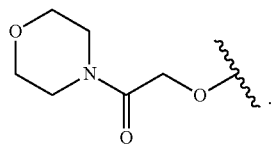 [SMILES: *OCC(=O)N1CCOCC1]

In one embodiment, R⁴ is hydroxy(1-3C alkoxy)(1-6C) alkoxy. In one embodiment, R⁴ is 2-hydroxy-3-methoxypropoxy, having the structure:

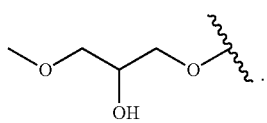 [SMILES: *OCC(O)COC]

In one embodiment, R⁴ is hydroxytrifluoro(1-6C)alkoxy. In one embodiment, R⁴ is 3,3,3-difluoro-2-hydroxypropoxy having the structure:

In one embodiment, R⁴ is hetCyc²(O)CH₂, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, R⁴ when represented by hetCyc²(O)CH₂ is selected from the structures:

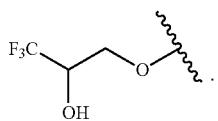

In one embodiment, $R^4$ is (1-3C)alkylsulfonamido(1-6C)alkoxy. In one embodiment, $R^4$ is methanesulfonamido(1-6C)alkoxy. In one embodiment, $R^4$ is 2-methanesulfonamidoethoxy having the structure:

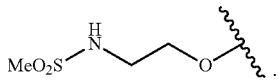

In one embodiment, $R^4$ is (1-3C)alkylamido(1-6C)alkoxy. In one embodiment, $R^4$ is 2-(methylamido)ethoxy having the structure:

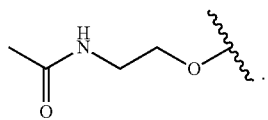 [SMILES: *OCCNC(C)=O]

In one embodiment, $R^4$ is di(1-3C alkyl)aminocarboxy. In one embodiment, $R^4$ is dimethylaminocarboxy having the structure:

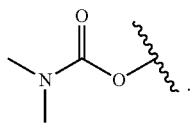 [SMILES: *OC(=O)N(C)C]

In one embodiment, $R^4$ is hetCyc$^2$C(=O)O—, where hetCyc$^2$ is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. In one embodiment, hetCyc$^2$ is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc$^2$ is morpholinyl. In one embodiment, $R^4$ when represented by hetCyc$^2$C(=O)O— is the structure:

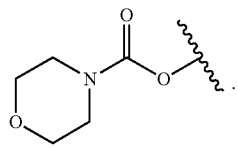

In one embodiment, $R^4$ is hydroxydifluoro(1-6C)alkyl. In one embodiment, $R^4$ is 2,2-difluro-2-hydroxyethyl.

In one embodiment, $R^4$ is (1-4C alkylcarboxy)(1-6C)alkyl. In one embodiment, $R^4$ is methylcarboxy(1-6C)alkyl. In one embodiment, $R^4$ is 2-(methylcarboxy)ethyl.

In one embodiment, $R^4$ is (1-6C)alkoxycarbonyl. In one embodiment, $R^4$ is methoxycarbonyl or ethoxycarbonyl.

In one embodiment, $R^4$ is hydroxycarbonyl.

In one embodiment, $R^4$ is aminocarbonyl, that is, a RR'NCO— radical where R and R' are independently hydrogen or (1-6C)alkyl as defined herein. In one embodiment, $R^4$ is aminocarbonyl, methylaminocarbonyl, dimethylaminocarbonyl, ethylcarbonyl or isopropylaminocarbonyl.

In one embodiment, $R^4$ is hetCyc$^3$, where is a 4-7 membered heterocycle having 1-2 ring heteroatoms independently selected from N and O and optionally substituted with one or more substituents independently selected from F, CN, CF$_3$, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc$^3$ is tetrahydropyranyl, piperidinyl, pyrrolidinyl or azetidinyl optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc$^3$ is optionally substituted with one or two of said substituents. In one embodiment, hetCyc$^3$ is tetrahydropyranyl, piperidinyl, pyrrolidinyl or azetidinyl optionally substituted with CN, Me, CH$_3$C(=O)—, MeSO$_2$—, or CF$_3$SO$_2$—. In one embodiment, $R^4$ when represented by hetCyc$^3$ is selected from the structures:

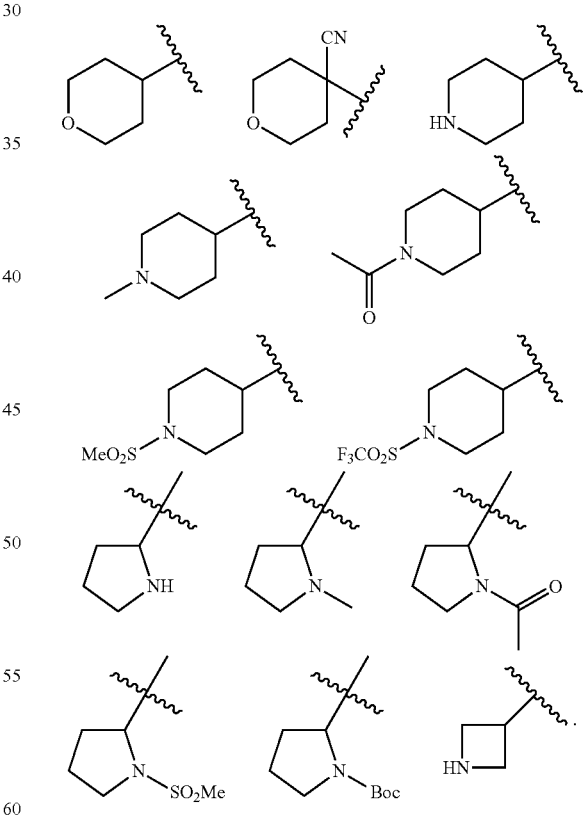

In one embodiment, $R^4$ is halogen. In one embodiment, $R^4$ is Br.

In one embodiment, $R^4$ is CN.

In one embodiment, $R^4$ is trifluoromethylsulfonyl.

In one embodiment, $R^4$ is hetAr$^5$, where hetAr$^5$ is a group selected from the structures:

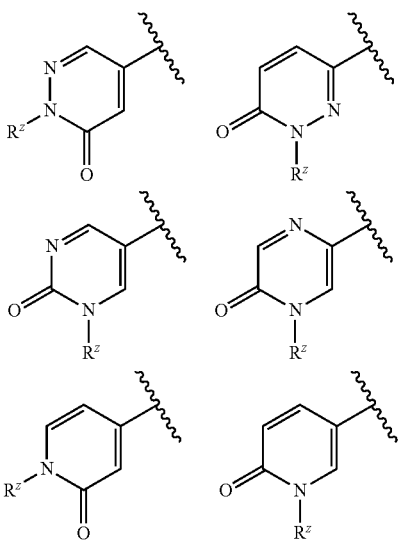

where $R^z$ is (3-4C)cycloalkyl or (1-3C)alkyl (optionally substituted with 1-3 fluoros), wherein each of said hetAr$^5$ groups is optionally further substituted with one or more substituents independently selected from F and (1-3C)alkyl optionally substituted with 1-3 fluoros.

In one embodiment, R$^4$ when represented by hetAr$^5$ is selected from the structures:

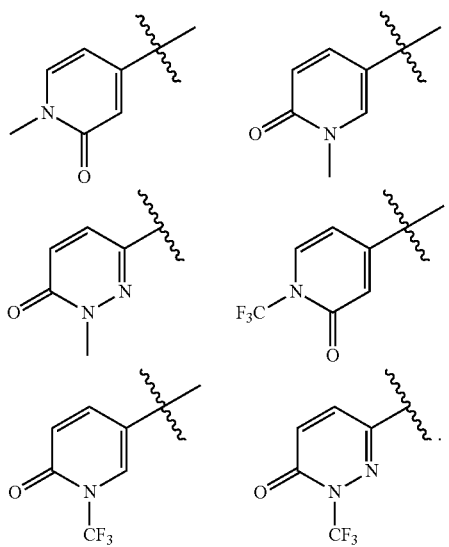

In one embodiment, R$^4$ is N-(1-3C alkyl)oxadiazolonyl. In one embodiment, R$^4$ is represented by the structures:

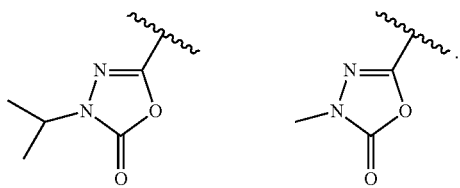

In one embodiment, R$^4$ is selected from H, (1-6C)alkyl, trifluoro(1-6C)alkyl, hydroxy(1-6C)alkyl, cyano(1-6C)alkyl, (1-3C alkoxy)(1-6C)alkyl, (1-6C)alkoxy, monofluoro(1-6C)alkoxy, cyano(1-6C)alkoxy, hydroxy(1-6C)alkoxy, dihydroxy(2-6C)alkoxy, hetCyc$^2$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl, hetAr$^4$, hetAr$^4$—O—, Ar$^4$, and hetAr$^5$.

In one embodiment, R$^4$ is hetAr$^4$, Ar$^4$, or hetAr$^5$.

In one embodiment, R$^4$ is hetAr$^4$ or hetAr$^5$.

In one embodiment, R$^4$ is pyrazolyl optionally substituted with one or more substituents independently selected from (1-6C)alkyl, or a hetAr$^5$ group having the structure:

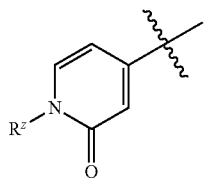

where $R^z$ is (3-4C)cycloalkyl or (1-3C)alkyl (optionally substituted with 1-3 fluoros), wherein said hetAr$^5$ group is optionally further substituted with one or more substituents independently selected from F and (1-3C)alkyl optionally substituted with 1-3 fluoros.

In one embodiment of Formula I, R$^4$ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr$^4$, and hetCyc$^3$.

In one embodiment, R$^5$ is (1-6C)alkyl. In one embodiment, R$^5$ is methyl, ethyl, propyl, isopropyl or butyl.

In one embodiment, R$^5$ is monofluoro(1-6C)alkyl, difluoro(1-6C)alkyl, trifluoro(1-6C)alkyl, tetrafluro(2-6C)alkyl or pentafluro(2-6C)alkyl. In one embodiment, R$^5$ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane or 2,2,3,3,3-pentafluoropropyl.

In one embodiment, R$^5$ is halogen. In one embodiment, R$^5$ is F. In one embodiment, R$^5$ is Cl. In one embodiment, R$^5$ is Br.

In one embodiment, R$^5$ is CN.

In one embodiment, R$^5$ is (1-4C)alkoxy. In one embodiment, R$^5$ is methoxy or ethoxy.

In one embodiment, R$^5$ is hydroxy(1-4C)alkyl. In one embodiment, R$^5$ is hydroxymethyl or 3-hydroxypropyl.

In one embodiment, R$^5$ is (1-4C alkyl)OC(=O)—. In one embodiment, R$^5$ is CH$_3$CH$_2$OC(=O)—.

In one embodiment, R$^5$ is (1-6C)alkylthio. In one embodiment, R$^5$ is methylthio (MeS—).

In one embodiment, R$^5$ is phenyl optionally substituted with one or more substituents independently selected from halogen, (1-6C)alkyl and (1-6C)alkoxy. In one embodiment, R$^5$ is phenyl optionally substituted with one or more substituents independently selected from F, Cl, methyl, ethyl, methoxy and ethoxy. In one embodiment, R$^5$ is phenyl.

In one embodiment, R$^5$ is (3-4C)cycloalkyl. In one embodiment, R$^5$ is cyclopropyl. In one embodiment, R$^5$ is cyclobutyl.

In one embodiment, R$^5$ is amino. In one embodiment, R$^5$ is NH$_2$.

In one embodiment, R$^5$ is aminocarbonyl. In one embodiment, R$^5$ is H$_2$NC(=O)—.

In one embodiment, $R^5$ is trifluoro(1-3C alkyl)amido. In one embodiment, $R^5$ is $CF_3C(=O)NH-$.

In one embodiment, $R^5$ is halogen, CN, (1-6C)alkyl, (1-4C)alkoxy, hydroxy(1-4C)alkyl, or phenyl [optionally substituted with one or more substituents independently selected from halogen, (1-6C)alkyl and (1-6C)alkoxy].

In one embodiment, $R^5$ is selected from halogen, and (1-6C)alkyl.

In one embodiment, $R^5$ is selected from methyl, Cl and Br.

In one embodiment of Formula I, $R^4$ is (1-6C)alkyl, (1-3C alkoxy)(1-6C)alkyl, (1-6C)alkoxy, hydroxy(1-6C)alkoxy, dihydroxy(2-6C)alkoxy, hydroxy(1-3C)alkoxy(1-6C)alkoxy, hetAr$^4$, or hetCyc$^3$; and $R^5$ is (1-6C)alkyl.

In one embodiment of Formula I, $R^4$ is hetAr$^4$, Ar$^4$, or hetAr$^5$; and $R^5$ is (1-6C)alkyl.

In one embodiment of Formula I, $R^4$ is hetAr$^4$ or hetAr$^5$; and $R^5$ is (1-6C)alkyl.

In one embodiment of Formula I, $R^4$ is hetAr$^4$ and $R^5$ is (1-6C)alkyl.

In one embodiment of Formula I, $R^4$ is pyrazolyl optionally substituted with one or more substituents independently selected from (1-6C)alkyl; and $R^5$ is (1-6C)alkyl.

In one embodiment of Formula I, $R^4$ is hetAr$^5$; and $R^5$ is (1-6C)alkyl.

In one embodiment of Formula I, $R^4$ is a hetAr$^5$ group having the structure:

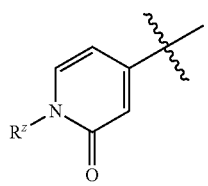

where $R^z$ is (3-4C)cycloalkyl or (1-3C)alkyl (optionally substituted with 1-3 fluoros), wherein said hetAr$^5$ group is optionally further substituted with one or more substituents independently selected from F and (1-3C)alkyl optionally substituted with 1-3 fluoros; and $R^5$ is selected from (1-6C)alkyl.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl; or $R^4$ and $R^5$ together with the atoms to which they are attached form a 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO$_2$.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl. In one embodiment, Ring C when $R^4$ and $R^5$ together with the atoms to which they are attached form a 5-6 membered saturated or unsaturated carbocyclic ring is selected from the structures:

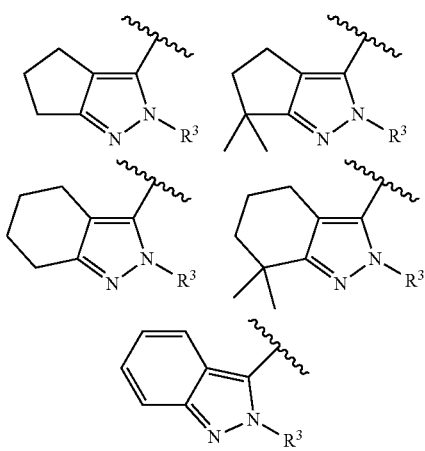

where $R^3$ is as defined for Formula I. In one embodiment, $R^3$ is phenyl.

In one embodiment, $R^4$ and $R^5$ together with the atoms to which they are attached form a 5-6 membered saturated carbocyclic ring optionally substituted with one or more substituents independently selected from (1-6C)alkyl, or $R^4$ and $R^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6C)acyl, and said sulfur ring atom is optionally oxidized to S(=O) or SO$_2$.

In one embodiment, $R^4$ and $R^5$ together with the atoms to which they are attached form a 5-6 membered saturated carbocyclic ring optionally substituted with one or more substituents independently selected from (1-6C)alkyl. In one embodiment, Ring C when $R^4$ and $R^5$ together with the atoms to which they are attached form a 5-6 membered saturated carbocyclic ring is selected from the structures:

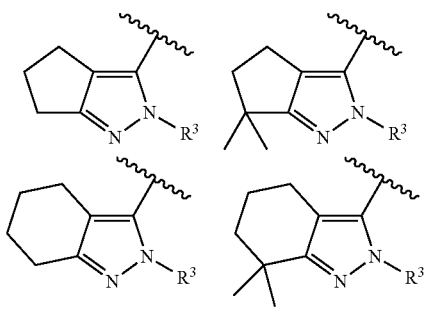

where $R^3$ is as defined for Formula I. In one embodiment, $R^3$ is Ar$^2$. In one embodiment, $R^3$ is phenyl.

In one embodiment, $R^4$ and $R^5$ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O)O—, (1-6C alkyl)C(=O)—, (1-6C)alkyl or oxo, and said S ring atom is optionally oxidized to S(=O) or SO$_2$. In one embodiment, Ring C when $R^4$ and $R^5$ together with the atoms to which they are attached form a 5-6 membered saturated heterocyclic ring is selected from the structures:

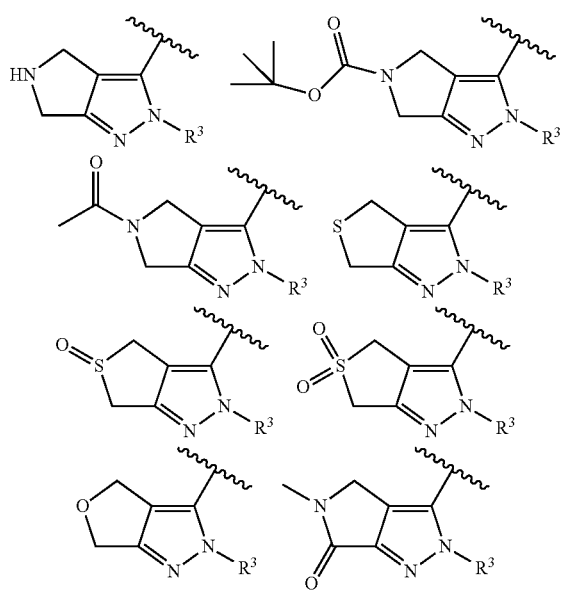

where R³ is as defined for Formula I. In one embodiment, R³ is Ar². In one embodiment, R³ is phenyl.

In one embodiment, R⁴ and R⁵ together with the atoms to which they are attached form a 5-6 membered saturated heterocyclic ring having a ring heteroatom selected from N, O or S, wherein said ring N atom is optionally substituted with (1-6C alkyl)C(=O)O— or (1-6C alkyl)C(=O)—, and said S ring atom is optionally oxidized to S(=O) or SO₂. In one embodiment, Ring C when R⁴ and R⁵ together with the atoms to which they are attached form a 5-6 membered saturated heterocyclic ring is selected from the structures:

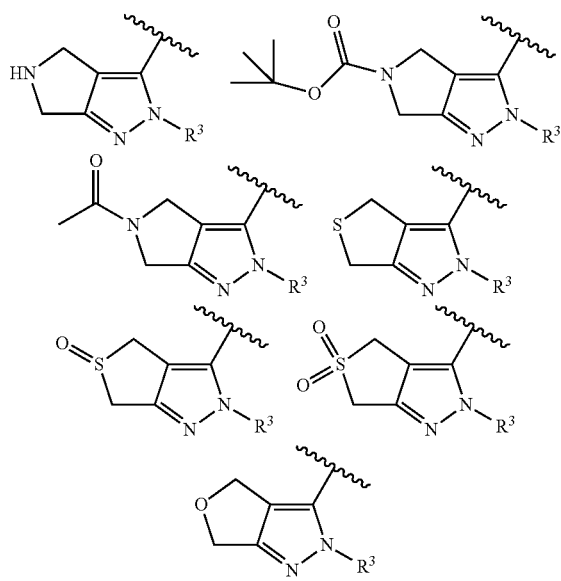

where R³ is as defined for Formula I. In one embodiment, R³ is Ar². In one embodiment, R³ is phenyl.

In one embodiment of Formula I, R⁴ and R⁵ together with the atoms to which they are attached form a 5-6 membered saturated heterocyclic ring having a ring heteroatom selected from N, O or S, wherein said S ring atom is optionally oxidized to S(=O) or SO₂, or R⁴ and R⁵ together with the atoms to which they are attached form a 5-6 membered saturated carbocyclic ring; and R³ is Ar².

In one embodiment, Ring C is formula C-2

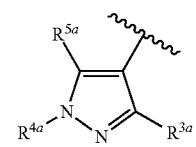

C-2 where R³ᵃ, R⁴ᵃ and R⁵ᵃ are as defined for Formula I.
In one embodiment, R³ᵃ is hydrogen.
In one embodiment, R³ᵃ is halogen.
In one embodiment, R³ᵃ is (1-6C)alkyl. In one embodiment, R³ᵃ is methyl.
In one embodiment, R³ᵃ is trifluoro(1-6C)alkyl. In one embodiment, R³ᵃ is CF₃.
In one embodiment, R³ᵃ is (3-6C)cycloalkyl. In one embodiment, R³ᵃ is cyclopropyl.
In one embodiment, R³ᵃ is phenyl optionally substituted with one or more substituents independently selected from halogen and (1-6C)alkyl. In one embodiment, R³ᵃ is phenyl, fluorophenyl or methylphenyl, for example include phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, R³ᵃ is phenyl.
In one embodiment, R³ᵃ is a 5-6 membered heteroaryl ring having 1-3 ring heteroatoms independently selected from N, O and S and optionally substituted with one or more substituents independently selected from (1-6C)alkyl and halogen. In one embodiment, R³ᵃ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C)alkyl or halogen. In one embodiment, R³ᵃ is pyrazolyl, pyridyl or pyridazinyl optionally substituted with one or more substituents independently selected from (1-6C) alkyl and halogen. In one embodiment, R³ᵃ is pyrazolyl, pyridyl or pyridazinyl optionally substituted with (1-6C) alkyl or halogen.
In one embodiment, R⁴ᵃ is hydrogen.
In one embodiment, R⁴ᵃ is (1-6C)alkyl. In one embodiment, R⁴ᵃ is methyl, ethyl or isopropyl.
In one embodiment, R⁴ᵃ is trifluoro(1-6C)alkyl. In one embodiment, R⁴ᵃ is 2,2,2-trifluoroethyl.
In one embodiment, R⁴ᵃ is phenyl optionally substituted with one or more substituents independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—. In one embodiment, R⁴ᵃ is phenyl optionally substituted with one or more substituents independently selected from methyl, F, Cl, CN, methoxy, CH₃OC(=O)—, aminocarbonyl, methylaminocarbonyl, dimethylaminocarbonyl, methylthio, CH₃SO₂—, HOC(=O)— and CH₃OCH₂CH₂OC(=O)—. In certain embodiments, R⁴ᵃ is phenyl optionally substituted with one or two of said substituents. In one embodiment, R⁴ᵃ is phenyl.
In one embodiment, R⁴ᵃ is a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, and (1-3C trifluoroalkoxy)(1-3C)trifluoroalkyl. In one embodiment, R$^{4a}$ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, and (1-3C trifluoroalkoxy)(1-3C)trifluoroalkyl. In one embodiment, R$^{4a}$ is pyrazinyl.

In one embodiment, R$^{5a}$ is as defined for Formula I.

In one embodiment, R$^{5a}$ is selected from hydrogen, halogen, (1-6C)alkyl and phenyl.

In one embodiment, R$^{5a}$ is hydrogen.

In one embodiment, R$^{5a}$ is halogen.

In one embodiment, R$^{5a}$ is (1-6C)alkyl. In one embodiment, R$^{5a}$ is methyl.

In one embodiment, R$^{5a}$ is phenyl.

In one embodiment, Ring C is formula C-2, in which R$^{3a}$ is (1-6C)alkyl, trifluoro(1-6C)alkyl or phenyl; R$^{4a}$ is (1-6C)alkyl, trifluoro(1-6C)alkyl, phenyl or pyrazinyl; and R$^{5a}$ is hydrogen, (1-6C)alkyl or phenyl.

In another embodiment of the present invention there is provided a compound according to Formula I, which is designated as Formula I-a, wherein:

X is O;

Ring C is C-1

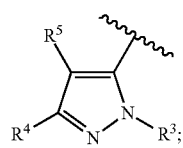

C-1

R$^3$ is (1-6C)alkyl, hydroxy(1-6C)alkyl, Ar$^2$, hetCyc$^1$, (3-7C)cycloalkyl, or hetAr$^2$;

R$^4$ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc$^2$(1-6C)alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C)alkoxy, or (1-3C alkoxy)(1-6C)alkyl], hetAr$^4$, hetAr$^4$—O—, Ar$^4$, hetCyc$^2$(O)CH$_2$—, (1-4C alkoxycarbonyl)(1-6C)alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)amino-carboxy, hetCyc$^2$C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc$^3$, halogen, CN, trifluoromethylsulfonyl, N-(1-3C alkyl)oxadiazolonyl, or hetAr$^5$;

R$^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, or phenyl optionally substituted with one or more substituents independently selected from halogen, (1-6C)alkyl and (1-6C)alkoxy;

or R$^4$ and R$^5$ together with the atoms to which they are attached form a 5-6 membered saturated heterocyclic ring having a ring heteroatom selected from N, O or S, wherein said S ring atom is optionally oxidized to S(=O) or SO$_2$;

or R$^4$ and R$^5$ together with the atoms to which they are attached form a 5-6 membered saturated carbocyclic ring;

and Ring A, R$^1$, Y, Ar$^2$, hetCyc$^1$, hetCyc$^2$, hetCyc$^3$, hetAr$^3$, Ar$^a$, hetAr$^4$, hetAr$^5$, le, and Ar$^4$ are as defined for Formula I.

In one embodiment of Formula I-a, R$^3$ is Ar$^2$; R$^4$ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr$^4$, hetCyc$^3$, Ar$^4$ and hetAr$^5$; R$^5$ is selected from (1-6C)alkyl; or R$^4$ and R$^5$ together with the atoms to which they are attached form a 5-6 membered saturated heterocyclic ring having a ring heteroatom selected from N, O or S, wherein said S ring atom is optionally oxidized to S(=O) or SO$_2$; or R$^4$ and R$^5$ together with the atoms to which they are attached form a 5-6 membered saturated carbocyclic ring; and Ring A, R$^1$, Y, Ar$^2$, hetAr$^4$, hetCyc$^3$, Ar$^4$, and hetAr$^5$ are as defined for Formula I. In one embodiment of Formula I-a, R$^3$ is phenyl.

In one embodiment of Formula I-a, R$^3$ is Ar$^2$; R$^4$ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr$^4$, and hetCyc$^3$; R$^5$ is selected from (1-6C)alkyl; or R$^4$ and R$^5$ together with the atoms to which they are attached form a 5-6 membered saturated heterocyclic ring having a ring heteroatom selected from N, O or S, wherein said S ring atom is optionally oxidized to S(=O) or SO$_2$; or R$^4$ and R$^5$ together with the atoms to which they are attached form a 5-6 membered saturated carbocyclic ring; and Ring A, R$^1$, Y, Ar$^2$, hetAr$^4$ and hetCyc$^3$ are as defined for Formula I. In one embodiment of Formula I-a, R$^3$ is phenyl.

In one embodiment of Formula I-a, R$^3$ is Ar$^2$; R$^4$ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr$^4$, hetCyc$^3$; R$^5$ is selected from (1-6C)alkyl; or R$^4$ and R$^5$ together with the atoms to which they are attached form a 5-6 membered saturated heterocyclic ring having a ring heteroatom selected from N, O or S, wherein said S ring atom is optionally oxidized to S(=O) or SO$_2$; or R$^4$ and R$^5$ together with the atoms to which they are attached form a 5-6 membered saturated carbocyclic ring; Ring A is formula A-1; and R$^1$, Y, Ar$^2$, hetAr$^4$ and hetCyc$^3$ are as defined for Formula I. In one embodiment of Formula I-a, R$^3$ is phenyl.

In one embodiment of Formula I-a, R$^3$ is Ar$^2$; R$^4$ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr⁴, hetCyc³; R⁵ is selected from (1-6C)alkyl; or R⁴ and R⁵ together with the atoms to which they are attached form a 5-6 membered saturated heterocyclic ring having a ring heteroatom selected from N, O or S, wherein said S ring atom is optionally oxidized to S(=O) or SO₂; or R⁴ and R⁵ together with the atoms to which they are attached form a 5-6 membered saturated carbocyclic ring; Ring A is formula A-2; and R¹, Y, Ar², hetAr⁴ and hetCyc³ are as defined for Formula I. In one embodiment of Formula I-a, R³ is phenyl.

In one embodiment of Formula I-a, R³ is Ar²; R⁴ is selected from (1-6C)alkyl, hydroxy(1-6C)alkyl, dihydroxy(2-6C)alkyl, (1-3C alkoxy)(1-6C)alkyl, (1-6C)alkoxy, hydroxy(1-6C)alkoxy, dihydroxy(2-6C)alkoxy, hetAr⁴, hetCyc³; R⁵ is selected from (1-6C)alkyl; or R⁴ and R⁵ together with the atoms to which they are attached form a 5-6 membered saturated heterocyclic ring having a ring heteroatom selected from N, O or S, wherein said S ring atom is optionally oxidized to S(=O) or SO₂; or R⁴ and R⁵ together with the atoms to which they are attached form a 5-6 membered saturated carbocyclic ring; Ring A is formula A-3; and R¹, Y, Ar², hetAr⁴ and hetCyc³ are as defined for Formula I. In one embodiment of Formula I-a, R³ is phenyl.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts and trifluoroacetate salts.

In one embodiment, the compounds of Formula I include the free base form of compounds of Examples 1-39, or pharmaceutically acceptable salts thereof.

In one embodiment, the compounds of Formula I include the hydrochloride salts of compounds of Examples 1-39.

In one embodiment, the compounds of Formula I include the trifluoroacetate salts of compounds of Examples 1-39.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

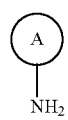

II with a corresponding compound having the formula III

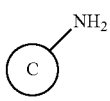

III in the presence carbonyldiimidazole or triphosgene and a base; or (b) for a compound of Formula I where X is S, coupling a corresponding compound having the formula II

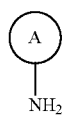

II with a corresponding compound having the formula III

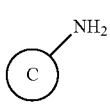

III in the presence di(1H-imidazol-2-yl)methanethione and a base; or (c) for a compound of Formula I where X is O, coupling a corresponding compound having the formula II

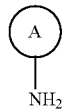

II with a corresponding compound having the formula IV

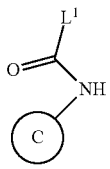

IV where L¹ is a leaving group, in the presence of a base; or (d) for a compound of Formula I where X is O, coupling a corresponding compound having the formula V

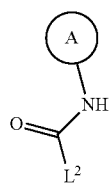

V where $L^2$ is a leaving group, with a corresponding compound having the formula III

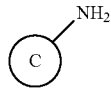

III in the presence of a base; or (e) for a compound of Formula I where X is O, activating a corresponding compound having the formula VI

VI with diphenylphosphoryl azide followed by coupling the activated intermediate with a corresponding compound having the formula III

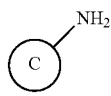

III in the presence a base; or (f) for a compound of Formula I where X is O, coupling a corresponding compound having the formula II

II with a corresponding compound having the formula VII

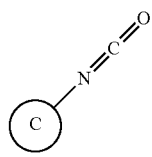

VII in the presence of a base; or (g) for a compound of Formula I where X is O, coupling a corresponding compound having the formula VIII

VIII with a corresponding compound having the formula III

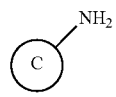

III in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for 2nd example as described in Greene & Wuts, eds., "Protecting Groups in Organic Synthesis", $2^{nd}$ ed. New York;

John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, IV, V, VI and VII are also provided as further aspects of the invention. In one embodiment, the compounds of the formulas II, III, IV, V, VI and VII are useful as intermediates for the preparation of compounds of Formula I.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;
TFG=TRK-fused gene protein;
TPM3=Tropomyosin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180 Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314 Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, *Williams & Wilkins*, 2004; Gennaro, Alfonso R., et al. *Remington: The Science and Practice of Pharmacy*. Philadelphia: Lippincott, *Williams & Wilkins*, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assay

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value <100 nM; and B represents an averaged $IC_{50}$ value from 100 to 1,000 nM.

TABLE A

| Example # | TrkA Enzyme $IC_{50}$ (nM) |
|---|---|
| 1 | A |
| 2 | A |
| 3 | A |
| 4 | A |
| 5 | B |
| 6 | B |
| 7 | A |
| 8 | A |
| 9 | B |
| 10 | B |
| 11 | B |
| 12 | A |
| 13 | A |
| 14 | A |
| 15 | A |
| 16 | B |
| 17 | A |
| 18 | A |
| 19 | A |
| 20 | A |
| 21 | A |
| 22 | A |
| 23 | B |
| 24 | B |
| 25 | A |
| 26 | A |
| 27 | A |
| 28 | A |
| 29 | A |
| 30 | A |
| 31 | B |
| 32 | B |
| 33 | A |
| 34 | A |
| 35 | B |
| 36 | A |
| 37 | B |
| 38 | A |
| 39 | B |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [$Na^+$] HEPES pH 7.3, 10 mM $MgCl_2$, 100 μM $NaVO_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data. The compounds of Examples 1-39 were tested in this assay, and all compounds were found to be 1000 fold more potent against TrkA than p38α.

Preparation of Synthetic Intermediates

Intermediate 1

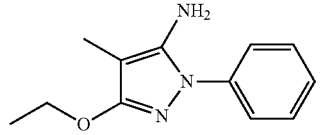 [SMILES: CCOc1nn(-c2ccccc2)c(N)c1C]

3-ethoxy-4-methyl-1-phenyl-1H-pyrazol-5-amine

Step A: Preparation of 5-amino-4-methyl-1-phenyl-1H-pyrazol-3(2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and $Et_2O$. The resultant solid was filtered, washed with $Et_2O$, and dried under vacuum to give the product as a white solid (3.4 g, 39% yield). MS (apci) m/z=190.0 (M−H).

Step B: Preparation of 3-ethoxy-4-methyl-1-phenyl-1H-pyrazol-5-amine: To a suspension of 5-amino-4-methyl-1-phenyl-1H-pyrazol-3(2H)-one (10.0 g, 52.9 mmol) in DMF (100 mL) was added $K_2CO_3$ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with $MgSO_4$, filtered, and concentrated to give the product (5.35 g, 47% yield). MS (apci) m/z=218.1 (M+H).

The compounds in Table 1 were prepared by the method as described for Intermediate 1, substituting bromoethane with the appropriate alkyl halide or alkyl methanesulfonate.

TABLE 1

| Intermediate # | Structure | Data |
|---|---|---|
| 2 | (3-methoxy-4-methyl-1-phenyl-1H-pyrazol-5-amine) | MS (apci) m/z = 204.1 (M + H) |
| 3 | (((R)-2,2-dimethyl-1,3-dioxolan-4-yl)methoxy pyrazole amine) | MS (apci) m/z = 304.1 (M + H) |
| 4 | (2-hydroxy-2-methylpropoxy pyrazole amine) | MS (apci) m/z = 262.1 (M + H) |
| 5 | (OTBS-propoxy pyrazole amine) | MS (apci) m/z = 362.0 (M + H) |
| 6 | (OTBS-propoxy pyrazole amine, other enantiomer) | MS (apci) m/z = 362.0 (M + H) |
| 7 | (((S)-2,2-dimethyl-1,3-dioxolan-4-yl)methoxy pyrazole amine) | MS (apci) m/z = 304.1 (M + H) |

Intermediate 8

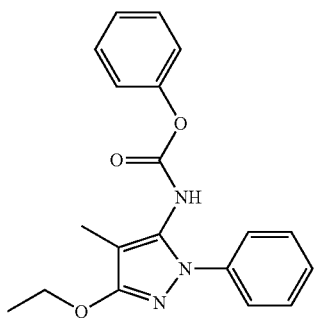 [SMILES: CCOc1nn(-c2ccccc2)c(NC(=O)Oc2ccccc2)c1C]

phenyl (3-ethoxy-4-methyl-1-phenyl-1H-pyrazol-5-yl)carbamate

To a suspension of 3-ethoxy-4-methyl-1-phenyl-1H-pyrazol-5-amine [Intermediate 1] (138 mg, 0.57 mmol) in EtOAc (7 mL) at 0° C. was added NaOH (0.57 mL, 2M, 1.14 mmol) followed by phenyl chloroformate (0.12 mL, 0.97 mmol). The reaction was stirred at ambient temperature for 17 hours then treated with EtOAc, washed with water and brine, dried over MgSO$_4$, filtered and concentrated under vacuum. The residue was purified by silica column chromatography eluting with 6:1 hexanes/EtOAc to afford the title compound (139 mg, 72% yield). MS (apci) m/z=338.0 (M+).

The compounds in Table 2 were prepared by the method as described for Intermediate 7, substituting 3-ethoxy-4-methyl-1-phenyl-1H-pyrazol-5-amine with the appropriate amine from Table 1.

TABLE 2

| Intermediate # | Structure | Data |
| --- | --- | --- |
| 9 | 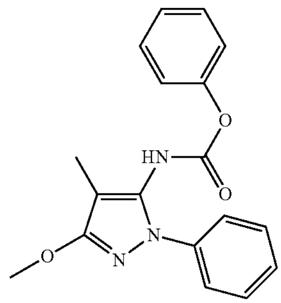 [SMILES: COc1nn(-c2ccccc2)c(NC(=O)Oc2ccccc2)c1C] | MS (apci) m/z = 324.1 (M + H) |
| 10 | 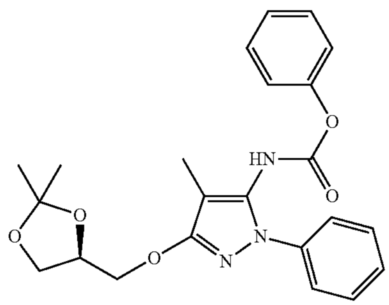 [SMILES: Cc1c(OC[C@H]2COC(C)(C)O2)nn(-c2ccccc2)c1NC(=O)Oc1ccccc1] | MS (apci) m/z = 424.2 (M + H) |
| 11 | 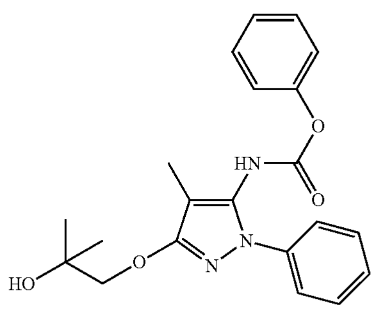 [SMILES: Cc1c(OCC(C)(C)O)nn(-c2ccccc2)c1NC(=O)Oc1ccccc1] | MS (apci) m/z = 382.2 (M + H) |
| 12 | 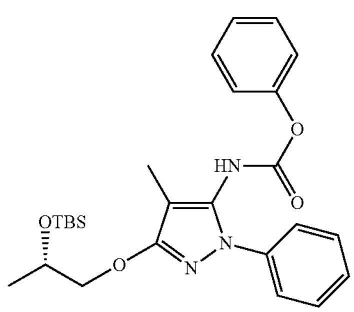 [SMILES: Cc1c(OC[C@H](C)O[Si](C)(C)C(C)(C)C)nn(-c2ccccc2)c1NC(=O)Oc1ccccc1] | MS (apci) m/z = 482.3 (M + H) |
| 13 | 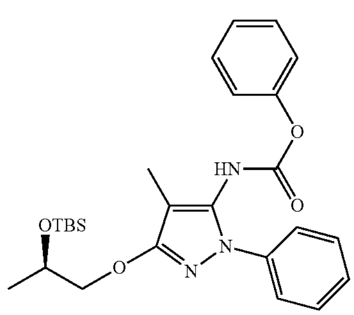 [SMILES: Cc1c(OC[C@@H](C)O[Si](C)(C)C(C)(C)C)nn(-c2ccccc2)c1NC(=O)Oc1ccccc1] | MS (apci) m/z = 482.3 (M + H) |

TABLE 2-continued

| Intermediate # | Structure | Data |
| --- | --- | --- |
| 14 | 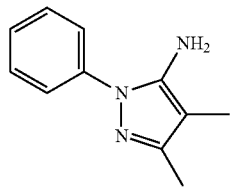 | Not available |

Intermediate 15

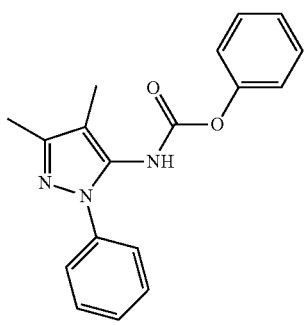 [SMILES: Cc1nn(-c2ccccc2)c(NC(=O)Oc2ccccc2)c1C]

3,4-dimethyl-1-phenyl-1H-pyrazol-5-amine

To a solution of 2-methyl-3-oxobutanenitrile (295 mg, 3.038 mmol) in EtOH (40 mL) were added HCl (5-6M in iPrOH, 0.6 mL) and phenylhydrazine (0.299 mL, 3.038 mmol). The reaction mixture was heated to reflux for 17 hours, then cooled to ambient temperature. The reaction mixture was diluted with saturated NaHCO₃ (20 mL), extracted with DCM (2×25 mL), and the combined organic phases were dried over MgSO₄, filtered and concentrated under vacuum. The residue was purified by silica column chromatography, eluting with 0-3% MeOH/DCM to yield the title compound (555 mg, 97% yield) as a tan solid. MS (apci) m/z=188.2 (M+H).

Intermediate 16

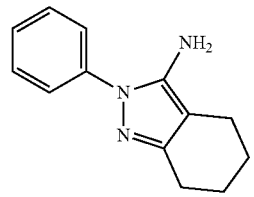 [SMILES: Nc1c2c(nn1-c1ccccc1)CCCC2]

phenyl (3,4-dimethyl-1-phenyl-1H-pyrazol-5-yl)carbamate

To a solution of 3,4-dimethyl-1-phenyl-1H-pyrazol-5-amine [Intermediate 7] (1.80 g, 9.6 mmol) in EtOAc (20 mL) was added 2N NaOH (9.6 mL, 19.2 mmol) followed by phenyl chloroformate (1.7 mL, 13.5 mmol). The mixture was stirred at ambient temperature for 16 hours then treated with phenyl chloroformate (500 µL) and stirred a further 4 hours. The mixture was diluted with water (100 mL) and extracted with EtOAc (3×50 mL). The combined organic phases were washed with saturated NaHCO3 (50 mL) and brine (50 mL) then dried over Na₂SO₄, filtered and concentrated under vacuum. The residue was purified by silica column chromatography eluting with 4:1 hexanes/EtOAc to afford the title compound (1.83 g, 62% yield) as a white powder.

Intermediate 17

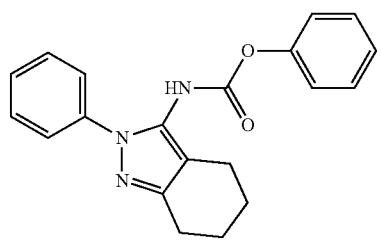 [SMILES: O=C(Nc1c2c(nn1-c1ccccc1)CCCC2)Oc1ccccc1]

2-phenyl-4,5,6,7-tetrahydro-2H-indazol-3-amine

Prepared according to the method of Intermediate 7, substituting 2-methyl-3-oxobutanenitrile with 2-oxocyclohexanecarbonitrile to yield the title compound (738 mg, 94% yield) as a pale orange solid. MS (apci) m/z=214.1 (M+H).

Intermediate 18 phenyl (2-phenyl-4,5,6,7-tetrahydro-2H-indazol-3-yl)carbamate

Prepared according to the method of Intermediate 8, substituting 3,4-dimethyl-1-phenyl-1H-pyrazol-5-amine with 2-phenyl-4,5,6,7-tetrahydro-2H-indazol-3-amine. MS (apci) m/z=334.1 (M+H).

Intermediate 19

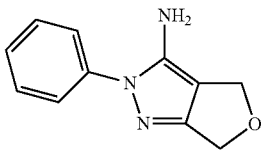 [SMILES: Nc1c2c(nn1-c1ccccc1)COC2]

2-phenyl-4,6-dihydro-2H-furo[3,4-c]pyrazol-3-amine

Step A: Preparation of 4-oxotetrahydrofuran-3-carbonitrile: To a suspension of KOtBu (996.6 mg, 8.881 mmol) in THF (640.4 mg, 8.881 mmol) cooled to 0° C. was added dropwise methyl 2-hydroxyacetate (675.7 μL, 8.881 mmol) and stirred for 10 minutes. Acrylonitrile (589.1 μL, 8.881 mmol) was then added and the reaction stirred at ambient temperature. After 3 hours, the reaction was diluted with $H_2O$ (50 mL), then extracted with $Et_2O$ (25 mL). The basic aqueous phase was acidified with 2M HCl (5 mL), then extracted with $Et_2O$ (2×50 mL). The combined organic phases were dried with $MgSO_4$, filtered and concentrated to afford 4-oxotetrahydrofuran-3-carbonitrile (446 mg, 45.2% yield) as a light brown oil. $^1$H NMR ($CDCl_3$) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine: Prepared according to the method of Intermediate 7, substituting 2-methyl-3-oxobutanenitrile with 4-oxotetrahydrofuran-3-carbonitrile to yield the title compound (182 mg, 22.5% yield) as a reddish-brown syrup. MS (apci) m/z=202.1 (M+H).

Intermediate 20

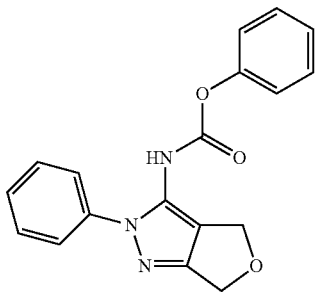 [SMILES: O=C(Nc1c2c(nn1-c1ccccc1)COC2)Oc1ccccc1]

phenyl (2-phenyl-4,6-dihydro-2H-furo[3,4-c]pyrazol-3-yl)carbamate

Prepared according to the method of Intermediate 8, substituting 3,4-dimethyl-1-phenyl-1H-pyrazol-5-amine with 2-phenyl-4,6-dihydro-2H-furo[3,4-c]pyrazol-3-amine. MS (apci) m/z=322.1 (M+H).

Intermediate 21

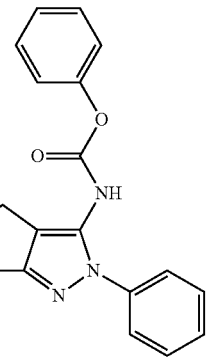

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine:

A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL). The solid was collected by filtration, washed with 0.1 N NaOH, water, and hexanes (approx. 10 mL each) then dried under vacuum to yield 2-phenyl-4,6-dihydro-2H-thieno[3,4-c]pyrazol-3-amine (1.6 g, 95% yield) as a white solid. MS (apci pos) m/z=218.1 (M+H).

Step B: Preparation of phenyl 2-phenyl-4,6-dihydro-2H-thieno[3,4-c]pyrazol-3-ylcarbamate. To a suspension of 2-phenyl-4,6-dihydro-2H-thieno[3,4-c]pyrazol-3-amine (500 mg, 2.30 mmol) in EtOAc (10 mL) was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with $H_2O$, brine (25 mL each), then dried with $Na_2SO_4$, filtered and concentrated. The crude material was purified by reverse-phase column chromatography, eluting with 5-70% acetonitrile/water to yield phenyl 2-phenyl-4,6-dihydro-2H-thieno[3,4-c]pyrazol-3-ylcarbamate (0.5 g, 64% yield) as a white solid. MS (apci pos) m/z=338.1 (M+H).

Step C: Preparation of phenyl (5,5-dioxido-2-phenyl-4,6-dihydro-2H-thieno[3,4-c]pyrazol-3-yl)carbamate. To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 minutes. The mixture was then diluted with DCM (3 mL) and washed with saturated aqueous $NaHCO_3$ (3×2 mL) and saturated aqueous $Na_2S_2O_3$ (3×2 mL). The organic layer was dried with $MgSO_4$, filtered and concentrated under vacuum to yield the title compound (31 mg, 57% yield) as a light yellow foamy solid. MS (apci pos) m/z=371.0 (M+H).

Intermediate 22

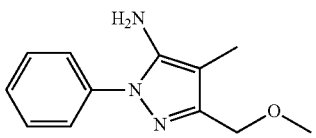

3-(methoxymethyl)-4-methyl-1-phenyl-1H-pyrazol-5-amine

Step A: Preparation of 4-methoxy-2-methyl-3-oxobutanenitrile: To a solution of methyl 2-methoxyacetate (0.48 mL, 4.80 mmol) in THF (20 mL, 4.803 mmol) at −78° C. under $N_2$ were added propiononitrile (317.4 mg, 5.76 mmol) then lithium bis(trimethylsilyl)amide (4.8 mL, 1M/THF, 4.8 mmol). The mixture was stirred for 1 hour, then at 0° C. for 1 hour and was diluted with $H_2O$ (25 mL) and extracted with $Et_2O$ (25 mL) The basic aqueous phase was neutralized with 2M HCl (2.0 mL), then extracted with $Et_2O$ (2×25 mL). The combined organic phases were washed with brine (25 mL), dried over $MgSO_4$, filtered and concentrated under vacuum to afford 4-methoxy-2-methyl-3-oxobutanenitrile (247 mg, 40% yield) as a pale yellow oil.

Step B: Preparation of 3-(methoxymethyl)-4-methyl-1-phenyl-1H-pyrazol-5-amine: Prepared according to the method of Intermediate 7, substituting 2-methyl-3-oxobutanenitrile with 4-methoxy-2-methyl-3-oxobutanenitrile to yield the title compound (96 mg, 23% yield) as an orange gum. MS (apci) m/z=218.0 (M+H).

Intermediate 23

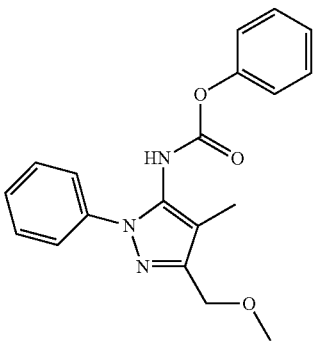 [SMILES: COCc1nn(-c2ccccc2)c(NC(=O)Oc2ccccc2)c1C]

phenyl (3-(methoxymethyl)-4-methyl-1-phenyl-1H-pyrazol-5-yl)carbamate

Prepared according to the method of Intermediate 8, substituting 3,4-dimethyl-1-phenyl-1H-pyrazol-5-amine with 3-(methoxymethyl)-4-methyl-1-phenyl-1H-pyrazol-5-amine. MS (apci) m/z=337.9 (M+H).

Intermediate 24

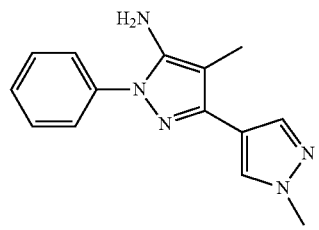 [SMILES: Cc1c(-c2cnn(C)c2)nn(-c2ccccc2)c1N]

1',4-dimethyl-1-phenyl-1H,1'H-3,4'-bipyrazol-5-amine

Step A: ethyl 1-methyl-1H-pyrazole-4-carboxylate: To a 3000-mL three-necked flask was added ethyl 2-formyl-3-oxopropanoate (100 g, 694 mmol), followed by anhydrous 200-proof EtOH (694 mL). The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature for 16 hours. The reaction was concentrated under vacuum and the residue dissolved in DCM and re-concentrated, then dried for 2 days to yield ethyl 1-methyl-1H-pyrazole-4-carboxylate (106 g, 99% yield) as a tan orange oil. MS (apci) m/z=155.1 (M+H).

Step B: 2-methyl-3-(1-methyl-1H-pyrazol-4-yl)-3-oxopropanenitrile: To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) using a dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise using an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbonate solution The aqueous layer was extracted with DCM (3×1000 mL). The combined organic extracts were dried over $MgSO_4$ filtered and concentrated to yield 2-methyl-3-(1-methyl-1H-pyrazol-4-yl)-3-oxopropanenitrile as an amber oil (92 g, 82% yield). MS (apci) m/z=162.1 (M−H).

Step C: 1',4-dimethyl-1-phenyl-1H,1'H-3,4'-bipyrazol-5-amine: A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected by filtration, washed with hexanes and dried under vacuum to provide the title compound (93 g, 100% yield) as a yellow solid. MS (apci) m/z=254.1 (M+H).

Intermediate 25

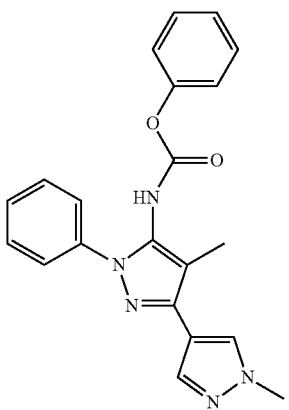 [SMILES: Cc1c(-c2cnn(C)c2)nn(-c2ccccc2)c1NC(=O)Oc1ccccc1]

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated under vacuum. The residue was purified by silica column chromatography eluting with 75% EtOAc/hexanes to provide the title compound (60 g, 81% yield) as a cream foam. MS (apci) m/z=374.1 (M+H).

Intermediate 26

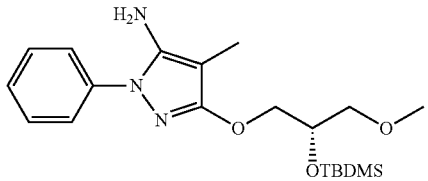 [SMILES: COC[C@@H](COc1nn(-c2ccccc2)c(N)c1C)O[Si](C)(C)C(C)(C)C]

(S)-3-(2-((tert-butyldimethylsilyl)oxy)-3-methoxypropoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol: A mixture of 5-amino-4-methyl-1-phenyl-1H-pyrazol-3(2H)-one (P135 Step A, 1.21 g, 6.40 mmol) and powdered $K_2CO_3$ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled $H_2O$ (25 mL) and extracted with EtOAc (3×). The combined extracts were washed with saturated NaCl (2×), dried over $MgSO_4$ and filtered through a $SiO_2$ plug capped with a layer of $MgSO_4$ eluting with EtOAc. The filtrate was concentrated to give the title compound as a colorless, viscous oil (701 mg, 40% yield). MS (apci) m/z=278.1 (M+H).

Step B: (S)-3-(2-(((tert-butyldimethylsilyl)oxy)-3-methoxypropoxy)-4-methyl-1-phenyl-1H-pyrazol-5-amine: To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to $H_2O$ (70 mL), mixed for 5 minutes and extracted with $Et_2O$ (3×). The combined extracts were washed with saturated NaCl (2×) and dried over $MgSO_4$. The dried solution was filtered through a $SiO_2$ plug capped with a layer of $MgSO_4$ ($Et_2O$ elution). The filtrate was concentrated to give the title compound as a colorless oil that was dried in vacuum (940 mg, 105%). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 27

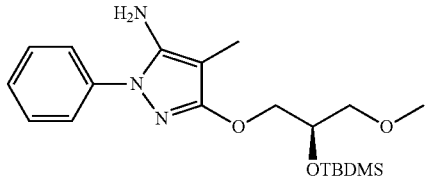 [SMILES: COC[C@H](COc1nn(-c2ccccc2)c(N)c1C)O[Si](C)(C)C(C)(C)C]

(R)-3-(2-(((tert-butyldimethylsilyl)oxy)-3-methoxypropoxy)-4-methyl-1-phenyl-1H-pyrazol-5-amine The title compound was prepared using the procedure described for (S)-3-(2-(((tert-butyldimethylsilyl)oxy)-3-methoxypropoxy)-4-methyl-1-phenyl-1H-pyrazol-5-amine (Intermediate 14) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 28

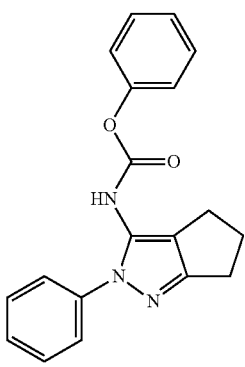 [SMILES: O=C(Nc1c2c(nn1-c1ccccc1)CCC2)Oc1ccccc1]

phenyl (2-phenyl-2,4,5,6-tetrahydrocyclopenta[c]pyrazol-3-yl)carbamate

To a suspension of 2-phenyl-2,4,5,6-tetrahydrocyclopenta[c]pyrazol-3-amine (100 mg, 0.50 mmol) in EtOAc (2 mL) was added 2 M NaOH (0.50 mL, 1.0 mmol) followed by phenyl chloroformate (88 µL, 0.70 mmol). The mixture was stirred vigorously at ambient temperature for 16 hours them partitioned between EtOAc (10 mL) and water (10 mL). The aqueous layer was extracted with EtOAc (2×10 mL) and the combined organic phases were washed with brine (10 mL), dried over $Na_2SO_4$, filtered and concentrated under vacuum. The residue was purified by silica column chromatography eluting with 0-1% MeOH/DCM then again with 4:1 hexanes/EtOAc to afford the title compound (63 mg, 39% yield) as a white foam. MS (apci) m/z=320.1 (M+H).

Intermediate 29

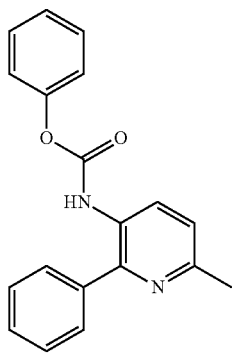 [SMILES: Cc1ccc(NC(=O)Oc2ccccc2)c(-c2ccccc2)n1]

phenyl (6-methyl-2-phenylpyridin-3-yl)carbamate

Step A: Preparation of 6-methyl-2-phenylpyridin-3-amine: Phenyl boronic acid (424 mg, 3.48 mmol), $K_2CO_3$ (1.48 g, 10.7 mmol) and $Pd(PPh_3)_4$ (309 mg, 0.27 mmol) were combined in toluene (6 mL), water (3 mL) and EtOH (1.5 mL) then treated with 2-bromo-6-methylpyridin-3-amine (500 mg, 2.67 mmol). The mixture was warmed to 95° C. in a sealed tube for 16 hours then cooled and partitioned between EtOAc (30 mL) and saturated $NH_4Cl$ (30 mL). The aqueous layer was extracted with EtOAc (2×30 mL) and the combined organic phases were washed with brine (30 mL), dried over $Na_2SO_4$, filtered and concentrated under vacuum. The residue was purified by silica column chromatography eluting with 4:1 hexanes/EtOAc to afford 6-methyl-2-phenylpyridin-3-amine (407 mg, 83% yield) as a pale yellow crystalline solid. MS (apci) m/z=185.1 (M+H).

Step B: Preparation of phenyl (6-methyl-2-phenylpyridin-3-yl)carbamate: To a solution of 6-methyl-2-phenylpyridin-3-amine (407 mg, 2.21 mmol) in EtOAc (10 mL) was added 2N NaOH (2.21 mL, 4.42 mmol) followed by phenyl chloroformate (388 µL, 3.09 mmol). The mixture was stirred at ambient temperature for 4 hours then diluted with water (50 mL) and extracted with EtOAc (3×20 mL). The combined organic phases were washed with saturated $NaHCO_3$ (20 mL) and brine (20 mL) then dried over $Na_2SO_4$, filtered and concentrated to afford the title compound (665 mg, 99% yield) as a white crystalline solid. MS (apci) m/z=305.1 (M+H).

Intermediate 30

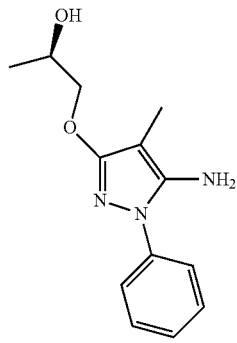 [SMILES: Cc1c(OC[C@@H](C)O)nn(-c2ccccc2)c1N]

(R)-1-((5-amino-4-methyl-1-phenyl-1H-pyrazol-3-yl)oxy)propan-2-ol

A mixture of 5-amino-4-methyl-1-phenyl-1H-pyrazol-3(2H)-one [Intermediate 27, Step A] (1.0 g, 5.3 mmol), (R)-2-methyloxirane (0.40 g, 6.9 mmol) and $K_2CO_3$ (1.8 g, 13 mmol) in DMA (10 mL) was heated at 80° C. for 48 hours. After cooling the reaction mixture was treated with EtOAc, washed with water and brine, dried with $MgSO_4$, and filtered through a pad of silica gel with EtOAc elution. The filtrate was concentrated to afford the title compound (660 mg, 46% yield). MS (apci) m/z=248.1 (M+H).

Intermediate 31

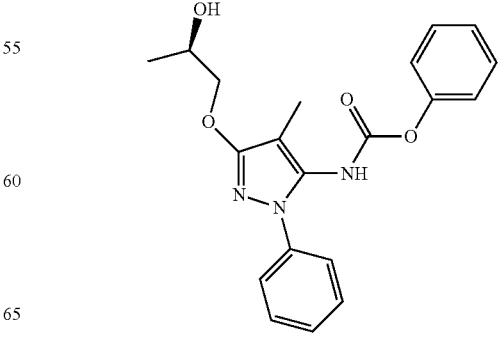

(R)-phenyl (3-(2-hydroxypropoxy)-4-methyl-1-phenyl-1H-pyrazol-5-yl)carbamate To a suspension of (R)-1-(5-amino-4-methyl-1-phenyl-1H-pyrazol-3-yloxy) propan-2-ol [Intermediate 37] (660 mg, 2.46 mmol) in EtOAc (7 mL) at 0° C. was added NaOH (3.07 mL, 2M, 6.14 mmol) and phenyl carbonochloridate (0.47 mL, 3.68 mmol). The reaction was stirred at ambient temperature for 3 days then treated with EtOAc, washed with water and brine, dried over $MgSO_4$, filtered and concentrated under vacuum. The residue was purified by silica column chromatography eluting with 3:1 hexanes/EtOAc to afford the title compound (463 mg 51% yield). MS (apci) m/z=368.1 (M+H).

Preparation A1

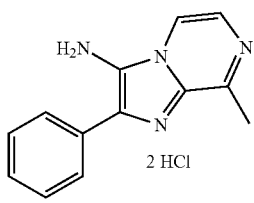 [SMILES: Cc1nccn2c(N)c(-c3ccccc3)nc12]

2 HCl

8-methyl-2-phenylimidazo[1,2-a]pyrazin-3-aminedihydrochloride

Step A: Preparation of 8-methyl-2-phenyl-N-(2,4,4-trimethylpentan-2-yl) imidazo[1,2-a]pyrazin-3-amine: To a solution of 3-methylpyrazin-2-amine (4.00 g, 36.7 mmol) and benzaldehyde (4.08 mL, 40.33 mmol) in 2:1 DCM-MeOH (100 mL) was added $Sc(OTf)_3$ (0.902 g, 1.83 mmol) and the mixture was stirred at ambient temperature for 30 minutes. 2-Isocyano-2,4,4-trimethylpentane (8.52 mL, 44.0 mmol) was added and the mixture stirred at ambient temperature for 60 hours. The mixture was concentrated and the residue was purified by silica column chromatography eluting with a step gradient of DCM, 20% then 50% EtOAc/hexanes. The title compound was obtained as a white solid (9.80 g, 80% yield). $^1$H NMR ($CDCl_3$) δ 8.03 (d, J=4.6 Hz, 1H), 7.82 (d, J=8.3 Hz, 2H), 7.74 (d, J=4.6 Hz, 1H), 7.46 (t, 2H), 7.35 (m, 1H), 3.28 (br s, 1H), 2.91 (s, 3H), 1.55 (s, 2H), 1.02 (s, 9H), 0.94 (s, 6H) ppm.

Step B: Preparation of 8-methyl-2-phenylimidazo[1,2-a]pyrazin-3-aminedihydrochloride: To a solution of 8-methyl-2-phenyl-N-(2,4,4-trimethylpentan-2-yl) imidazo[1,2-a]pyrazin-3-amine (9.20 g, 27.3 mmol) in MeOH (60 mL) at 0° C. was added 4M HCl/dioxane (150 mL) and the mixture was stirred at ambient temperature for 2.5 hours. The mixture was diluted with MTBE (500 mL), stirred for 5 minutes and the precipitate was collected, washed with MTBE and dried under vacuum to afford the title compound (8.40 g, 103% yield) as an orange powder. $^1$H NMR (DMSO$d_6$) δ 8.58 (d, J=5.6 Hz, 1H), 8.01 (d, J=8.4 Hz, 2H), 7.74 (d, J=5.6 Hz, 1H), 7.55 (t, J=7.5 Hz, 2H), 7.46 (t, J=7.4 Hz, 1H), 2.89 (s, 3H) ppm.

The compounds of Table 3 were prepared according to the method of Preparation A1 using the appropriate 2-amino-1-azaheterocycle and aldehyde.

TABLE 3

| Compound | Structure | Name | Data |
|---|---|---|---|
| A2 | 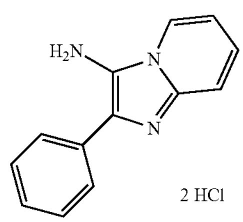 [SMILES: Nc1c(-c2ccccc2)nc2ccccn12] | 2-phenylimidazo[1,2-a]pyridin-3-amine hydrochloride | MS(apci) m/z = 210.3 (M + H) |
| A3 | 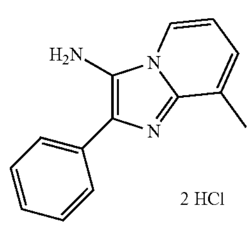 [SMILES: Cc1cccn2c(N)c(-c3ccccc3)nc12] | 8-methyl-2-phenylimidazo[1,2-a]pyridin-3-amine dihydrochloride | MS(apci) m/z = 224.3 (M + H) |
| A4 | 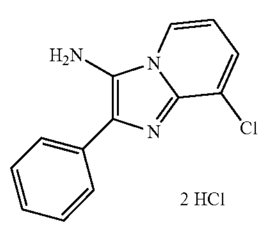 [SMILES: Nc1c(-c2ccccc2)nc2c(Cl)cccn12] | 8-chloro-2-phenylimidazo[1,2-a]pyridin-3-amine dihydrochloride | MS(apci) m/z = 244.2 (M + H) |

TABLE 3-continued

| Compound | Name | Data |
|---|---|---|
| A5 | 8-trifluoromethyl-2-phenylimidazo[1,2-a]pyridin-3-amine dihydrochloride | MS(apci) m/z = 278.0 (M + H) |
| A6 | 8-fluoro-2-phenylimidazo[1,2-a]pyridin-3-amine dihydrochloride | $^1$H NMR (DMSOd$_6$) δ 8.75 (d, J = 6.8 Hz, 1H), 7.96 (d, J = 7.3 Hz, 2H), 7.75 (dd, J = 10.5, 8.0 Hz, 1H), 7.57 (t, J = 7.4 Hz, 2H), 7.48-7.41 (m, 2H) ppm. |
| A7 | 8-bromo-2-phenylimidazo[1,2-a]pyridin-3-amine dihydrochloride | MS(apci) m/z = 290.0 (M + H) |
| A8 | 2-(3-fluorophenyl)-8-(trifluoromethyl)imidazo[1,2-a]pyridin-3-amine dihydrochloride | MS(apci) m/z = 296.0 (M + H) |
| A9 | 2-(4-fluorophenyl)-8-(trifluoromethyl)imidazo[1,2-a]pyridin-3-amine dihydrochloride | MS(apci) m/z = 296.1 (M + H) |
| A10 | 2-(4-methoxyphenyl)-8-methylimidazo[1,2-a]pyridin-3-amine dihydrochloride | MS(apci) m/z = 254.1 (M + H) |

TABLE 3-continued

| Compound | Structure | Name | Data |
|---|---|---|---|
| A11 | 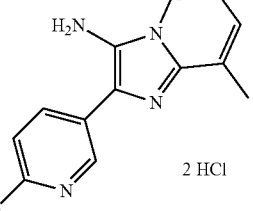 | 2-(6-methoxypyridin-3-yl)-8-methylimidazo[1,2-a]pyridin-3-amine dihydrochloride | MS(apci) m/z = 255.1 (M + H) |

Table 1 provides a list of commercially available pyrazole intermediates can be used in the synthesis of compounds described in the Examples.

TABLE 1

| Pyrazole | Vendor/Catalog # | CAS # |
|---|---|---|
| 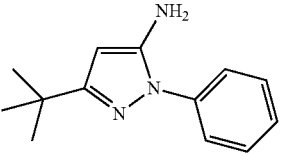 [SMILES: CC(C)(C)c1cc(N)n(-c2ccccc2)n1] | Oakwood, 021512 | 126208-61-5 |
| 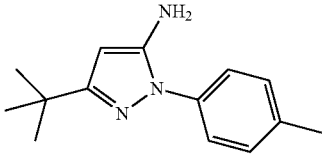 [SMILES: Cc1ccc(-n2nc(C(C)(C)C)cc2N)cc1] | Array BioPharma, A1075-0 | N/A |
| 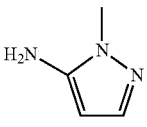 | Maybridge, GK03066 | 1192-21-8 |
| 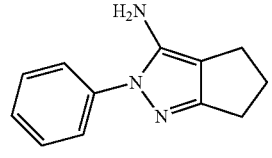 [SMILES: Nc1c2c(nn1-c1ccccc1)CCC2] | Ryan Scientific, EN300-14400 | 89399-92-8 |
| 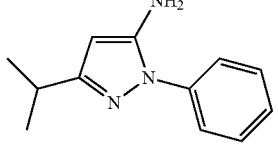 | Oakwood, 021516 | N/A |
| 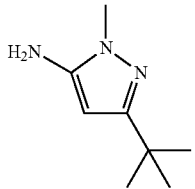 | Alfa Aesar, AAB20095-06 | 118430-73-2 |

TABLE 1-continued

| Pyrazole | Vendor/Catalog # | CAS # |
|---|---|---|
| (1,3-dimethyl-1H-pyrazol-5-amine) | Aldrich, 532223 | 3524-32-1 |
| (3-tert-butyl-1-(pyridin-3-yl)-1H-pyrazol-5-amine) | Accela ChemBio Chem Co, SY003755 | 876299-97-7 |
| (3-tert-butyl-1-(4-fluorophenyl)-1H-pyrazol-5-amine) | ChemImpex, 18122 | 778611-16-8 |
| (3-cyclopropyl-1-phenyl-1H-pyrazol-5-amine) | Oakwood, 017105 | 175137-45-8 |
| (1,3-diphenyl-1H-pyrazol-5-amine) | Alfa Aesar, AAB20464-06 | 5356-71-8 |
| (3-methyl-1-phenyl-1H-pyrazol-5-amine) | Aldrich, 541001 | 1131-18-6 |
| (1-methyl-3-phenyl-1H-pyrazol-5-amine) | Alfa Aesar, AAA15754-06 | 10199-50-5 |
| (1-phenyl-1H-pyrazol-5-amine) | TCI America, A0174 | 826-85-7 |
| (3-tert-butyl-1-(2-fluorophenyl)-1H-pyrazol-5-amine) | Oakwood, 023890 | N/A |

TABLE 1-continued

| Pyrazole | Vendor/Catalog # | CAS # |
|---|---|---|
| 1-(3-fluorophenyl)-3-tert-butyl-5-amino-pyrazole | J&W Pharmalab, 68-0035S | 1187931-80-1 |
| 3-cyclopentyl-1-phenyl-5-amino-pyrazole | VWR, EN300-09508 | N/A |
| 2-methyl-2,4,5,6-tetrahydrocyclopenta[c]pyrazol-3-amine | ChemBridge, 4019184 | 885529-68-0 |
| 1,3-dimethyl-4-phenyl-5-amino-pyrazole | ChemBridge, 4001950 | N/A |
| 1-(2-methylphenyl)-3-tert-butyl-5-amino-pyrazole | ChemImpex, 19156 | 337533-96-7 |
| 1-(3-methylphenyl)-3-tert-butyl-5-amino-pyrazole | ChemImpex, 19155 | 898537-77-4 |
| 1-methyl-3-phenyl-4-amino-pyrazole | ChemBridge, 4006072 | N/A |
| 5-amino-1-phenyl-3-methyl-4-cyano-pyrazole | Oakwood, 005982 | 5346-56-5 |
| 5-amino-1-phenyl-3-trifluoromethyl-pyrazole | ChemImpex, 18771 | 182923-55-3 |

TABLE 1-continued
| Pyrazole | Vendor/Catalog # | CAS # |
|---|---|---|
| 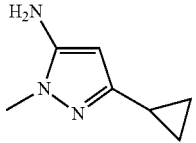 | Maybridge, KM00278 | 118430-74-3 |
| 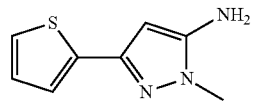 | Maybridge, KM00835 | 118430-78-7 |
| 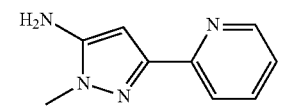 | ChemBridge, 4015288 | N/A |
| 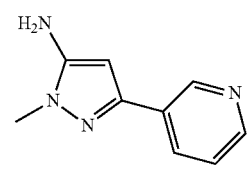 | ChemBridge, 4015289 | N/A |
| 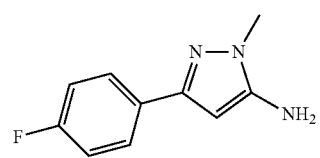 | Matrix, 020274 | N/A |
| 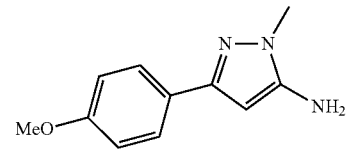 | Matrix, 019183 | N/A |
| 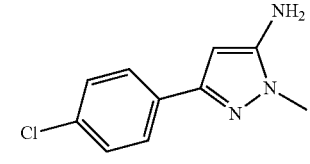 | Maybridge, KM 04038 | 126417-82-1 |
| 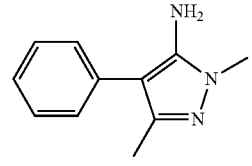 | ChemBridge, 4001950 | N/A |
| 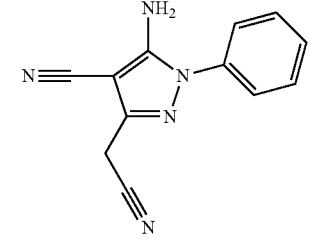 [SMILES: N#CCc1nn(-c2ccccc2)c(N)c1C#N] | Lancaster, AAA17470-06 | 7152-40-1 |

TABLE 1-continued

| Pyrazole | Vendor/Catalog # | CAS # |
|---|---|---|
| | ChemBridge, 4010196 | 91642-97-6 |
| | VWR, AAA13296-14 | 16078-71-0 |

N/A = Not available

Intermediate P1

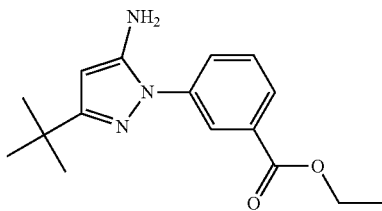 [SMILES: CCOC(=O)c1cccc(-n2nc(C(C)(C)C)cc2N)c1]

Ethyl 3-(5-amino-3-tert-butyl-1H-pyrazol-1-yl)benzoate

To a suspension of ethyl 3-hydrazinylbenzoate hydrochloride (500 mg, 2.31 mmol) in EtOH (20 mL) was added 4,4-dimethyl-3-oxopentanenitrile (318 mg, 2.54 mmol). The reaction mixture was heated to reflux for 18 hours, then cooled to ambient temperature and concentrated in vacuo. The crude product was purified by silica column chromatography, eluting with 0-5% MeOH/DCM to yield the product as a yellow oil (154 mg, 23% yield). MS (apci) m/z=288.2 (M+H).

The compounds in Table 2 were prepared by the method as described for Intermediate P1, substituting 4,4-dimethyl-3-oxopentanenitrile with the appropriate cyanoketone and ethyl 3-hydrazinylbenzoate hydrochloride with the appropriate hydrazine.

TABLE 2

| Intermediate # | Structure | Data |
|---|---|---|
| P2 | 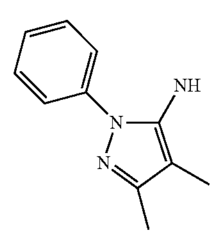 | MS (apci) m/z = 188.2 (M + H) |
| P3 | 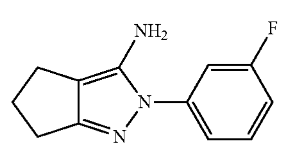 [SMILES: Nc1c2c(nn1-c1cccc(F)c1)CCC2] | MS (apci) m/z = 218.1 (M + H) |
| P4 | 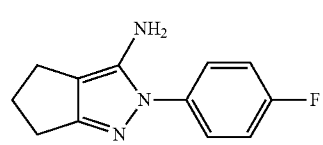 [SMILES: Nc1c2c(nn1-c1ccc(F)cc1)CCC2] | MS (apci) m/z = 218.2 (M + H) |

TABLE 2-continued
| Intermediate # | Structure | Data |
|---|---|---|
| P5 | 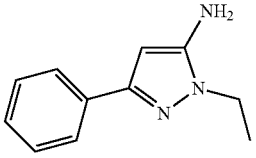 | MS (apci) m/z = 188.2 (M + H) |
| P6 | 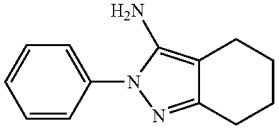 [SMILES: Nc1c2c(nn1-c1ccccc1)CCCC2] | MS (apci) m/z = 214.2 (M + H) |
| P7 | 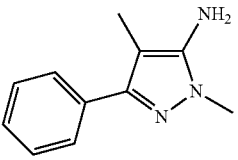 | MS (apci) m/z = 188.2 (M + H) |
| P8 | 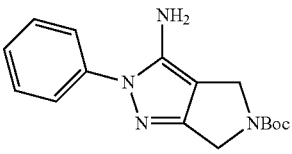 [SMILES: CC(C)(C)OC(=O)N1Cc2nn(-c3ccccc3)c(N)c2C1] | MS (apci) m/z = 301.0 (M + H) |
| P9 | 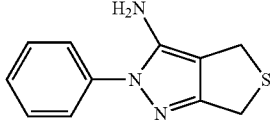 [SMILES: Nc1c2c(nn1-c1ccccc1)CSC2] | MS (apci) m/z = 218.1 (M + H) |
| P10 | 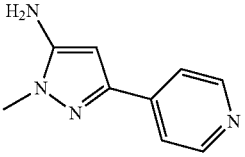 | MS (apci) m/z = 175.2 (M + H) |
| P11 | 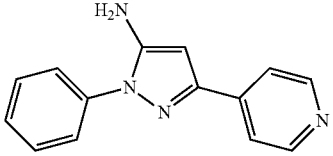 [SMILES: Nc1cc(-c2ccncc2)nn1-c1ccccc1] | MS (apci) m/z = 237.3 (M + H) |
| P12 | 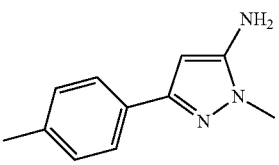 | MS (apci) m/z = 188.2 (M + H) |
| P13 | 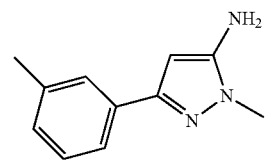 | MS (apci) m/z = 188.2 (M + H) |

TABLE 2-continued

| Intermediate # | Structure | Data |
| --- | --- | --- |
| P14 | 3-(2-methylphenyl)-1-methyl-1H-pyrazol-5-amine | MS (apci) m/z = 188.2 (M + H) |
| P15 | 3-(3-methoxyphenyl)-1-methyl-1H-pyrazol-5-amine | MS (apci) m/z = 204.2 (M + H) |
| P16 | 3-(2-methoxyphenyl)-1-methyl-1H-pyrazol-5-amine | MS (apci) m/z = 204.2 (M + H) |
| P17 | 3-(3-cyanophenyl)-1-methyl-1H-pyrazol-5-amine | MS (apci) m/z = 199.0 (M + H) |
| P18 | 3-(4-cyanophenyl)-1-methyl-1H-pyrazol-5-amine | MS (apci) m/z = 199.1 (M + H) |
| P19 | 3-(3-fluorophenyl)-1-methyl-1H-pyrazol-5-amine | MS (apci) m/z = 192.2 (M + H) |
| P20 | 3-(2-fluorophenyl)-1-methyl-1H-pyrazol-5-amine | MS (apci) m/z = 192.2 (M + H) |
| P21 | methyl 4-(5-amino-1-methyl-1H-pyrazol-3-yl)benzoate | MS (apci) m/z = 232.2 (M + H) |
| P22 | 1-(2-hydroxyethyl)-3-phenyl-1H-pyrazol-5-amine | MS (apci) m/z = 204.2 (M + H) |
| P23 | 2-cyclohexyl-2,4,5,6-tetrahydrocyclopenta[c]pyrazol-3-amine | MS (apci) m/z = 206.1 (M + H) |

Intermediate P101

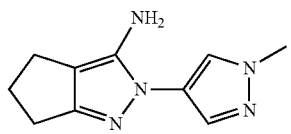

2-(1-methyl-1H-pyrazol-4-yl)-2,4,5,6-tetrahydrocyclopenta-[c]pyrazol-3-amine

Step A: Preparation of di-tert-butyl 1-(1-methyl-1H-pyrazol-4-yl)hydrazine-1,2-dicarboxylate: To a solution of 4-bromo-1-methyl-1H-pyrazole (1.93 mL, 18.6 mmol) in ether (37.3 mL) cooled to −78° C. was added nBuLi (23.3 mL, 37.3 mmol). After stirring at −78° C. for 30 minutes, a solution of di-t-butyl azodicarboxylate (4.29 g, 18.6 mmol) in Et$_2$O (37.3 mL, 18.6 mmol) was added dropwise. After 1 hour, the reaction mixture was warmed up to −20° C. and quenched with ice. After warming to ambient temperature, the mixture was filtered and rinsed with Et$_2$O. The resulting solid was taken up in a mixture of DCM and water, and the mixture was phase separated. The organic layer was dried with MgSO$_4$, filtered and concentrated in vacuo to afford the first batch of product as a white solid (1.64 g, 28% yield). A second batch of product was recovered from the filtrate by silica column chromatography, eluting with 40-60% hexanes/EtOAc (0.51 g, 8.8% yield). MS (apci) m/z=313.0 (M+H).

Step B: Preparation of 2-(1-methyl-1H-pyrazol-4-yl)-2,4,5,6-tetrahydrocyclopenta[c]pyrazol-3-amine: To a solution of di-tert-butyl 1-(1-methyl-1H-pyrazol-4-yl)hydrazine-1,2-dicarboxylate (103 mg, 0.330 mmol) in EtOH (1.65 mL, 0.330 mmol) was added concentrated HCl (137 µL, 1.65 mmol). The mixture was stirred at ambient temperature for 5 minutes, then cooled in an ice bath followed by addition of 2-oxocyclopentanecarbonitrile (36.0 mg, 0.330 mmol). After stirring for 5 minutes, the reaction mixture was warmed to ambient temperature overnight. The reaction mixture was concentrated and partitioned in water and DCM. After phase-separation, the aqueous layer was basified (pH 10) and then extracted with DCM (3×10 mL). The combined organic extracts were dried with MgSO$_4$, filtered and concentrated in vacuo. The crude material was purified by reverse-phase column chromatography, eluting with 0-100% acetonitrile/water to afford the product as a yellow solid (4.5 mg, 6.7% yield). MS (apci) m/z=204.1 (M+H).

Intermediate P102

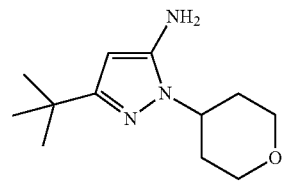 [SMILES: CC(C)(C)c1cc(N)n(C2CCOCC2)n1]

3-tert-butyl-1-(tetrahydro-2H-pyran-4-yl)-1H-pyrazol-5-amine

Step A: Preparation of (tetrahydro-2H-pyran-4-yl)hydrazine hydrochloride: A suspension of dihydro-2H-pyran-4 (3H)-one (2.00 g, 20.0 mmol) and tert-butyl hydrazinecarboxylate (2.64 g, 20.0 mmol) in hexanes (20.0 mL) was refluxed for 2 hours. After cooling, BH$_3$-THF complex (20.0 mL, 20.0 mmol) was added and the reaction mixture was stirred for 1 hour. The mixture was then treated with 4 N HCl in dioxane (20.0 mL, 79.9 mmol), followed by 3 drops of water. After stirring at ambient temperature for 1 hour, the reaction mixture was filtered and rinsed with EtOAc to afford the product as a solid (2.39 g, 78.4% yield). MS (apci) m/z=117.0 (M+H).

Step B: Preparation of 3-ten-butyl-1-(tetrahydro-2H-pyran-4-yl)-1H-pyrazol-5-amine: Prepared by the method as described in for the preparation of Intermediate P1, substituting (tetrahydro-2H-pyran-4-yl)hydrazine dihydrochloride for ethyl 3-hydrazinylbenzoate hydrochloride to yield the product as a yellow oil (0.472 g, 99.9% yield). MS (apci) m/z=224.1 (M+H).

Intermediate P103

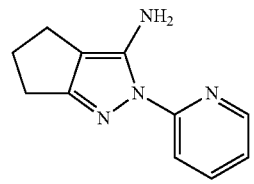 [SMILES: Nc1c2c(nn1-c1ccccn1)CCC2]

2-(pyridin-2-yl)-2,4,5,6-tetrahydrocyclopenta[c]pyrazol-3-amine

Step A: Preparation of 2-(2-(pyridin-2-yl)hydrazono)cyclopentanecarbonitrile: A solution of 2-hydrazinylpyridine (0.200 g, 1.83 mmol) and 2-oxocyclopentanecarbonitrile (0.200 g, 1.83 mmol) in MeOH (9.16 mL) was treated with concentrated HCl (0.764 mL, 9.16 mmol) and refluxed for 16 hours. The reaction mixture was concentrated in vacuo, and then partitioned in water and DCM. After phase-separation, the aqueous layer was washed with DCM, basified (saturated NaHCO$_3$, pH 10), and extracted with DCM. The combined organic layers were dried with MgSO$_4$, filtered and concentrated. The crude material was purified by silica column chromatography, eluting with 100% EtOAc to afford the product (0.289 g, 78.6% yield). MS (apci) m/z=201.2 (M+H).

Step B: Preparation of 2-(pyridin-2-yl)-2,4,5,6-tetrahydrocyclopenta[c]pyrazol-3-amine: A solution of 2-(2-(pyridin-2-yl) hydrazono)cyclopentanecarbonitrile (0.243 g, 1.21 mmol) in EtOH (6.06 mL, 1.21 mmol) was treated with 6 M HCl (0.202 mL, 1.21 mmol) and refluxed for 3 days. After removal of the solvent, the crude residue was diluted in water, basified (saturated NaHCO$_3$, pH 10) and extracted with DCM. The combined organic layers were dried with MgSO$_4$, filtered and concentrated. The crude material was purified by silica column chromatography, eluting with 50% EtOAc/hexanes to afford the product (0.198 g, 81.6% yield). MS (apci) m/z=201.2 (M+H).

Intermediate P104

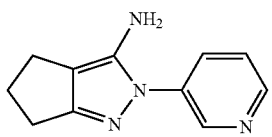 [SMILES: Nc1c2c(nn1-c1cccnc1)CCC2]

2-(pyridin-3-yl)-2,4,5,6-tetrahydrocyclopenta[c]pyrazol-3-amine

Prepared by the method described above for Intermediate P103, substituting 3-hydrazinylpyridine for 2-hydrazinyl pyridine to afford the title product. MS (apci) m/z=201.1 (M+H).

Intermediate P105

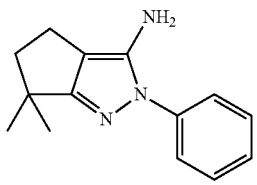 [SMILES: CC1(C)CCc2c1nn(-c1ccccc1)c2N]

6,6-dimethyl-2-phenyl-2,4,5,6-tetrahydrocyclopenta[c]pyrazol-3-amine

Step A: Preparation of 5-chloro-2,2-dimethylpentanenitrile: Isobutyronitrile (1.38 g, 20.0 mmol) and 1-bromo-3-chloropropane (3.46 g, 22.0 mmol) were sequentially added to a 1 M solution of lithium bis(trimethylsilyl)amide (20.0 mL, 20.0 mmol) while stirring. After stirring at 70° C. for 16 hours, the reaction mixture was quenched with water then extracted with DCM. The combined organic layers were dried with MgSO$_4$, filtered and concentrated in vacuo to afford 5-chloro-2,2-dimethylpentanenitrile (2.91 g, 100% yield). $^1$H NMR (CDCl$_3$) δ 3.57-3.61 (m, 2H), 1.94-2.02 (m, 2H), 1.67-1.72 (m, 2H), 1.37 (s, 6H).

Step B: Preparation of 2,2-dimethylhexanedinitrile: A suspension of 5-chloro-2,2-dimethylpentanenitrile (2.91 g, 20.0 mmol) and NaCN (1.57 g, 32.0 mmol) in DMF (20.0 mL) and water (1 mL) was heated at 100° C. for 16 hours. After cooling, the reaction mixture was diluted with water and refluxed for 30 minutes, then cooled, poured into water and stirred for 3 hours. The solution was then extracted with Et$_2$O. The combined Et$_2$O extracts were washed with H$_2$O, dried with MgSO$_4$, filtered and concentrated in vacuo to afford the product (2.20 g, 80.7% yield). $^1$H NMR (CDCl$_3$) δ 2.42-2.47 (m, 2H), 1.83-1.92 (m, 2H), 1.67-1.72 (m, 2H), 1.39 (s, 6H).

Step C: Preparation of 3,3-dimethyl-2-oxocyclopentanecarbonitrile: A suspension of KOtBu (0.511 g, 4.55 mmol) in toluene (18.4 mL) was treated a toluene (2.0 mL) solution of 2,2-dimethylhexanedinitrile (1.00 g, 7.34 mmol) and heated at 80° C. for 2 hours. The reaction mixture was then cooled to ambient temperature and quenched with water. The mixture was separated and the organic layer was stirred in 2 N HCl (20 mL) for 16 hours. The mixture was separated and the organic layer dried with MgSO$_4$, filtered and concentrated in vacuo to a yellow-white solid. The crude solid was purified by silica column chromatography, eluting with 10-40% EtOAc/hexanes, to afford the product (0.250 g, 24.8% yield). $^1$H NMR (CDCl$_3$) δ 3.20-3.26 (m, 1H), 2.38-2.47 (m, 1H), 2.14-2.25 (m, 1H), 1.97-2.05 (m, 1H), 1.74-1.83 (m, 1H), 1.14 (s, 6H).

Step D: Preparation of 6,6-dimethyl-2-phenyl-2,4,5,6-tetrahydrocyclopenta[c]pyrazol-3-amine: Prepared by the method as described for Intermediate P1, substituting phenylhydrazine for ethyl 3-hydrazinylbenzoate hydrochloride and 3,3-dimethyl-2-oxocyclopentanecarbonitrile for 4,4-dimethyl-3-oxopentanenitrile to afford the product (0.192 g, 46.2% yield) as a yellow solid. MS (apci) m/z=228.2 (M+H).

Intermediate P106

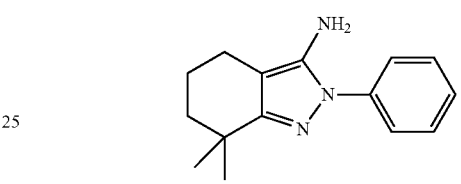

7,7-dimethyl-2-phenyl-4,5,6,7-tetrahydro-2H-indazol-3-amine

Step A: Preparation of 2,2-dimethylheptanedinitrile: Prepared by the method as described for Intermediate P105, Steps A and B, substituting 1-bromo-4-chlorobutane for 1-bromo-3-chloropropane to yield the product (2.21 g, 73.7% yield). $^1$H NMR (CDCl$_3$) δ 2.37-2.42 (m, 2H), 1.53-1.77 (m, 6H), 1.36 (s, 6H).

Step B: Preparation of 3,3-dimethyl-2-oxocyclohexanecarbonitrile: A suspension of KOtBu (0.463 g, 4.13 mmol) in toluene (16.6 mL) was treated with a solution of 2,2-dimethylheptanedinitrile (1.00 g, 6.66 mmol) in toluene (2.0 mL) and heated at 80° C. for 48 hours. After cooling to ambient temperature, the reaction mixture was quenched with water and phase-separated, and the organic layer was stirred with 2 N HCl (20 mL) for 16 hours. After phase-separation, the organic layer was dried with MgSO$_4$, filtered and concentrated in vacuo. The crude material was purified by silica column chromatography, eluting with 10-20% EtOAc/hexanes to afford the product (0.374 g, 37.2% yield). $^1$H NMR (CDCl$_3$) δ 3.72-3.78 (m, 1H), 2.42-2.50 (m. 1H), 1.78-2.04 (m, 4H), 1.60-1.70 (m, 1H), 1.21 (s, 3H), 1.16 (s, 3H).

Step C: Preparation of 7,7-dimethyl-2-phenyl-4,5,6,7-tetrahydro-2H-indazol-3-amine: Prepared by the method as described for Intermediate P1, substituting phenylhydrazine for ethyl 3-hydrazinylbenzoate hydrochloride and 3,3-dimethyl-2-oxocyclohexanecarbonitrile for 4,4-dimethyl-3-oxopentanenitrile to yield the product as an off-white solid (0.490 g, 54.2% yield, 66% purity). MS (apci) m/z=242.2 (M+H).

Intermediate P107

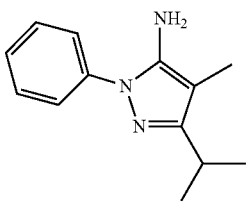 [SMILES: Cc1c(C(C)C)nn(-c2ccccc2)c1N]

3-isopropyl-4-methyl-1-phenyl-1H-pyrazol-5-amine

Step A: Preparation of 2,4-dimethyl-3-oxopentanenitrile: To a solution of propiononitrile (518 mg, 9.40 mmol) in THF (50 mL, 7.83 mmol) at −78° C. under $N_2$ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with $H_2O$ (50 mL) to dissolve the solids. The mixture was extracted with $Et_2O$ (25 mL), and the basic aqueous phase was acidified with 2M HCl (5 mL) and extracted with $Et_2O$ (2×50 mL). The combined organic phases were washed with brine (50 mL), dried with $MgSO_4$, filtered, and concentrated to afford the product (421 mg, 42.9% yield)

Step B: Preparation of 3-isopropyl-4-methyl-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

Intermediate P108

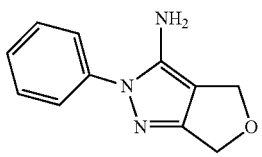 [SMILES: Nc1c2c(nn1-c1ccccc1)COC2]

2-phenyl-4,6-dihydro-2H-furo[3,4-c]pyrazol-3-amine

Step A: Preparation of 4-oxotetrahydrofuran-3-carbonitrile: To a suspension of KOtBu (996.6 mg, 8.881 mmol) in THF (640.4 mg, 8.881 mmol) cooled to 0° C. was added dropwise methyl 2-hydroxyacetate (675.7 μL, 8.881 mmol) and stirred for 10 minutes. The acrylonitrile (589.1 μL, 8.881 mmol) was then added and the reaction stirred at ambient temperature. After 3 hours, the reaction was diluted with $H_2O$ (50 mL), then extracted with $Et_2O$ (25 mL) to remove any starting ester. The basic aqueous phase was acidified with 2M HCl (5 mL), then extracted with $Et_2O$ (2×50 mL). The combined organic phases were dried with $MgSO_4$, filtered, and concentrated to afford a light brown oil (446 mg, 45.2% yield). $^1$H NMR ($CDCl_3$) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine: Prepared by the method as described for Intermediate P1, substituting phenyl hydrazine for ethyl 3-hydrazinylbenzoate hydrochloride and 4,4-dimethyl-3-oxopentanenitrile with 4-oxotetrahydrofuran-3-carbonitrile to yield the product as a reddish-brown syrup (182 mg, 22.5% yield). MS (apci) m/z=202.1 (M+H).

Intermediate P109

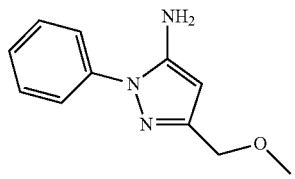

3-(methoxymethyl)-1-phenyl-1H-pyrazol-5-amine

Step A: Preparation of 4-methoxy-3-oxobutanenitrile: To a solution of methyl 2-methoxyacetate (0.4753 mL, 4.803 mmol) in THF (20 mL, 4.803 mmol) at −78° C. under $N_2$ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with $H_2O$ (25 mL), washed with $Et_2O$ (25 mL), then neutralized with 2 M HCl (1.5 mL). This was extracted with $Et_2O$ (2×25 mL) and the combined organic phases were washed with brine (25 mL), dried with $MgSO_4$, filtered, and concentrated to afford the product (169 mg, 31.1% yield). $^1$H NMR ($CDCl_3$) δ 4.09 (s, 2H), 3.66 (s, 2H), 3.46 (s, 3H)

Step B: Preparation of 3-(methoxymethyl)-1-phenyl-1H-pyrazol-5-amine: Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

Intermediate P110

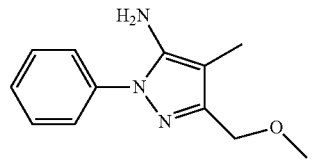 [SMILES: COCc1nn(-c2ccccc2)c(N)c1C]

3-(methoxymethyl)-4-methyl-1-phenyl-1H-pyrazol-5-amine

Prepared according to the method as described for Intermediate P109, replacing acetonitrile with propionitrile to afford the product as an orange residue. MS (apci) m/z=218.0 (M+H).

Intermediate P111

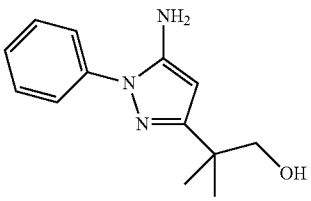 [SMILES: CC(C)(CO)c1cc(N)n(-c2ccccc2)n1]

2-(5-amino-1-phenyl-1H-pyrazol-3-yl)-2-methylpropan-1-ol

Step A: Preparation of methyl 3-(tert-butyldimethylsilyloxy)-2,2-dimethylpropanoate: Methyl 3-hydroxy-2,2-dimethylpropanoate (1.000 g, 7.567 mmol), TBDMS-Cl (1.140 g, 7.567 mmol) and imidazole (0.5666 g, 8.323 mmol) were dissolved in DMF (5 mL, 7.567 mmol) and stirred at ambient temperature overnight. The reaction mixture was diluted with $H_2O$ (25 mL) and extracted with EtOAc (2×25 mL). The combined organic phases were washed with brine (25 mL), dried with $MgSO_4$, filtered and concentrated to afford the product (1.92 g, 103% yield). $^1$H NMR ($CDCl_3$) δ 3.66 (s, 3H), 3.57 (s, 2H), 1.15 (s, 6H), 0.87 (s, 9H), 0.02 (s, 6H).

Step B: Preparation of 5-(tert-butyldimethylsilyloxy)-4,4-dimethyl-3-oxopentanenitrile: Prepared according to the method described for Intermediate P109, replacing methyl 2-methoxyacetate with methyl 3-(tert-butyldimethylsilyloxy)-2,2-dimethylpropanoate to afford the product as a pale yellow residue. $^1$H NMR ($CDCl_3$) δ 3.70 (s, 2H), 3.55 (s, 2H), 1.15 (s, 6H), 0.89 (s, 9H), 0.06 (s, 6H).

Step C: Preparation of 2-(5-amino-1-phenyl-1H-pyrazol-3-yl)-2-methylpropan-1-ol: Prepared by the method as described for Intermediate P1, substituting phenyl hydrazine for ethyl 3-hydrazinylbenzoate hydrochloride and 4,4-dimethyl-3-oxopentanenitrile with methyl 3-(tert-butyldimethylsilyloxy)-2,2-dimethylpropanoate to yield the product as yellow syrup (74 mg, 66% yield). MS (apci) m/z=232.2 (M+H).

Intermediate P112

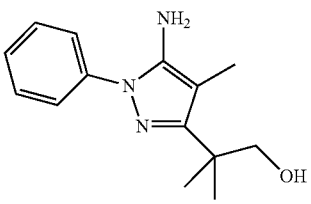 [SMILES: Cc1c(C(C)(C)CO)nn(-c2ccccc2)c1N]

2-(5-amino-4-methyl-1-phenyl-1H-pyrazol-3-yl)-2-methylpropan-1-ol

Prepared according to the method described for Intermediate P111, replacing acetonitrile with propionitrile to afford the product as a yellow residue. MS (apci) m/z=246.2 (M+H).

Intermediate P113

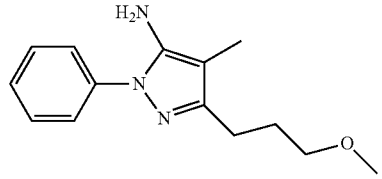 [SMILES: COCCCc1nn(-c2ccccc2)c(N)c1C]

3-(3-methoxypropyl)-4-methyl-1-phenyl-1H-pyrazol-5-amine

Prepared according to the method described for Intermediate P109, replacing methyl 2-methoxyacetate with methyl 4-methoxybutanoate and replacing acetonitrile with propionitrile in Step A to afford the product as an orange-brown syrup. MS (apci) m/z=246.1 (M+H).

Intermediate P114

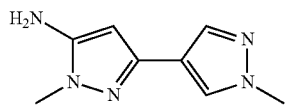

1,1'-dimethyl-1H,1'H-3,4'-bipyrazol-5-amine

Step A: Preparation of 3-(1-methyl-1H-pyrazol-4-yl)-3-oxopropanenitrile: A solution of ethyl 1-methyl-1H-pyrazole-4-carboxylate (500 mg, 3.24 mmol), toluene (7.50 mL, 70.4 mmol), and acetonitrile (346 µL, 6.49 mmol) was treated in one portion with KOtBu (1092 mg, 9.73 mmol) to give a hazy solution. The reaction was allowed to stir at ambient temperature for one hour, and was determined to be complete by HPLC analysis. The mixture was treated with water (7.5 mL) and stirred for 1 minute, then acidified with 3M HCl (3027 µL, 9.08 mmol) to pH 5.5-6. The aqueous layer was extracted with ethyl acetate (3×5 mL) and the combined organic extracts were concentrated in vacuo to give a yellow viscous oil, which completely solidified upon placing under high vacuum to afford the product (102 mg, 21.1% yield). $^1$H NMR ($CDCl_3$) δ 8.02 (s, 1H), 7.94 (s, 1H), 3.98 (s, 3H), 3.82 (s, 2H)

Step B: Preparation of 1,1'-dimethyl-1H,1'H-3,4'-bipyrazol-5-amine: Prepared by the method as described for Intermediate P1, substituting methyl hydrazine for ethyl 3-hydrazinylbenzoate hydrochloride and replacing 4,4-dimethyl-3-oxopentanenitrile with 3-(1-methyl-1H-pyrazol-4-yl)-3-oxopropanenitrile to yield the product as an ivory white solid (45 mg, 44.6% yield). MS (apci) m/z=178.1 (M+H).

Intermediate P115

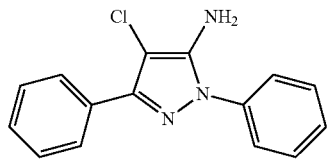 [SMILES: Nc1c(Cl)c(-c2ccccc2)nn1-c1ccccc1]

4-chloro-1,3-diphenyl-1H-pyrazol-5-amine

To a solution of 1,3-diphenyl-1H-pyrazol-5-amine (Table 1; 0.100 g, 0.425 mmol) in acetonitrile (2 mL) was added N-chlorosuccinimide (0.0568 g, 0.425 mmol). The pale yellow solution was stirred at ambient temperature for 3 hours, then concentrated in vacuo and purified by silica column chromatography eluting with 20% EtOAc/Hexanes to afford the product as a light brown oil (0.10 g, 87% yield). MS (apci) m/z=270.0 (M+H).

Intermediate P116

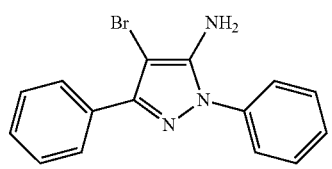 [SMILES: Nc1c(Br)c(-c2ccccc2)nn1-c1ccccc1]

4-bromo-1,3-diphenyl-1H-pyrazol-5-amine

Prepared according to the procedure described for Intermediate P115, substituting N-chloro succinimide with N-bromo-succinimide. MS (apci) m/z=313.9 (M+H).

Intermediate P117

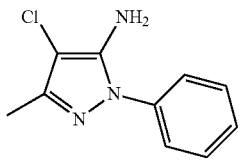

4-chloro-3-methyl-1-phenyl-1H-pyrazol-5-amine

Prepared according to the procedure described for Intermediate P115, substituting 1,3-diphenyl-1H-pyrazol-5-amine with 3-methyl-1-phenyl-1H-pyrazol-5-amine. MS (apci) m/z=207.9 (M+H).

Intermediate P118

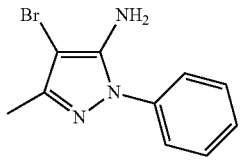

4-bromo-3-methyl-1-phenyl-1H-pyrazol-5-amine

Prepared according to the procedure described for Intermediate P117, substituting N-chloro succinimide with N-bromo-succinimide. MS (apci) m/z=251.9 (M+H).

Intermediate P119

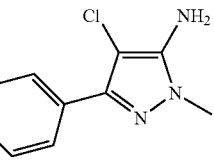

4-chloro-1-methyl-3-phenyl-1H-pyrazol-5-amine

Prepared according to the procedure described for Intermediate P115, substituting 1,3-diphenyl-1H-pyrazol-5-amine with 1-methyl-3-phenyl-1H-pyrazol-5-amine (Table 1). MS (apci) m/z=208.0 (M+H).

Intermediate P120

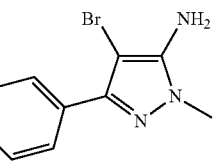

4-bromo-1-methyl-3-phenyl-1H-pyrazol-5-amine

Prepared according to the procedure described for Intermediate P119, substituting N-chloro succinimide with N-bromo-succinimide. MS (apci) m/z=251.9 (M+H).

Intermediate P121

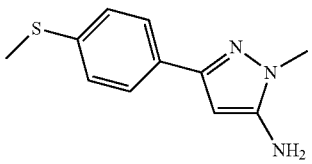

1-methyl-3-(4-(methylthio)phenyl)-1H-pyrazol-5-amine

Step A: Preparation of 3-(4-(methylthio)phenyl)-3-oxo-propanenitrile: To a suspension of NaH (60% in mineral oil) (154 mg, 3.84 mmol) in dioxane (25.0 mL, 2.74 mmol) was added acetonitrile (0.217 mL, 4.12 mmol). The reaction mixture was stirred at ambient temperature for 30 minutes, then treated with methyl 4-(methylthio)benzoate (500 mg, 2.74 mmol) and heated to reflux for 15 hours. The suspension was cooled, then diluted with water (25 mL) and washed with Et$_2$O (25 mL). The aqueous layer was neutralized with 2M HCl (1.8 mL) and extracted with Et$_2$O (2×25 mL). The combined organic phases were washed with brine (25 mL), dried with MgSO$_4$, filtered and concentrated in vacuo. The resultant residue was purified by silica column chromatography eluting with 0-5% MeOH/DCM to afford the product (317 mg, 60.4% yield). ¹H NMR (CDCl₃) δ 7.82 (d, 2H), 7.30 (d, 2H), 4.02 (s, 2H), 2.54 (s, 3H).

Step B: Preparation of 1-methyl-3-(4-(methylthio)phenyl)-1H-pyrazol-5-amine: Prepared by the method as described in Intermediate P1, substituting methylhydrazine for ethyl 3-hydrazinylbenzoate hydrochloride and substituting 3-(4-(methylthio)phenyl)-3-oxopropanenitrile for 4,4-dimethyl-3-oxopentanenitrile to yield the product as a yellow solid (0.307 g, 96.7% yield). MS (apci) m/z=220.0 (M+H).

Intermediate P122

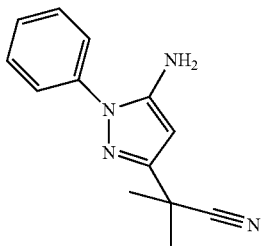 [SMILES: CC(C)(C#N)c1cc(N)n(-c2ccccc2)n1]

2-(5-amino-1-phenyl-1H-pyrazol-3-yl)-2-methylpropanenitrile

Prepared according to the procedure for Intermediate P121, substituting methyl 4-(methylthio)benzoate with ethyl 2-cyano-2-methylpropanoate in Step A and phenyl hydrazine hydrochloride for methyl hydrazine in Step B. MS (apci) m/z=227.1 (M+H).

Intermediate P123

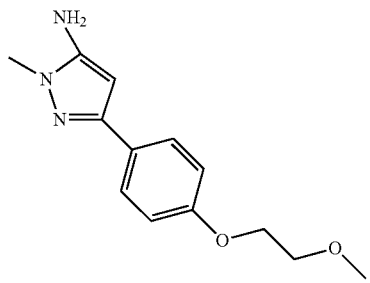

3-(4-(2-methoxyethoxy)phenyl)-1-methyl-1H-pyrazol-5-amine

Step A: Preparation of 3-(4-(benzyloxy)phenyl)-3-oxopropanenitrile: Prepared according to the procedure described for Intermediate P121, substituting methyl 4-(methylthio) benzoate with methyl 4-(benzyloxy)benzoate in Step A. ¹H NMR (CDCl₃) δ 7.90 (d, 2H), 7.42 (m, 4H), 7.37 (m, 1H), 7.05 (d, 2H), 5.16 (s, 2H), 4.00 (s, 2H).

Step B: Preparation of 3-(4-(benzyloxy)phenyl)-1-methyl-1H-pyrazol-5-amine: Prepared by the method as described for Intermediate P1, substituting methylhydrazine for ethyl 3-hydrazinylbenzoate hydrochloride and 3-(4-(benzyloxy)phenyl)-3-oxopropanenitrile for 4,4-dimethyl-3-oxopentanenitrile to yield the product as a yellow solid. MS (apci) m/z=280.1 (M+H).

Step C: Preparation of 4-(5-amino-1-methyl-1H-pyrazol-3-yl)phenol: To a solution of 3-(4-(benzyloxy)phenyl)-1-methyl-1H-pyrazol-5-amine (47 mg, 0.17 mmol) in EtOH (5.0 mL) was added 5% Pd/C (9.0 mg, 0.0084 mmol) and stirred under a H₂ balloon for 17 hours. The reaction mixture was filtered through Celite®, rinsed with EtOH and concentrated in vacuo to afford the product (28 mg, 88% yield). MS (apci) m/z=190.1 (M+H).

Step D: Preparation of 3-(4-(2-methoxyethoxy)phenyl)-1-methyl-1H-pyrazol-5-amine: To a solution of 4-(5-amino-1-methyl-1H-pyrazol-3-yl)phenol (14 mg, 0.074 mmol) in DMSO (0.50 mL, 7.0 mmol) was added Cs₂CO₃ (48 mg, 0.15 mmol) and 1-bromo-2-methoxyethane (9.7 µL, 0.10 mmol). The reaction mixture was stirred for 16 hours, then diluted with water (10 mL) and extracted with DCM (3×10 mL). The combined organic extracts were washed with brine (10 mL), dried with MgSO₄, filtered and concentrated to afford the crude product (22 mg, 120% yield). The crude product was used without purification in subsequent steps. MS (apci) m/z=248.0 (M+H).

Intermediate P124

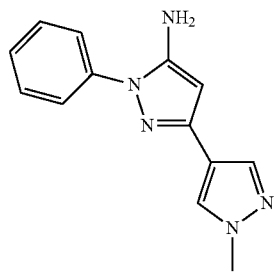 [SMILES: Cn1cc(-c2cc(N)n(-c3ccccc3)n2)cn1]

1'-methyl-1-phenyl-1H,1'H-3,4'-bipyrazol-5-amine

Prepared according to the procedure described for Intermediate P114, substituting methylhydrazine with phenylhydrazine in Step B. MS (apci) m/z=240.0 (M+H).

Intermediate P125

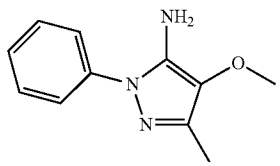

4-methoxy-3-methyl-1-phenyl-1H-pyrazol-5-amine

Prepared according to the procedure for Intermediate P121, substituting methyl 4-(methylthio)benzoate with ethyl acetate and substituting acetonitrile with 2-methoxyacetonitrile in Step A and phenyl hydrazine hydrochloride for methyl hydrazine in Step B. MS (apci) m/z=204.0 (M+H).

Intermediate P126

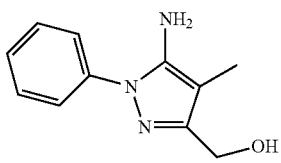

(5-amino-4-methyl-1-phenyl-1H-pyrazol-3-yl)methanol

Prepared according to the procedure for Intermediate P112, substituting methyl 3-hydroxy-2,2-dimethylpropanoate with ethyl 2-hydroxyacetate in Step A. MS (apci) m/z=204.1 (M+H).

Intermediate P127

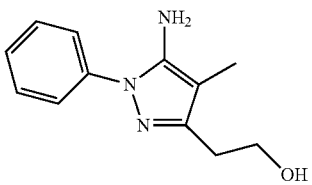 [SMILES: Cc1c(CCO)nn(-c2ccccc2)c1N]

2-(5-amino-4-methyl-1-phenyl-1H-pyrazol-3-yl)ethanol

Prepared according to the procedure for Intermediate P112, substituting methyl 3-hydroxy-2,2-dimethylpropanoate with methyl 3-hydroxypropanoate in Step A. MS (apci) m/z=218.0 (M+H).

Intermediate P128

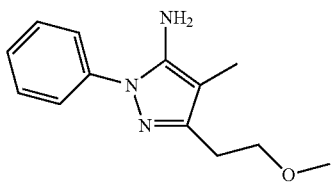 [SMILES: COCCc1nn(-c2ccccc2)c(N)c1C]

3-(2-methoxyethyl)-4-methyl-1-phenyl-1H-pyrazol-5-amine

Step A: Preparation of 5-methoxy-2-methyl-3-oxopentanenitrile: To a suspension of NaNH$_2$ (50 wt % suspension in toluene) (330 mg, 4.23 mmol) in THF (25 mL, 4.23 mmol) under N$_2$ at −78° C. was added propiononitrile (0.448 mL, 6.35 mmol), and the reaction mixture was stirred for 30 minutes. Methyl 3-methoxypropanoate (0.495 mL, 4.23 mmol) was added and the reaction mixture was stirred at −78° C. for 1 hour, then at 0° C. for 2.5 hours. The reaction mixture was diluted with H$_2$O (25 mL) and washed with Et$_2$O (25 mL). The basic aqueous phase was neutralized with 2M HCl (1.6 mL), then extracted with Et$_2$O (3×25 mL). The combined organic phases were washed with brine (25 mL), dried with MgSO$_4$, filtered, and concentrated to afford the crude product as a pale greenish oil (171 mg). The crude mixture was taken directly to the next step.

Step B: Preparation of 3-(2-methoxyethyl)-4-methyl-1-phenyl-1H-pyrazol-5-amine: Prepared by the method as described for Intermediate P1, substituting 5-methoxy-2-methyl-3-oxopentanenitrile for 4,4-dimethyl-3-oxopentanenitrile and substituting phenylhydrazine hydrochloride for ethyl 3-hydrazinylbenzoate hydrochloride to yield the product as a yellow solid (56 mg, 20% yield). MS (apci) m/z=232.0 (M+H).

Intermediate P129

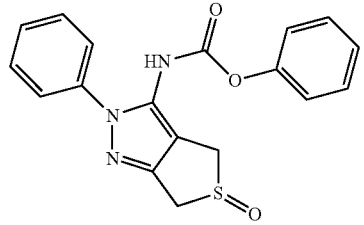 [SMILES: O=C(Nc1c2c(nn1-c1ccccc1)CS(=O)C2)Oc1ccccc1]

Phenyl (5-oxido-2-phenyl-4,6-dihydro-2H-thieno[3,4-c]pyrazol-3-yl)carbamate

A THF (4 mL) solution of phenyl 2-phenyl-4,6-dihydro-2H-thieno[3,4-c]pyrazol-3-ylcarbamate (Intermediate P130, Step B; 50 mg, 0.15 mmol) was cooled to −50° C. with an external dry-ice/MeCN bath and treated with a THF (2 mL) solution of 3-chlorobenzoperoxoic acid (33 mg, 0.13 mmol). After stirring for 1 hour, the mixture was quenched with Na$_2$S$_2$O$_3$ and water, extracted with EtOAc, washed with NaHCO$_3$ and brine, dried with MgSO$_4$, filtered, and concentrated to give the product which was directly used in next step without further purification. MS (apci) m/z=354.1 (M+H).

Intermediate P130

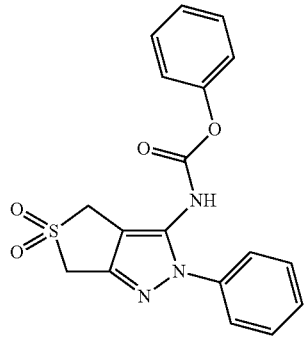 [SMILES: O=C(Nc1c2c(nn1-c1ccccc1)CS(=O)(=O)C2)Oc1ccccc1]

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine: A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL). The solid was collected by filtration, washed with 0.1 N NaOH, water, and hexanes (approx. 10 mL each) then dried on high vacuum to yield the product as white solid (1.6 g, 95% yield). MS (apci pos) m/z=218.1 (M+H).

Step B: Preparation of phenyl 2-phenyl-4,6-dihydro-2H-thieno[3,4-c]pyrazol-3-ylcarbamate: To a suspension of 2-phenyl-4,6-dihydro-2H-thieno[3,4-c]pyrazol-3-amine (500 mg, 2.30 mmol) in EtOAc (10 mL) was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with H₂O, brine (25 mL each), then dried with Na₂SO₄, filtered and concentrated. The crude material was purified by reverse-phase column chromatography, eluting with 5-70% acetonitrile/water to yield the product as white solid (0.5 g, 64% yield). MS (apci pos) m/z=338.1 (M+H).

Step C: Preparation of phenyl (5,5-dioxido-2-phenyl-4,6-dihydro-2H-thieno [3,4-c]pyrazol-3-yl)carbamate: To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 min. The mixture was then diluted with DCM (3 mL) and washed with saturated aqueous NaHCO₃ (3×2 mL) and saturated aqueous Na₂S₂O₃ (3×2 mL). The organic layer was dried with MgSO₄, filtered and concentrated under reduced pressure to yield the title product as light yellowish foamy solid (31 mg, 57% yield, 95% pure). MS (apci pos) m/z=371.0 (M+H).

Intermediate P132

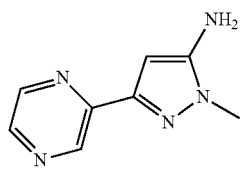

1-methyl-3-(pyrazin-2-yl)-1H-pyrazol-5-amine

Step A: Preparation of 3-oxo-3-(pyrazin-2-yl)propanenitrile: To a suspension of NaH (60% in mineral oil, 81.1 mg, 2.03 mmol) in dioxane (15 mL) was added acetonitrile (0.114 mL, 2.17 mmol), followed by methyl pyrazine-2-carboxylate (200 mg, 1.45 mmol) and the reaction heated to reflux for 2.5 hours. The reaction mixture was cooled to ambient temperature and diluted with H₂O (25 mL) and extracted with Et₂O (25 mL). The aqueous phase was neutralized with 2M aqueous HCl (0.7 mL), then extracted with 10% MeOH/DCM (3×25 mL). The combined organic phases were washed with brine (25 mL), dried with MgSO₄, filtered, and concentrated to yield the crude product as an orange syrup (134 mg, 62.9% yield). ¹H NMR (CDCl₃) δ 9.32 (d, 1H), 8.87 (d, 1H), 8.68 (dd, 1H), 4.34 (s, 2H).

Step B: Preparation of 1-methyl-3-(pyrazin-2-yl)-1H-pyrazol-5-amine: To a suspension of 3-oxo-3-(pyrazin-2-yl)propanenitrile (67.0 mg, 0.455 mmol) in EtOH (5 mL) was added methylhydrazine (0.024 mL, 0.455 mmol). The reaction mixture was refluxed for 15 hours, then concentrated in vacuo. The crude product was purified by silica column chromatography, eluting with 0-5% MeOH/DCM to yield the product as a brown residue (33 mg, 41% yield). MS (apci) m/z=176.2 (M+H).

Intermediate P133

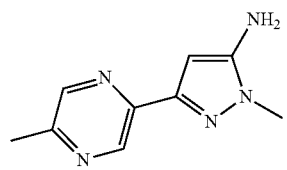

1-methyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate and propionitrile with acetonitrile to afford 3-(5-methylpyrazin-2-yl)-3-oxopropanenitrile. In Step B, phenylhydrazine was replaced by methylhydrazine to afford the title pyrazole. MS (apci) m/z=190.2 (M+H).

Intermediate P134

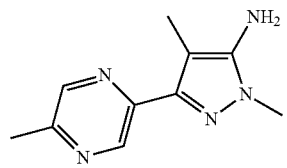

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate P135

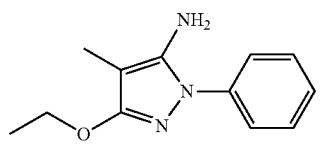 [SMILES: CCOc1nn(-c2ccccc2)c(N)c1C]

3-ethoxy-4-methyl-1-phenyl-1H-pyrazol-5-amine

Step A: Preparation of 5-amino-4-methyl-1-phenyl-1H-pyrazol-3(2H)-one: A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and Et$_2$O. The resultant solid was filtered, washed with Et$_2$O, and dried under vacuum to give the product as a white solid (3.4 g, 39% yield). MS (apci) m/z=190.0 (M−H).

Step B: Preparation of 3-ethoxy-4-methyl-1-phenyl-1H-pyrazol-5-amine To a suspension of 5-amino-4-methyl-1-phenyl-1H-pyrazol-3(2H)-one (10.0 g, 52.9 mmol) in DMF (100 mL) was added K$_2$CO$_3$ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with MgSO$_4$, filtered, and concentrated to give the product (5.35 g, 47% yield). MS (apci) m/z=218.1 (M+H).

The compounds in Table 3 were prepared by the method as described for Intermediate P135, substituting bromoethane with the appropriate alkyl halide or alkyl methanesulfonate.

TABLE 3

| Intermediate # | Structure | Data |
|---|---|---|
| P200 | 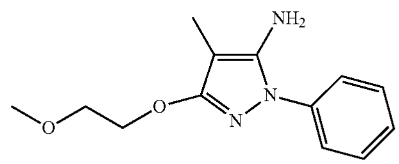 [SMILES: COCCOc1nn(-c2ccccc2)c(N)c1C] | MS (apci) m/z = 248.1 (M + H) |
| P201 | 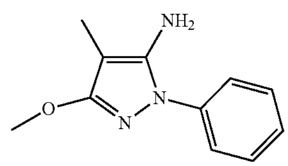 | MS (apci) m/z = 204.1 (M + H) |
| P202 | 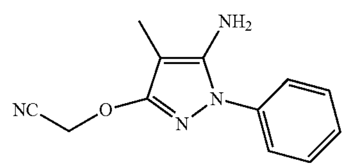 [SMILES: Cc1c(OCC#N)nn(-c2ccccc2)c1N] | MS (apci) m/z = 229.0 (M + H) |
| P203 | 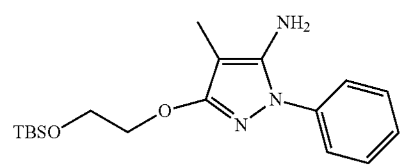 [SMILES: Cc1c(OCCO[Si](C)(C)C(C)(C)C)nn(-c2ccccc2)c1N] | MS (apci) m/z = 348.1 (M + H) |
| P204 | 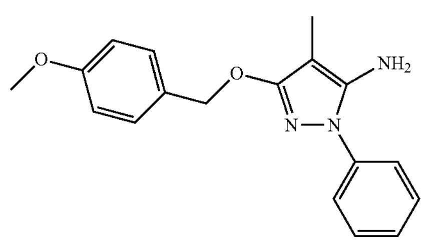 [SMILES: COc1ccc(COc2nn(-c3ccccc3)c(N)c2C)cc1] | MS (apci) m/z = 310.0 (M + H) |
| P205 | 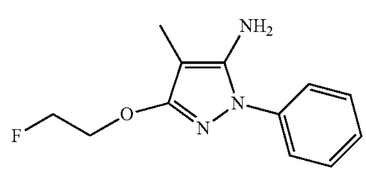 [SMILES: Cc1c(OCCF)nn(-c2ccccc2)c1N] | MS (apci) m/z = 236.1 (M + H) |

TABLE 3-continued

| Intermediate # | Structure | Data |
|---|---|---|
| P206 | 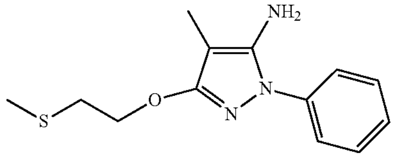 [SMILES: CSCCOc1nn(-c2ccccc2)c(N)c1C] | MS (apci) m/z = 264.0 (M + H) |
| P207 | 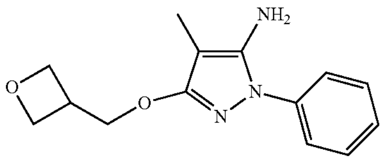 [SMILES: Cc1c(OCC2COC2)nn(-c2ccccc2)c1N] | MS (apci) m/z = 260.1 (M + H) |
| P208 | 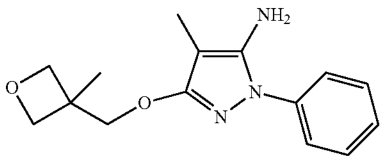 [SMILES: Cc1c(OCC2(C)COC2)nn(-c2ccccc2)c1N] | MS (apci) m/z = 274.1 (M + H) |
| P209 | 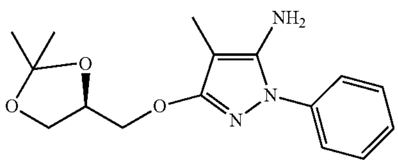 [SMILES: Cc1c(OC[C@H]2COC(C)(C)O2)nn(-c2ccccc2)c1N] | MS (apci) m/z = 304.1 (M + H) |
| P210 | 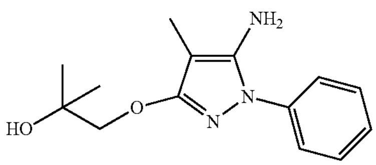 [SMILES: Cc1c(OCC(C)(C)O)nn(-c2ccccc2)c1N] | MS (apci) m/z = 262.1 (M + H) |
| P211 | 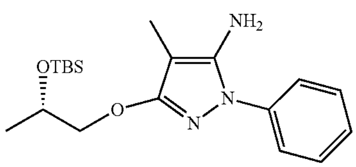 [SMILES: Cc1c(OC[C@H](C)O[Si](C)(C)C(C)(C)C)nn(-c2ccccc2)c1N] | MS (apci) m/z = 362.0 (M + H) |
| P212 | 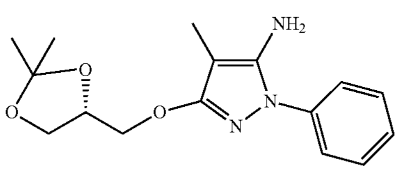 [SMILES: Cc1c(OC[C@@H]2COC(C)(C)O2)nn(-c2ccccc2)c1N] | MS (apci) m/z = 304.1 (M + H) |

Intermediate P136

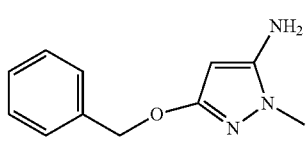

3-(benzyloxy)-1-methyl-1H-pyrazol-5-amine

Step A: Preparation of 5-amino-1-methyl-4-phenyl-1H-pyrazol-3(2H)-one: To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 15 hours. The reaction mixture was cooled to 0° C. and filtered. The resultant solid was washed with cold EtOH (20 mL) and Et$_2$O (20 mL) to give the desired product (2.10 g, 83.7% yield). MS (apci) m/z=190.2 (M+H)

Step B: Preparation of 3-(benzyloxy)-1-methyl-1H-pyrazol-5-amine: A suspension of 5-amino-1-methyl-1H-pyrazol-3(2H)-one (0.35 g, 3.1 mmol), Benzyl chloride (0.43 g, 3.4 mmol), and K$_2$CO$_3$ (1.3 g, 9.3 mmol) in DMF (4 mL) was heated at 70° C. for 17 hours. After cooling, the reaction mixture was treated with EtOAc, washed with water and brine, dried with MgSO$_4$, and concentrated in vacuo. The crude product was purified by silica column chromatography eluting with 2-6% MeOH/DCM to afford the title compound (0.16 g, 25% yield). MS (apci) m/z=204.0 (M+H).

Intermediate P137

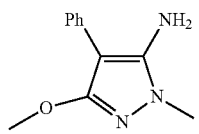

3-methoxy-1-methyl-4-phenyl-1H-pyrazol-5-amine

To a suspension of 5-amino-1-methyl-4-phenyl-1H-pyrazol-3(2H)-one (Step A of the preparation of Intermediate P136; 208 mg, 1.10 mmol) and K$_2$CO$_3$ (456 mg, 3.30 mmol) in DMF (5 mL) was added dropwise iodomethane (172 mg, 1.21 mmol). The reaction mixture was stirred for 15 hours. The solvent was removed under reduced pressure and the residue was purified by silica column chromatography eluting with 33% EtOAc/Hexanes to give the title pyrazole (66.0 mg, 30.4% yield). MS (apci) m/z=204.1 (M+H).

Intermediate P138

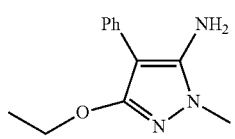 [SMILES: CCOc1nn(C)c(N)c1-c1ccccc1]

3-ethoxy-1-methyl-4-phenyl-1H-pyrazol-5-amine

Prepared as described in Intermediate P137, replacing iodomethane with iodoethane in Step B to afford the title compound. MS (apci) m/z=218.2 (M+H).

Intermediate P139

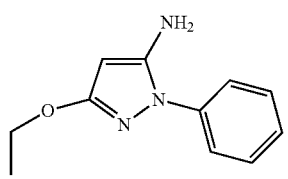

3-ethoxy-1-phenyl-1H-pyrazol-5-amine

Prepared according to the procedure described for Intermediate 135, substituting ethyl-2-cyanopropanoate with ethyl-2-cyanoacetate in Step A. MS (apci) m/z=204.0 (M+H).

The compounds in the following Table were prepared by the method as described for Intermediate P135, substituting bromoethane with the appropriate alkyl halide, alkyl methanesulfonate or epoxide.

| Intermediate # | Structure | MS (apci) m/z |
|---|---|---|
| P140 | 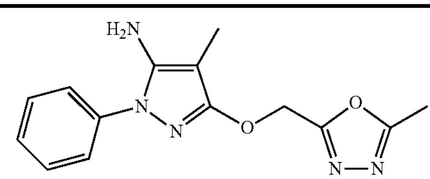 | 286.1 (M + H) |
| P141 | 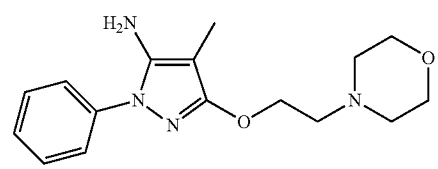 [SMILES: Cc1c(OCCN2CCOCC2)nn(-c2ccccc2)c1N] | 303.1 (M + H) |
| P142 | 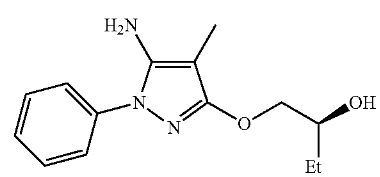 [SMILES: CC[C@H](O)COc1nn(-c2ccccc2)c(N)c1C] | 262.1 (M + H) |
| P143 | 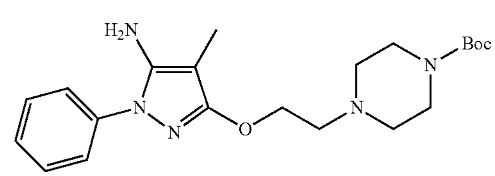 [SMILES: Cc1c(OCCN2CCN(C(=O)OC(C)(C)C)CC2)nn(-c2ccccc2)c1N] | 402.2 (M + H) |

-continued

| Intermediate # | Structure | MS (apci) m/z |
|---|---|---|
| P144 | 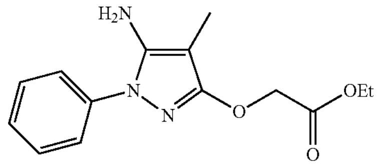 [SMILES: CCOC(=O)COc1nn(-c2ccccc2)c(N)c1C] | 276.1 (M + H) |
| P145 | 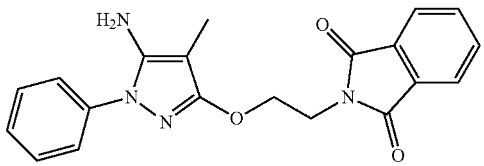 [SMILES: Cc1c(OCCN2C(=O)c3ccccc3C2=O)nn(-c2ccccc2)c1N] | 363.1 (M + H) |
| P146 | 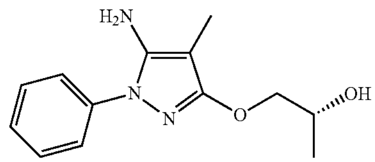 [SMILES: Cc1c(OC[C@@H](C)O)nn(-c2ccccc2)c1N] | 248.1 (M + H) |
| P147 | 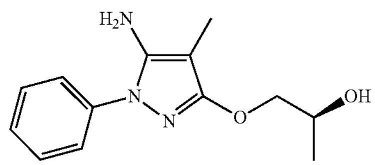 [SMILES: Cc1c(OC[C@H](C)O)nn(-c2ccccc2)c1N] | 248.1 (M + H) |
| P148 | 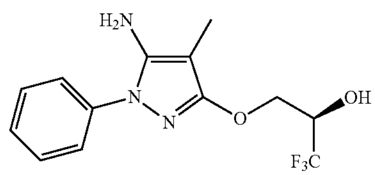 [SMILES: Cc1c(OC[C@@H](O)C(F)(F)F)nn(-c2ccccc2)c1N] | 302.1 (M + H) |
| P149 | 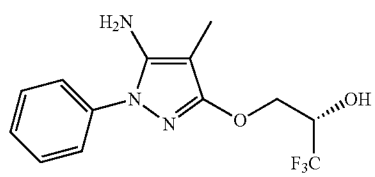 [SMILES: Cc1c(OC[C@H](O)C(F)(F)F)nn(-c2ccccc2)c1N] | 302.1 (M + H) |
| P150 | 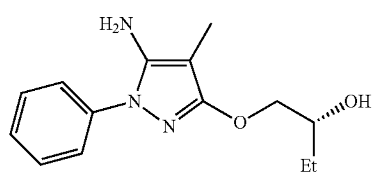 [SMILES: CC[C@@H](O)COc1nn(-c2ccccc2)c(N)c1C] | 262.1 (M + H) |

Intermediate 151

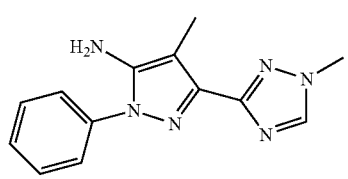 [SMILES: Cc1c(-c2ncn(C)n2)nn(-c2ccccc2)c1N]

1'-(2-methoxyethyl)-1-phenyl-1H,1'H-[3,4'-bipyrazol]-5-amine

Step A: Preparation of methyl 1-methyl-1H-1,2,4-triazole-3-carboxylate: To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H, 1'H-[3,4'-bipyrazol]-5-amine: Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

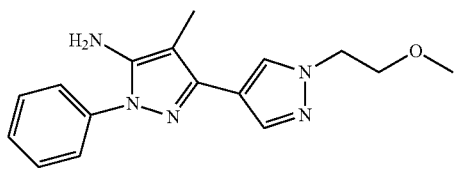 [SMILES: COCCn1cc(-c2nn(-c3ccccc3)c(N)c2C)cn1]

1'-(2-methoxyethyl)-4-methyl-1-phenyl-1H,1'H-[3, 4'-bipyrazol]-5-amine

Prepared according to the method described for Intermediate P109, using ethyl 1-(2-methoxyethyl)-1H-pyrazole-4-carboxylate as a replacement for methyl 2-methoxyacetate, and substituting propionitrile for acetonitrile in Step A.

Intermediate 153

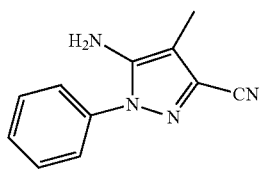

5-amino-4-methyl-1-phenyl-1H-pyrazole-3-carbonitrile

To a stirred solution of aniline (2.02 g, 21.7 mmol) in 6 N HCl (22 mL) was added dropwise a solution of NaNO$_2$ (1.50 g, 21.7 mmol) in water (20 mL) at 0-5° C. The reaction mixture was stirred at 0° C. for 15 minutes. Acetic acid (10 mL) was added. This solution was added dropwise to a stirred solution of ethyl 2,3-dicyanobutanoate (Prepared according to the procedure described in *Bioorganic & Medicinal Chemistry*, 2004, 12, 3345-3356, 3.60 g, 21.7 mmol) in acetic acid (12 mL) and water (18 mL) at 0° C. After stirring for 1 hour, concentrated ammonium hydroxide (50 mL) was added dropwise followed by THF (50 mL). The reaction was stirred at ambient temperature overnight. The organic layer was separated. The aqueous layer was extracted with EtOAc. The combined organic layers were washed with brine, dried and concentrated. The residue was purified by flash chromatography on silica gel (3:1 hexanes/ EtOAc) to give the title compound (2.95 g, 69% yield). MS (apci) m/z=198.9 (M+H).

Intermediate 155

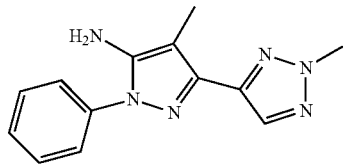 [SMILES: Cc1c(-c2cnn(C)n2)nn(-c2ccccc2)c1N]

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate: A mixture of ethyl 2H-1,2,3-triazole-4-carboxylate (2.00 g, 14.2 mmol), K$_2$CO$_3$ (3.53 g, 25.5 mmol) and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl-1H-pyrazol-5-amine: Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

Intermediate 156

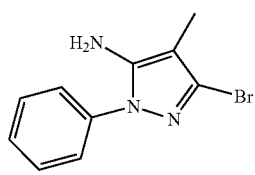

3-bromo-4-methyl-1-phenyl-1H-pyrazol-5-amine

To a stirred solution of 5-amino-4-methyl-1-phenyl-1H-pyrazol-3(2H)-one (Intermediate P135, Step A, 1.00 g, 5.29 mmol) in MeCN (20 mL) was added POBr$_3$ (2.27 g, 7.93 mmol). The reaction mixture was heated at reflux for 3 hours. The reaction was concentrate in vacuo. The residue was taken up in DCM. Saturated aqueous NaHCO$_3$ solution was carefully added. The aqueous layer was extracted with DCM. The combined organic layers were washed with brine, dried and concentrated. The residue was purified by flash chromatography on silica gel (1:2 hexane/EtOAc to give the title compound (0.23 g, 17% yield). MS (apci) m/z=251.8 (M+H).

Intermediate 157

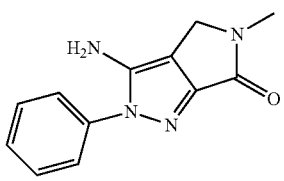 [SMILES: CN1Cc2c(nn(-c3ccccc3)c2N)C1=O]

3-amino-5-methyl-2-phenyl-4,5-dihydropyrrolo[3,4-c]pyrazol-6(2H)-one

Step A: Preparation of ethyl 5-amino-4-((methylamino)methyl)-1-phenyl-1H-pyrazole-3-carboxylate: To a stirred solution of ethyl 5-amino-4-formyl-1-phenyl-1H-pyrazole-3-carboxylate (Prepared according to the procedure described in *J. Heterocyclic Chemistry*, 2010, 47, p. 287-291, 142 mg, 0.548 mmol) in DCM (3 mL) was added 2.0 M MeNH$_2$ in THF (0.822 mL, 1.64 mmol). Two drops of acetic acid was added. The reaction mixture was stirred at ambient temperature overnight. MeOH (0.4 mL) was added followed by NaBH$_4$ (31 mg, 0.82 mmol) portionwise. The reaction was quenched by the slow addition of water. The mixture was extracted with DCM. The combined organic layers were washed with brine, dried and concentrated. The crude was used in the next step without further purification. MS (apci) m/z=275.0 (M+H).

Step B: Preparation of 3-amino-5-methyl-2-phenyl-4,5-dihydropyrrolo[3,4-c]pyrazol-6(2H)-one: To a stirred solution of ethyl 5-amino-4-((methylamino)methyl)-1-phenyl-1H-pyrazole-3-carboxylate (crude, 65 mg, 0.24 mmol) in MeOH (0.5 mL) and THF (0.5 mL) was added 2 N NaOH (0.24 mL, 0.47 mmol). The reaction mixture was stirred at ambient temperature for 4 hours and then concentrated in vacuo. To the residue was added water. The pH was adjusted to 4-5 using 1 N HCl. Water was evaporated under reduced pressure. The crude acid (58 mg) was dissolved in DMF (3 mL). Et$_3$N (66 µL, 0.47 mmol) was added followed by EDCI (90 mg, 0.47 mmol) and HOBt (32 mg, 0.24 mmol). The reaction mixture was stirred at ambient temperature overnight and then partitioned between EtOAc and water. The aqueous layer was extracted with EtOAc. The combined organic layers were washed with water and brine, dried and concentrated. The residue was purified by flash chromatography on silica gel (2% MeOH in DCM) to give the title compound (15 mg, 28%) as a white solid. MS (apci) m/z=228.9 (M+H).

Intermediate 158

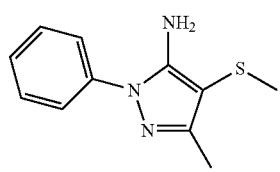

3-methyl-4-(methylthio)-1-phenyl-1H-pyrazol-5-amine

Prepared according to the method described for Intermediate P109, replacing methyl 2-methoxyacetate with ethyl acetate and replacing acetonitrile with 2-(methylthio)acetonitrile in Step A to afford the product as a brown oil. MS (apci) m/z=220.1 (M+H).

Intermediate 159

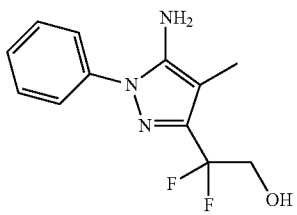 [SMILES: Cc1c(C(F)(F)CO)nn(-c2ccccc2)c1N]

2-(5-amino-4-methyl-1-phenyl-1H-pyrazol-3-yl)-2,2-difluoroethanol

Prepared according to the method described for Intermediate P111, replacing acetonitrile with propionitrile and replacing methyl 3-hydroxy-2,2-dimethylpropanoate with ethyl 2,2-difluoro-3-hydroxypropanoate to afford the product as a pale yellow solid. MS (apci) m/z=254.1 (M+H).

Intermediate 160

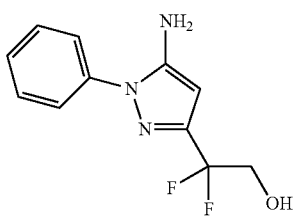 [SMILES: Nc1cc(C(F)(F)CO)nn1-c1ccccc1]

2-(5-amino-1-phenyl-1H-pyrazol-3-yl)-2,2-difluoroethanol

Prepared according to the method described for Intermediate P111, replacing methyl 3-hydroxy-2,2-dimethylpropanoate with ethyl 2,2-difluoro-3-hydroxypropanoate to afford the product as a pale yellow solid. MS (apci) m/z=240.0 (M+H).

Intermediate 161

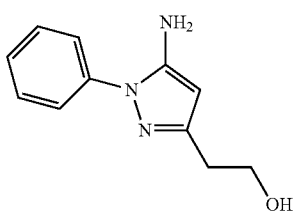 [SMILES: Nc1cc(CCO)nn1-c1ccccc1]

2-(5-amino-1-phenyl-1H-pyrazol-3-yl)ethanol

Prepared according to the method described in Intermediate P111, replacing methyl 3-hydroxy-2,2-dimethylpropanoate with methyl 3-hydroxypropanoate in Step A. MS (apci) m/z=204.1 (M+H).

Intermediate 162

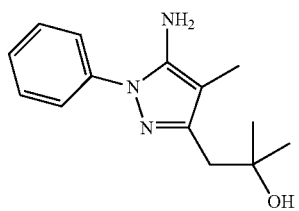 [SMILES: Cc1c(CC(C)(C)O)nn(-c2ccccc2)c1N]

1-(5-amino-4-methyl-1-phenyl-1H-pyrazol-3-yl)-2-methylpropan-2-ol

Step A: Preparation of ethyl 3-hydroxy-3-methylbutanoate: To a solution of lithium bis(trimethylsilyl)amide (1M in THF) (100 mL, 100 mmol) in THF (100 mL) under N₂ and cooled to −78° C. was added ethyl acetate (9.74 mL, 100 mmol). The reaction mixture was stirred for 30 minutes, and then acetone (8.81 mL, 120 mmol) was added. The reaction mixture was stirred for 10 minutes, and then quenched with HCl (2M aqueous, 70 mL, 140 mmol) and allowed to warm to ambient temperature. The reaction mixture was extracted with EtOAc (2×150 mL). The organic phases were combined and washed with saturated aqueous NaHCO₃ (2×50 mL), dried (MgSO₄), filtered and concentrated to afford the product as a yellow oil (12.8 g, 88% yield). $^1$H NMR (CDCl₃) δ 4.18 (q, 3H), 2.49 (s, 2H), 1.29 (m, 9H).

Step B: Preparation of 5-hydroxy-5-methyl-3-oxohexanenitrile: To a solution of propionitrile (1.77 mL, 30.5 mmol) in THF (100 mL) under N₂ at −78° C. was added lithium bis(trimethylsilyl)amide (1M in THF) (27.9 mL, 27.9 mmol). Stirred 1 hour, then ethyl 3-hydroxy-3-methylbutanoate (1.86 g, 12.7 mmol) was added. The reaction mixture was stirred at −78° C. for 1 hour, then stirred at 0° C. for 1.5 hours, then diluted with H₂O (100 mL) and extracted with Et₂O (50 mL). The phases were separated and the basic aqueous phase was neutralized with HCl (6M aqueous, 4.5 mL), then extracted with Et₂O (3×75 mL). The combined organic phases were washed with brine (75 mL), dried (MgSO₄), filtered, and concentrated to afford the product as a pale yellow oil (1.24 g, 63% yield). $^1$H NMR (CDCl₃) δ 3.54 (m, 1H), 2.89 (s, 2H), 1.50 (d, 3H), 1.32 (s, 3H), 1.31 (s, 3H).

Step C: Preparation of 1-(5-amino-4-methyl-1-phenyl-1H-pyrazol-3-yl)-2-methylpropan-2-ol: To a suspension of phenylhydrazine (0.793 mL, 7.99 mmol) and HCl (5-6M in iPrOH, 1.60 mL, 7.99 mmol) in EtOH (25 mL) was added a solution of 5-hydroxy-2,5-dimethyl-3-oxohexanenitrile (1.24 g, 7.99 mmol) in EtOH (25 mL). The reaction mixture was refluxed for 17 hours, then cooled to ambient temperature, diluted with saturated aqueous NaHCO₃ (10 mL), extracted 10:90 MeOH/DCM (3×25 mL), and the combined organic phases were dried (MgSO₄), filtered and concentrated. Purified by silica column chromatography eluting with 0-75% acetone/hexanes to afford the title compound as an orange oil (1.13 g, 58% yield). MS (apci) m/z=246.1 (M+H).

The following pyrazole intermediates were prepared according to the method used for the preparation of Intermediate 162, Steps B and C, using the appropriate starting material. For the preparation of Intermediates 168 and 169, the starting material (purchased from Oakwood) was a mixture of cis and trans diastereomers.

| Intermediate # | Structure | Name | MS (apci) m/z |
|---|---|---|---|
| 163 | 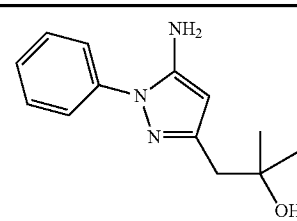 | 1-(5-amino-1-phenyl-1H-pyrazol-3-yl)-2-methylpropan-2-ol | 232.1 (M + H) |
| 164 | 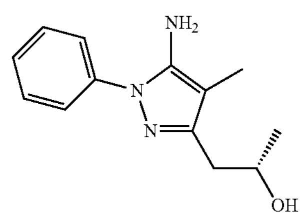 [SMILES: Cc1c(C[C@H](C)O)nn(-c2ccccc2)c1N] | (S)-1-(5-amino-4-methyl-1-phenyl-1H-pyrazol-3-yl)propan-2-ol | 232.1 (M + H) |
| 165 | 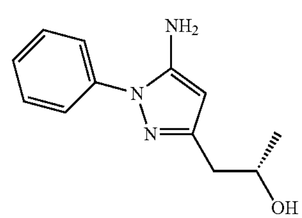 [SMILES: C[C@H](O)Cc1cc(N)n(-c2ccccc2)n1] | (S)-1-(5-amino-1-phenyl-1H-pyrazol-3-yl)propan-2-ol | 218.1 (M + H) |

| Intermediate # | Structure | Name | MS (apci) m/z |
|---|---|---|---|
| 166 | 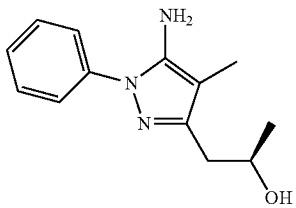 [SMILES: Cc1c(C[C@@H](C)O)nn(-c2ccccc2)c1N] | (R)-1-(5-amino-4-methyl-1-phenyl-1H-pyrazol-3-yl)propan-2-ol | 232.1 (M + H) |
| 167 | 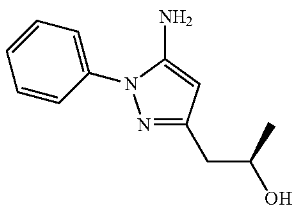 [SMILES: C[C@@H](O)Cc1cc(N)n(-c2ccccc2)n1] | (R)-1-(5-amino-1-phenyl-1H-pyrazol-3-yl)propan-2-ol | 218.1 (M + H) |
| 168 | 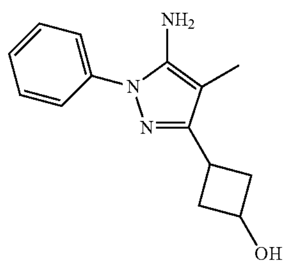 [SMILES: Cc1c(C2CC(O)C2)nn(-c2ccccc2)c1N] | 3-(5-amino-4-methyl-1-phenyl-1H-pyrazol-3-yl)cyclobutanol | 244.1 (M + H) |
| 169 | 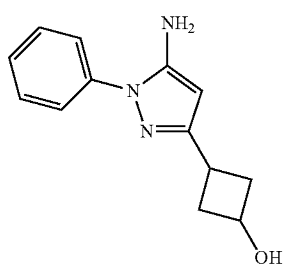 [SMILES: Nc1cc(C2CC(O)C2)nn1-c1ccccc1] | 3-(5-amino-1-phenyl-1H-pyrazol-3-yl)cyclobutanol | 230.1 (M + H) |

Intermediate 170

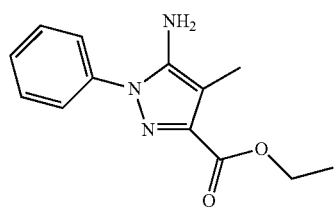 [SMILES: CCOC(=O)c1nn(-c2ccccc2)c(N)c1C]

ethyl 5-amino-4-methyl-1-phenyl-1H-pyrazole-3-carboxylate

Prepared according to the method described for Intermediate P109, replacing methyl 2-methoxyacetate with diethyl oxalate and replacing acetonitrile with propionitrile in Step A to afford the product as a yellow solid. MS (apci) m/z=246.1 (M+H).

Intermediate 171

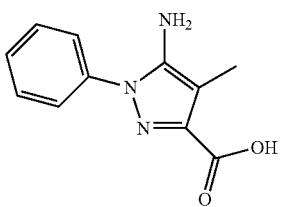 [SMILES: Cc1c(C(=O)O)nn(-c2ccccc2)c1N]

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO₄), filtered and concentrated to give the title compound as a yellow solid (1.3 g, 96% yield) MS (apci) m/z=218.1 (M+H).

Intermediate 172

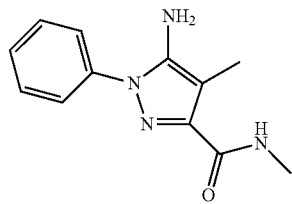 [SMILES: CNC(=O)c1nn(-c2ccccc2)c(N)c1C]

5-amino-N,4-dimethyl-1-phenyl-1H-pyrazole-3-carboxamide

To a solution of 5-amino-4-methyl-1-phenyl-1H-pyrazole-3-carboxylic acid (Intermediate 171, 223 mg, 1.02 mmol) in acetonitrile (10 mL) were added DIEA (0.71 mL, 4.10 mmol), methanamine hydrochloride (138 mg, 2.05 mmol), DMF (2 mL), and then HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

Intermediate 173

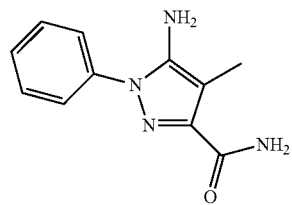 [SMILES: Cc1c(C(N)=O)nn(-c2ccccc2)c1N]

5-amino-4-methyl-1-phenyl-1H-pyrazole-3-carboxamide

A solution of 5-amino-4-methyl-1-phenyl-1H-pyrazole-3-carbonitrile (150 mg, 0.757 mmol) in concentrated H₂SO₄ (0.5 mL) was stirred at ambient temperature for 17 hours. The reaction mixture was cooled and neutralized by the addition of aqueous NaOH (2M, 11 mL), then extracted 10% MeOH/DCM (5×10 mL), and the combined organic extracts were washed with brine, dried (MgSO₄), filtered and concentrated under reduced pressure to afford the title compound as a white solid (151 mg, 95% yield). MS (apci) m/z=239.1 (M+Na).

Intermediate 174

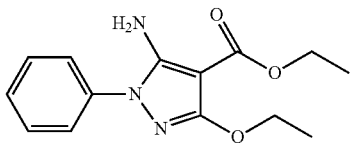 [SMILES: CCOC(=O)c1c(OCC)nn(-c2ccccc2)c1N]

ethyl 5-amino-3-ethoxy-1-phenyl-1H-pyrazole-4-carboxylate

Step A: Preparation of diethyl 2-cyanomalonate: To a suspension of NaH (60 wt % in mineral oil, 499 mg, 12.49 mmol) in THF (100 mL) under N₂ at 0° C. was added diethyl malonate (1.90 mL, 12.49 mmol). The ice bath was removed and the reaction mixture was stirred at ambient temperature for 30 minutes, then cooled to 0° C. and cyanic bromide (5M in MeCN, 2.5 mL, 12.49 mmol) was added. The reaction mixture was stirred at ambient temperature for 19 hours, then diluted with H₂O (50 mL), extracted with Et₂O (50 mL). The aqueous phase was neutralized with HCl (2M aq, 3 mL) then extracted with DCM (2×50 mL). The combined DCM extracts were dried (MgSO₄), filtered, and concentrated to afford the product as a yellow oil (837 mg, 36% yield). 1H NMR (CDCl₃) δ 4.46 (s, 1H), 4.35 (q, 4H), 1.35 (t, 6H).

Step B: Preparation of ethyl 5-amino-3-ethoxy-1-phenyl-1H-pyrazole-4-carboxylate: Prepared according to the method described for Intermediate P135, replacing ethyl 2-cyanopropanoate with diethyl 2-cyanomalonate in Step A to afford the product as a brown syrup (400 mg, 32% yield). MS (apci) m/z=276.1 (M+H).

Intermediate 175

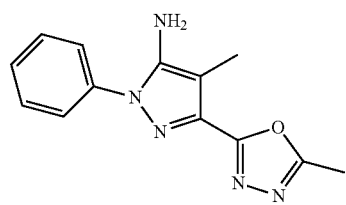 [SMILES: Cc1nnc(-c2nn(-c3ccccc3)c(N)c2C)o1]

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide: To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H₂O (10 mL), extracted DCM (2×10 mL), dried (MgSO₄), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine: A mixture of N'-acetyl-5-amino-4-methyl-1-phenyl-1H-pyrazole-3-carbohydrazide (117 mg, 0.428 mmol) and POCl₃ (0.5 mL) was heated in a pressure tube to 90° C. for 1 hour. The reaction mixture was transferred to a separatory funnel with EtOAc (5 mL), then diluted with saturated aqueous NaHCO₃ (20 mL), extracted with EtOAc (2×15 mL), dried (MgSO₄), filtered and concentrated. The residue was purified by silica column chromatography eluting with 0-75% acetone/hexanes to afford the title compound as a yellow solid (19.6 mg, 18% yield). MS (apci) m/z=256.1 (M+H).

Intermediate 176

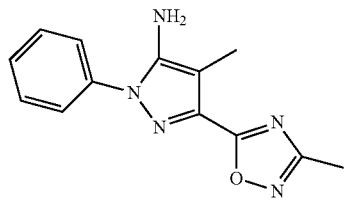 [SMILES: Cc1noc(-c2nn(-c3ccccc3)c(N)c2C)n1]

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N₂ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H₂O (10 mL), extracted DCM (2×15 mL), and the combined organic extracts were dried (MgSO₄), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

Intermediate 177

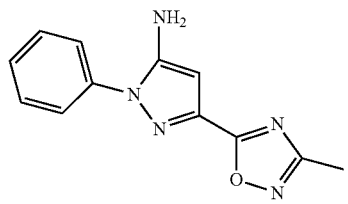 [SMILES: Cc1noc(-c2cc(N)n(-c3ccccc3)n2)n1]

3-(3-methyl-1,2,4-oxadiazol-5-yl)-1-phenyl-1H-pyrazol-5-amine

Prepared according to the method described in Intermediate 176, replacing ethyl 5-amino-4-methyl-1-phenyl-1H-pyrazole-3-carboxylate with ethyl 5-amino-1-phenyl-1H-pyrazole-3-carboxylate (Nanjing Chemlin Chemical Co.) to afford the product as a tan solid (83 mg, 53% yield). MS (apci) m/z=242.1 (M+H).

Intermediate 178

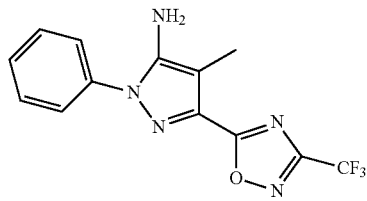 [SMILES: Cc1c(-c2nc(C(F)(F)F)no2)nn(-c2ccccc2)c1N]

4-methyl-1-phenyl-3-(3-(trifluoromethyl)-1,2,4-oxadiazol-5-yl)-1H-pyrazol-5-amine Step A: Preparation of 2,2,2-trifluoro-N'-hydroxyacetimidamide: To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). ¹H NMR (CD₃CN) δ 8.32 (s, 1H), 5.25 (br s, 2H). ¹⁹F NMR (CD₃CN) 6-71.8 (s).

Step B: Preparation of 4-methyl-1-phenyl-3-(3-(trifluoromethyl)-1,2,4-oxadiazol-5-yl)-1H-pyrazol-5-amine: To a suspension of NaH (60% in mineral oil, 356 mg, 0.897 mmol) in THF (5 mL, 0.815 mmol) under N₂ was added 2,2,2-trifluoro-N'-hydroxyacetimidamide (115 mg, 0.897 mmol). The reaction mixture was heated to reflux for 1 hour, then cooled to ambient temperature and powdered 4 A molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H₂O (15 mL), extracted DCM (2×25 mL), and the combined organic extracts were washed with brine (25 mL), dried (MgSO₄), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

Intermediate 179

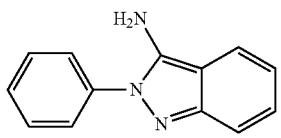 [SMILES: Nc1c2ccccc2nn1-c1ccccc1]

2-phenyl-2H-indazol-3-amine

Step A: Preparation of 1-(2-iodophenyl)-2-phenyldiazene: To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO$_3$ until basic. The mixture was extracted with EtOAc (3×) and the combined extracts were washed with water, saturated NaCl and dried over MgSO$_4$. The solution was filtered, concentrated and the residue purified by reverse phase chromatography to provide the title compound as a red solid (0.880 g, 63% yield). $^1$H NMR (CDCl$_3$) δ 7.23-7.39 (m, 3H), 7.64 (d, 1H), 7.56-7.51 (m, 3H), 7.45 (t, 1H), 7.1 (t, 1H).

Step B: 2-(phenyldiazenyl)benzonitrile: To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with CH$_2$Cl$_2$. The combined filtrate and washes were concentrated to provide the title compound as red-orange solid that was dried in vacuum (0.280 g, 95% yield). $^1$H NMR (CDCl$_3$) δ 8.03-8.06 (m, 2H), 7.88 (dd, 2H), 7.71 (t, 1H), 7.54-7.58 (m, 4H).

Step C: 2-phenyl-2H-indazol-3-amine: A mixture of 2-(phenyldiazenyl) benzonitrile (0.28 g, 1.35 mmol) and SnCl$_2$ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO$_3$ and extracted with CH$_2$Cl$_2$ (2×). The combined organic layers were dried over MgSO$_4$, filtered and concentrated to provide the title compound as a light purple solid that was dried in vacuum (0.241 g, 85% yield). $^1$H NMR (CDCl$_3$) δ 7.69 (d, 2H), 7.52-7.58 (m, 3H), 7.47 (d, 2H), 7.26 (t, 1H), 6.90 (t, 1H), 4.28 (br s, 2H).

Intermediate 180

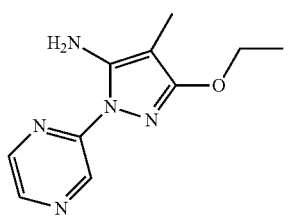 [SMILES: CCOc1nn(-c2cnccn2)c(N)c1C]

3-ethoxy-4-methyl-1-(pyrazin-2-yl)-1H-pyrazol-5-amine

Step A: 5-amino-4-methyl-1-(pyrazin-2-yl)-1H-pyrazol-3(2H)-one: To a mixture of 2-hydrazinylpyrazine (0.551 g, 5.00 mmol) and ethyl 2-cyanopropanoate (0.669 g, 5.00 mmol) in abs. EtOH (10 mL) was added 3M NaOEt in EtOH (0.167 mL, 0.501 mmol) and the mixture was heated at reflux for 64 hours. The mixture was concentrated and the residual yellow-brown solid was treated with EtOAc (30 mL) and sonicated. The resulting tan suspension was stirred vigorously for 8 hours. The solid was collected via vacuum filtration, washed with EtOAc and dried in vacuum to afford the title compound as a light tan powder (682 mg, 71%). $^1$H NMR (DMSO d$_6$) δ 10.3 (br s, 1H), 8.82 (s, 1H), 8.30 (d, 2H), 6.55 (s, 2H), 1.71 (s, 3H).

Step B: 3-ethoxy-4-methyl-1-(pyrazin-2-yl)-1H-pyrazol-5-amine: A mixture of 5-amino-4-methyl-1-(pyrazin-2-yl)-1H-pyrazol-3(2H)-one (382 mg, 2.00 mmol) and powdered K$_2$CO$_3$ (552 mg, 4.00 mmol) in dry DMF (3.0 mL) was stirred at ambient temperature for 10 minutes. The mixture was cooled to 0° C. and bromoethane (229 mg, 2.10 mmol) was added. The mixture was allowed to reach ambient temperature and was stirred 24 hours. The reaction mixture poured into cold H$_2$O (12 mL), allowed to reach ambient temperature and was extracted with EtOAc (3×). The combined extracts were washed with saturated NaCl (2×), dried over MgSO$_4$ and activated carbon. The dried solution was diluted with and equal volume of hexanes and filtered through a SiO$_2$ plug capped with a MgSO$_4$ layer eluting with 50% EtOAc-hexanes. The filtrate was concentrated and the residual yellow solid was washed with hexanes (3×) and dried in vacuum to afford the title compound as a light yellow crystalline solid (195 mg, 45%). $^1$H NMR (CDCl$_3$) δ 9.10 (s, 1H), 8.23 (s, 1H), 8.14 (s, 1H), 5.50 (br s, 2H), 4.33 (q, 2H), 1.80 (s, 3H), 1.42 (t, 3H).

Intermediate 181

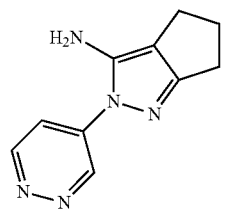 [SMILES: Nc1c2c(nn1-c1ccnnc1)CCC2]

2-(pyridazin-4-yl)-2,4,5,6-tetrahydrocyclopenta[c]pyrazol-3-amine

A suspension of 4-hydrazinylpyridazine hydrobromide (0.368 g, 1.93 mmol) in absolute EtOH (5 mL) was treated with 2-oxocyclopentanecarbonitrile (0.191 g, 1.75 mmol) and the mixture was heated at reflux for 22 hours. The mixture was cooled to ambient temperature and was concentrated to an orange solid. The solid was suspended in 1M NaOH and stirred for 10 minutes. The solid was collected, washed thoroughly with H$_2$O and Et$_2$O and dried in vacuum to furnish title compound as a tan powder (0.323 g, 92%). MS (apci) m/z=202.1 (M+H).

Intermediate 182

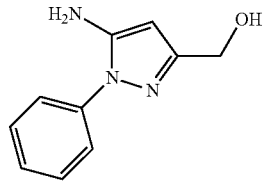 [SMILES: Nc1cc(CO)nn1-c1ccccc1]

(5-amino-1-phenyl-1H-pyrazol-3-yl)methanol

Step A: Ethyl 2-(tert-butyldimethylsilyloxy)acetate: A mixture of ethyl 2-hydroxyacetate (3.00 g, 28.8 mmol), TBDMS-Cl (5.21 g, 34.6 mmol) and imidazole (2.55 g, 37.5 mmol) was stirred at ambient temperature for 60 hours. The mixture was concentrated and the residue was purified by SiO$_2$ chromatography eluting with 10% EtOAc-hexanes to provide the title compound as a colorless oil (4.12 g, 65%). $^1$H NMR (CDCl$_3$) δ 4.12 (s, 2H), 4.09 (q, 2H), 1.17 (t, 3H), 0.18 (s, 9H), 0.00 (s, 6H).

Step B: (5-amino-1-phenyl-1H-pyrazol-3-yl)methanol: A solution of acetonitrile (0.526 mL, 10.1 mmol) in dry THF (20.4 mL, 9.16 mmol) was cooled to −78° C. and 2.5M nBuLi in hexanes (4.21 mL, 10.5 mmol) was added dropwise. The reaction mixture was stirred for 15 minutes and ethyl 2-(tert-butyldimethylsilyloxy)acetate (2.00 g, 9.16 mmol) was added. The reaction mixture was allowed to warm to ambient temperature and was stirred for 2 hours. The reaction mixture was diluted with ice water and was concentrated. The residual aqueous mixture was acidified to pH=5 and extracted with EtOAc (3×). The combined organics were washed with brine, dried over MgSO$_4$, filtered and concentrated. The residual brown oil was dissolved in MeOH (23 mL) and phenyl hydrazine (0.907 mL, 9.14 mmol) was added. The mixture was treated with concentrated HCl (3.81 mL, 45.7 mmol) and heated at reflux for 18 hours. Upon cooling, the mixture was concentrated and the residue was partitioned into in H$_2$O and CH$_2$Cl$_2$. The mixture was filtered and the organic layer was removed from the filtrate. The aqueous portion was washed with CH$_2$Cl$_2$ and was treated with saturated NaHCO$_3$ until basic. The aqueous mixture was extracted with CH$_2$Cl$_2$ (3×) and the combined organic fractions were dried over MgSO$_4$, filtered and concentrated. The residue was purified by silica column chromatography using 70-100% EtOAc/hexanes gradient elution followed by 0-5% MeOH/EtOAc. The product pools were combined and concentrated to give the title compound as a yellow foam (0.760 g, 44% yield). MS (apci) m/z=190.1 (M+H).

Intermediate 183

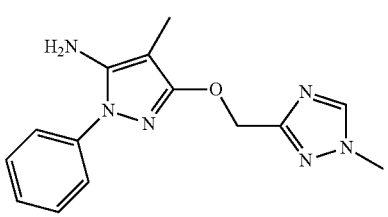 [SMILES: Cc1c(OCc2ncn(C)n2)nn(-c2ccccc2)c1N]

4-methyl-3-((1-methyl-1H-1,2,4-triazol-3-yl)methoxy)-1-phenyl-1H-pyrazol-5-amine The title compound was prepared by the method as described for Intermediate P135, substituting bromoethane with 3-(chloromethyl)-1-methyl-1H-1,2,4-triazole hydrochloride. The product was isolated as a gold syrup (110 mg, 27%). MS (apci) m/z 285.1 (M+H).

Intermediate 184

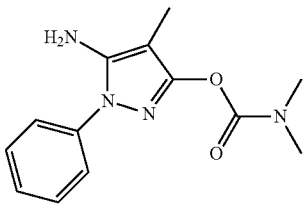 [SMILES: Cc1c(OC(=O)N(C)C)nn(-c2ccccc2)c1N]

5-amino-4-methyl-1-phenyl-1H-pyrazol-3-yl dimethylcarbamate

A mixture of 5-amino-4-methyl-1-phenyl-1H-pyrazol-3(2H)-one (Intermediate P135 Step A, 0.378 g, 2.00 mmol) and powdered K$_2$CO$_3$ (0.553 g, 4.00 mmol) in dry DMF (4 mL) was stirred at ambient temperature for 5 minutes. Dimethylcarbamoyl chloride (0.206 mL, 2.20 mmol) was added and the mixture was stirred for 6 hours. The mixture was poured into chilled H$_2$O (40 mL) and was extracted with EtOAc (3×). The combined extracts were washed with saturated NaCl (2×), dried over MgSO$_4$ and filtered through a SiO$_2$ plug capped with a MgSO$_4$ layer (EtOAc elution). The filtrate was concentrated and the residue dried in vacuum to give the title compound as a light gold syrup (0.507 g, 97%). MS (apci) m/z=261.1 (M+H).

Intermediate 185

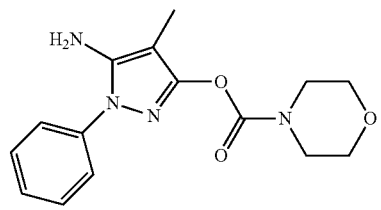 [SMILES: Cc1c(OC(=O)N2CCOCC2)nn(-c2ccccc2)c1N]

5-amino-4-methyl-1-phenyl-1H-pyrazol-3-yl morpholine-4-carboxylate

The title compound was prepared using morpholine-4-carbonyl chloride in the procedure outlined for 5-amino-4-methyl-1-phenyl-1H-pyrazol-3-yl dimethylcarbamate (Intermediate 184). The compound was isolated as a light yellow wax (0.285 g, 47%). $^1$H NMR (CDCl$_3$) δ 7.54 (d, 2H), 7.43 (t, 2H), 7.31 (t, 1H), 3.66-3.78 (m, 8H), 3.57 (br s, 2H), 1.85 (s, 3H).

Intermediate 186

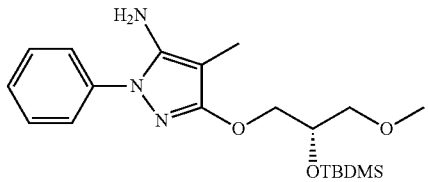 [SMILES: COC[C@@H](COc1nn(-c2ccccc2)c(N)c1C)O[Si](C)(C)C(C)(C)C]

(S)-3-(2-((tert-butyldimethylsilyl)oxy)-3-methoxy-propoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol: A mixture of 5-amino-4-methyl-1-phenyl-1H-pyrazol-3(2H)-one (P135 Step A, 1.21 g, 6.40 mmol) and powdered $K_2CO_3$ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled $H_2O$ (25 mL) and extracted with EtOAc (3×). The combined extracts were washed with saturated NaCl (2×), dried over $MgSO_4$ and filtered through a $SiO_2$ plug capped with a layer of $MgSO_4$ eluting with EtOAc. The filtrate was concentrated to give the title compound as a colorless, viscous oil (701 mg, 40%). MS (apci) m/z=278.1 (M+H).

Step B: (S)-3-(2-((tert-butyldimethyl silyl)oxy)-3-methoxypropoxy)-4-methyl-1-phenyl-1H-pyrazol-5-amine: To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to $H_2O$ (70 mL), mixed for 5 minutes and extracted with $Et_2O$ (3×). The combined extracts were washed with saturated NaCl (2×) and dried over $MgSO_4$. The dried solution was filtered through a $SiO_2$ plug capped with a layer of $MgSO_4$ ($Et_2O$ elution). The filtrate was concentrated to give the title compound as a colorless oil that was dried in vacuum (940 mg, 105%). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 187

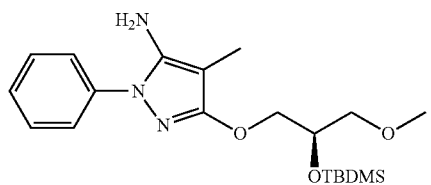 [SMILES: COC[C@H](COc1nn(-c2ccccc2)c(N)c1C)O[Si](C)(C)C(C)(C)C]

(R)-3-(2-((tert-butyldimethylsilyl)oxy)-3-methoxy-propoxy)-4-methyl-1-phenyl-1H-pyrazol-5-amine The title compound was prepared using the procedure described for (S)-3-(2-((tert-butyldimethylsilyl)oxy)-3-methoxypropoxy)-4-methyl-1-phenyl-1H-pyrazol-5-amine (Intermediate 186) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). $^1$H NMR (CDCl$_3$) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 188

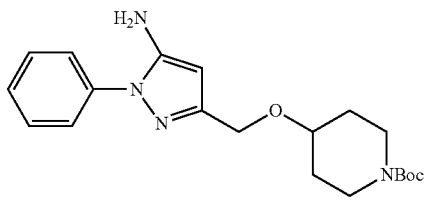 [SMILES: CC(C)(C)OC(=O)N1CCC(OCc2cc(N)n(-c3ccccc3)n2)CC1]

tert-butyl 4-((5-amino-1-phenyl-1H-pyrazol-3-yl)methoxy)piperidine-1-carboxylate Step A: tert-butyl 4-(2-ethoxy-2-oxoethoxy)piperidine-1-carboxylate: A solution of tert-butyl 4-hydroxypiperidine-1-carboxylate (2.00 g, 9.94 mmol) in dry THF (25 mL) was cooled to 0° C. and KOtBu (1.12 g, 9.94 mmol) was added. The mixture was allowed to reach ambient temperature and was stirred for 10 minutes. The mixture was cooled to 0° C. and ethyl 2-bromoacetate (1.65 mL, 14.9 mmol) was added dropwise. The reaction was allowed to reach ambient temperature and was stirred for 17 hours. The mixture was partitioned into in $H_2O$ and EtOAc, mixed and the organic layer was removed. The organic layer was dried over $MgSO_4$, filtered and concentrated. The residual thick yellow oil was purified by silica chromatography using a 10-25% EtOAc/hexanes gradient elution to afford the title compound as a colorless oil (0.967 g, 34% yield). $^1$H NMR (CDCl$_3$) δ 4.22 (q, 2H), 4.12 (s, 2H), 3.67-3.84 (m, 2H), 3.52-3.63 (m, 1H), 3.05-3.11 (m, 2H), 1.81-1.90 (m, 2H), 1.53-1.62 (m, 2H), 1.45 (s, 9H), 1.29 (t, 3H).

Step B: tert-butyl 4-((5-amino-1-phenyl-1H-pyrazol-3-yl)methoxy)piperidine-1-carboxylate: A solution of diisopropylamine (1.08 mL, 7.74 mmol) in dry THF (5 mL) was cooled to 0° C. and 2.5M nBuLi in hexanes (2.96 mL, 7.41 mmol) was slowly added. The mixture was stirred at 0° C. for 10 minutes and was cooled to −78° C. Acetonitrile (0.404 mL, 7.74 mmol) was added and the mixture was stirred for 15 minutes. A solution of tert-butyl 4-(2-ethoxy-2-oxoethoxy)piperidine-1-carboxylate (0.967 g, 3.37 mmol) in THF (2.5 mL) was added and the mixture was stirred at −78° C. for 1 hour. The mixture was allowed to reach ambient temperature, was quenched with ice water and concentrated. The residual aqueous mixture was neutralized with 2M HCl and was extracted with $CH_2Cl_2$ (3×). The combined organic fractions were dried over $MgSO_4$, filtered and concentrated to provide the crude cyano-ketone as a yellow oil that was used immediately in the next step.

Step C: tert-butyl 4-((5-amino-1-phenyl-1H-pyrazol-3-yl)methoxy)piperidine-1-carboxylate: The crude oil obtained in Step B was dissolved in EtOH (17 mL) and phenylhydrazine (0.396 mL, 3.99 mmol) was added. The mixture was heated at 60° C. for 60 hours, was cooled to ambient temperature and was concentrated. The residue was partitioned into EtOAc and water, mixed and the organic layer removed. The aqueous layer was extracted with EtOAc (2×) and the combined EtOAc portions were dried over $MgSO_4$, filtered and concentrated. The residual orange oil was purified by silica chromatography using a 10-100% EtOAc/hexanes gradient elution. The pooled product fractions were concentrated and the residual yellow-orange oil was re-purified by reverse phase HPLC using a 0-100% acetonitrile/ water gradient to provide the title compound as an orange foam (0.264 g, 21% yield). MS (apci) m/z=373.2 (M+H).

Intermediate 189

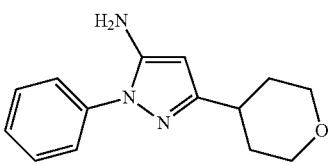 [SMILES: Nc1cc(C2CCOCC2)nn1-c1ccccc1]

1-phenyl-3-(tetrahydro-2H-pyran-4-yl)-1H-pyrazol-5-amine

Step A: 3-oxo-3-(tetrahydro-2H-pyran-4-yl)propanenitrile: A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled $H_2O$ (250 mL) and was extracted with $Et_2O$ (3×). The aqueous portion was cooled to 0° C. and 6M HCl was added dropwise to pH=3 (starting pH=12). The mixture was extracted with EtOAc (3×) and the combined extracts were dried over $MgSO_4$. The solution eluted through a $SiO_2$ plug eluting with EtOAc. The filtrate was concentrated to give the title compound as a colorless oil (2.52 g, 66%). $^1H$ NMR (CDCl$_3$) δ 3.99-4.06 (m, 2H), 3.54 (s, 2H), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine:To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in $H_2O$ (75 mL) and EtOAc (40 mL). 2M NaOH was added to pH=5 with vigorous mixing, the organic layer was removed and the aqueous was extracted with EtOAc (2×). The combined EtOAc fractions were washed with $H_2O$ and saturated NaCl. The solution was diluted with an equal volume of hexanes, dried over $MgSO_4$/activated carbon and eluted through a $SiO_2$ plug eluting with 50% EtOAc-hexanes. The filtrate was concentrated to give a gold syrup. The syrup was treated with $Et_2O$ and stirred until a fine, granular suspension formed. The solid was collected, washed with $Et_2O$ and dried in vacuum to furnish the title compound as a white solid (2.01 g, 65%). $^1H$ NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compounds were prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
| --- | --- | --- |
| 190 | 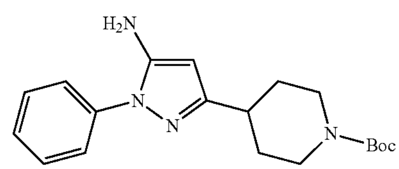 [SMILES: CC(C)(C)OC(=O)N1CCC(c2cc(N)n(-c3ccccc3)n2)CC1] | MS (apci) m/z = 343.1 (M + H) |
| 191 | 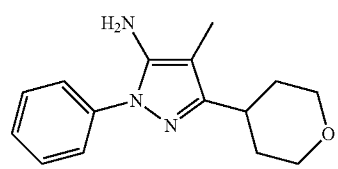 [SMILES: Cc1c(C2CCOCC2)nn(-c2ccccc2)c1N] | MS (apci) m/z = 258.0 (M + H) |
| 192 | 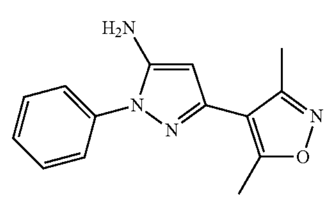 [SMILES: Cc1noc(C)c1-c1cc(N)n(-c2ccccc2)n1] | $^1H$ NMR (CDCl$_3$) δ 7.62 (d, 2H), 7.50 (t, 2H), 7.37 (t, 1H), 5.72 (s, 1H), 3.91 (br s, 2H), 2.58 (s, 3H), 2.44 (s, 3H). |
| 193 | 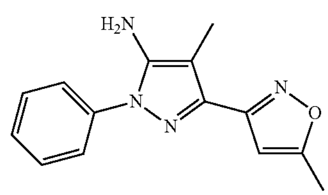 [SMILES: Cc1cc(-c2nn(-c3ccccc3)c(N)c2C)no1] | $^1H$ NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |

-continued

| Intermediate # | Structure | Data |
|---|---|---|
| 194 | 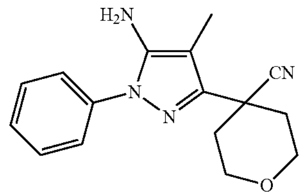 [SMILES: Cc1c(C2(C#N)CCOCC2)nn(-c2ccccc2)c1N] | $^1$H NMR (CDCl$_3$) δ 7.45-7.56 (m, 4H), 7.35 (t, 1H), 4.00-4.06 (m, 2H), 3.88 (dt, 2H), 3.62 (br s, 2H), 2.18-2.34 (m, 4H), 2.11 (s, 3H). |
| 195 | 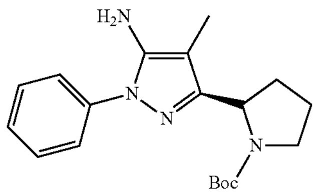 | MS (apci) m/z = 343.2 (M + H) |
| 196 | 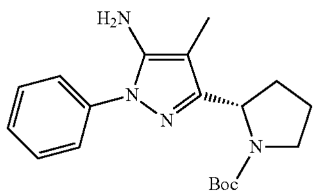 [SMILES: Cc1c([C@@H]2CCCN2C(=O)OC(C)(C)C)nn(-c2ccccc2)c1N] | MS (apci) m/z = 343.2 (M + H) |
| 197 | 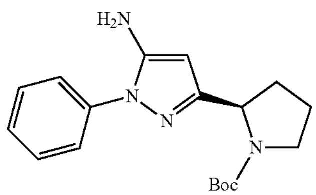 [SMILES: CC(C)(C)OC(=O)N1CCC[C@@H]1c1cc(N)n(-c2ccccc2)n1] | MS (apci) m/z = 329.2 (M + H) |
| 198 | 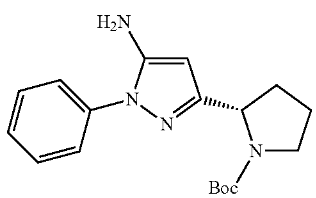 [SMILES: CC(C)(C)OC(=O)N1CCC[C@H]1c1cc(N)n(-c2ccccc2)n1] | MS (apci) m/z = 329.2 (M + H) |

Intermediate 199

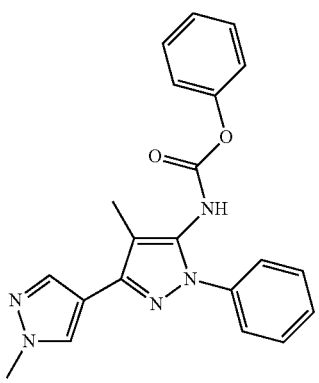 [SMILES: Cc1c(-c2cnn(C)c2)nn(-c2ccccc2)c1NC(=O)Oc1ccccc1]

Phenyl 1',4-dimethyl-1-phenyl-1H,1'H-3,4'-bipyrazol-5-ylcarbamate

Step A: ethyl 1-methyl-1H-pyrazole-4-carboxylate: To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile: To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbarbonate solution The aqueous layer was extracted with DCM (3×1000 mL). The combined organic extracts were dried over MgSO₄ filtered and concentrated to yield the 2-methyl-3-(1-methyl-1H-pyrazol-4-yl)-3-oxopropanenitrile as an amber oil (92 g, 82%). MS (apci) m/z=162.1 (M−H).

Step C: 1',4-dimethyl-1-phenyl-1H,1'H-3,4'-bipyrazol-5-amine: A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H,1'H-3,4'-bipyrazol-5-amine (93 g, 100%).

Step D: phenyl 1',4-dimethyl-1-phenyl-1H,1'H-3,4'-bipyrazol-5-ylcarbamate: In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

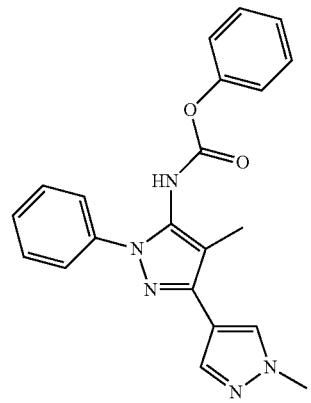 [SMILES: Cc1c(-c2cnn(C)c2)nn(-c2ccccc2)c1NC(=O)Oc1ccccc1]

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 201

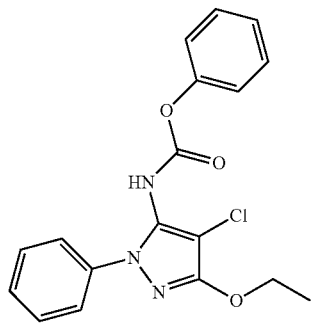 [SMILES: CCOc1nn(-c2ccccc2)c(NC(=O)Oc2ccccc2)c1Cl]

phenyl (4-chloro-3-ethoxy-1-phenyl-1H-pyrazol-5-yl)carbamate

Step A: Preparation of phenyl (3-ethoxy-1-phenyl-1H-pyrazol-5-yl)carbamate: To a suspension of 3-ethoxy-1-phenyl-1H-pyrazol-5-amine (Intermediate P139, 169 mg, 0.832 mmol) in EtOAc (5 mL) at 0° C. was added 2.0 M aqueous NaOH solution (1.25 mL, 2.50 mmol), followed by dropwise addition of phenyl carbonochloridate (0.178 mL, 1.41 mmol). The reaction was stirred at ambient temperature for 15 hours. The reaction mixture was diluted with EtOAc and phase-separated. The organic layer was washed with water and brine, dried over MgSO₄, and concentrated. The residue was purified by flash chromatography on silica gel (6:1 hexanes:EtOAc) to give the title compound (219 mg, 81% yield). MS (apci) m/z=324.1 (M+H).

Step B: Preparation of phenyl (4-chloro-3-ethoxy-1-phenyl-1H-pyrazol-5-yl)carbamate: To a solution of phenyl 3-ethoxy-1-phenyl-1H-pyrazol-5-ylcarbamate (92 mg, 0.28 mmol) and pyridinium 4-methylbenzenesulfonate (7.2 mg, 0.028 mmol) in DCM (2 mL) was added N-chlorosuccinimide (42 mg, 0.31 mmol) at ambient temperature. The mixture was stirred at ambient temperature for 2 days and then concentrated under reduced pressure. The residue was purified by flash chromatography on silica gel (9:1, hexanes/EtOAc) to give the title compound (76 mg, 75% yield). MS (apci) m/z=358.1 (M+H).

Intermediate 203

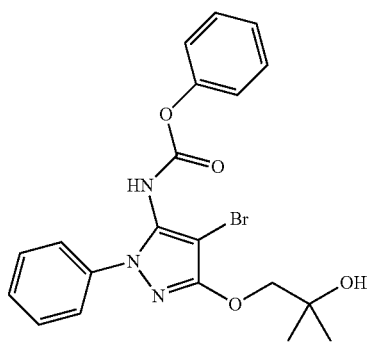 [SMILES: CC(C)(O)COc1nn(-c2ccccc2)c(NC(=O)Oc2ccccc2)c1Br]

Phenyl (4-bromo-3-(2-hydroxy-2-methylpropoxy)-1-phenyl-1H-pyrazol-5-yl)carbamate Step A: Preparation of 5-amino-1-phenyl-1H-pyrazol-3 (2H)-one: Prepared according to the method described for Intermediate P1, replacing 4,4-dimethyl-3-oxopentanenitrile with ethyl 2-cyanoacetate, and substituting phenylhydrazine for ethyl 3-hydrazinylbenzoate hydrochloride. MS (apci) m/z=176.0 (M+H).

Step B: Preparation of 1-((5-amino-1-phenyl-1H-pyrazol-3-yl)oxy)-2-methylpropan-2-ol: A mixture of 5-amino-1-phenyl-1H-pyrazol-3(2H)-one (0.330 g, 1.88 mmol), 2,2-dimethyloxirane (0.143 g, 1.98 mmol) and K₂CO₃ (0.521 g, 3.77 mmol) in DMA (5 mL) was heated at 80° C. for 3 days. After cooling, the reaction mixture was diluted with EtOAc, washed with water and brine and dried over MgSO₄. The mixture was filtered through a pad of SiO₂ eluting with EtOAc to yield the title compound. MS (apci) m/z=248.1 (M+H).

Step C: Preparation of phenyl (3-(2-hydroxy-2-methylpropoxy)-1-phenyl-1H-pyrazol-5-yl)carbamate: Prepared according to the method described for Intermediate 201. Step A using 1-((5-amino-1-phenyl-1H-pyrazol-3-yl)oxy)-2-methylpropan-2-ol as a replacement for 3-ethoxy-1-phenyl-1H-pyrazol-5-amine. MS (apci) m/z=368.1 (M+H).

Step D: Preparation of phenyl (4-bromo-3-(2-hydroxy-2-methylpropoxy)-1-phenyl-1H-pyrazol-5-yl)carbamate: Prepared according to the method described for Intermediate 201, Step B using N-bromosuccinimide as a replacement for N-chloro succinimide, and substituting phenyl (3-(2-hydroxy-2-methylpropoxy)-1-phenyl-1H-pyrazol-5-yl)carbamate for phenyl 3-ethoxy-1-phenyl-1H-pyrazol-5-ylcarbamate. MS (apci) m/z=446.1 (M+H).

The following compounds prepared according to the method describe for the preparation of Intermediate 200, using the appropriate amino pyrazole intermediate:

| Intermediate # | Structure | Name | Data |
| --- | --- | --- | --- |
| 204 | 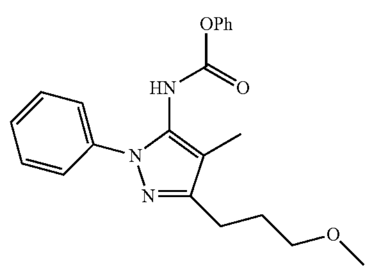 [SMILES: COCCCc1nn(-c2ccccc2)c(NC(=O)Oc2ccccc2)c1C] | phenyl 3-(3-methoxypropyl)-4-methyl-1-phenyl-1H-pyrazol-5-ylcarbamate | MS (apci) m/z = 366.1 (M + H). |
| 205 | 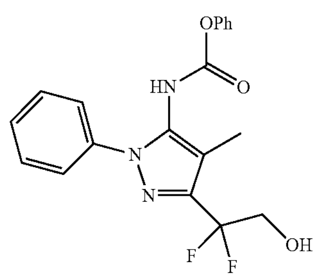 [SMILES: Cc1c(C(F)(F)CO)nn(-c2ccccc2)c1NC(=O)Oc1ccccc1] | phenyl 3-(1,1-difluoro-2-hydroxyethyl)-4-methyl-1-phenyl-1H-pyrazol-5-ylcarbamate | MS (apci) m/z = 374.1 (M + H). |

| Intermediate # | Structure | Name | Data |
|---|---|---|---|
| 206 | 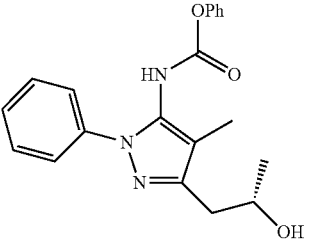 [SMILES: Cc1c(C[C@H](C)O)nn(-c2ccccc2)c1NC(=O)Oc1ccccc1] | (S)-phenyl 3-(2-hydroxypropyl)-4-methyl-1-phenyl-1H-pyrazol-5-ylcarbamate | MS (apci) m/z = 352.1 (M + H). |
| 207 | 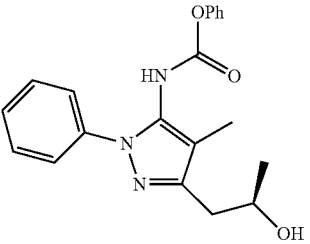 [SMILES: Cc1c(C[C@@H](C)O)nn(-c2ccccc2)c1NC(=O)Oc1ccccc1] | (R)-phenyl 3-(2-hydroxypropyl)-4-methyl-1-phenyl-1H-pyrazol-5-ylcarbamate | MS (apci) m/z = 352.1 (M + H). |
| 208 | 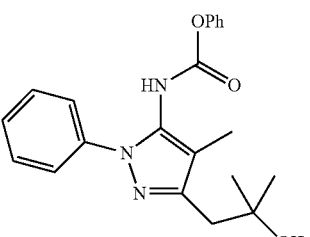 | phenyl 3-(2-hydroxy-2-methylpropyl)-4-methyl-1-phenyl-1H-pyrazol-5-ylcarbamate | MS (apci) m/z = 366.2 (M + H). |
| 209 | 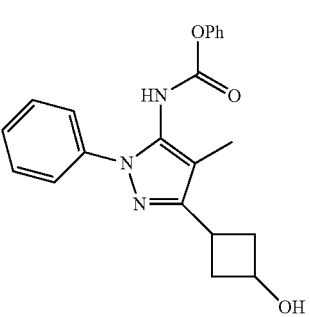 [SMILES: Cc1c(C2CC(O)C2)nn(-c2ccccc2)c1NC(=O)Oc1ccccc1] | phenyl 3-(3-hydroxycyclobutyl)-4-methyl-1-phenyl-1H-pyrazol-5-ylcarbamate | MS (apci) m/z = 364.2 (M + H). |
| 210 | 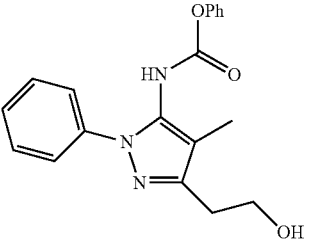 [SMILES: Cc1c(CCO)nn(-c2ccccc2)c1NC(=O)Oc1ccccc1] | phenyl 3-(2-hydroxyethyl)-4-methyl-1-phenyl-1H-pyrazol-5-ylcarbamate | MS (apci) m/z = 338.1 (M + H). |
| 211 | 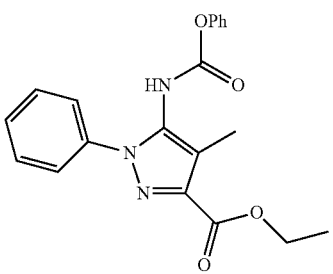 [SMILES: CCOC(=O)c1nn(-c2ccccc2)c(NC(=O)Oc2ccccc2)c1C] | ethyl 4-methyl-5-(phenoxycarbonylamino)-1-phenyl-1H-pyrazole-3-carboxylate | MS (apci) m/z = 366.1 (M + H). |

| Intermediate # | Structure | Name | Data |
|---|---|---|---|
| 212 | 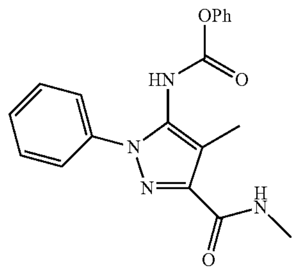 [SMILES: CNC(=O)c1nn(-c2ccccc2)c(NC(=O)Oc2ccccc2)c1C] | phenyl 4-methyl-3-(methylcarbamoyl)-1-phenyl-1H-pyrazol-5-ylcarbamate | MS (apci) m/z = 351.1 (M + H). |
| 213 | 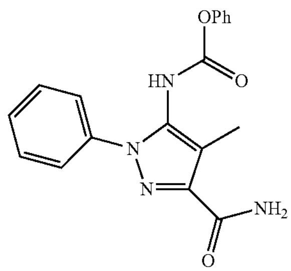 [SMILES: Cc1c(C(N)=O)nn(-c2ccccc2)c1NC(=O)Oc1ccccc1] | phenyl 3-carbamoyl-4-methyl-1-phenyl-1H-pyrazol-5-ylcarbamate | MS (apci) m/z = 337.1 (M + H). |
| 214 | 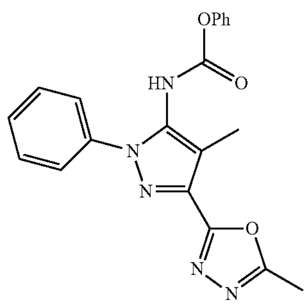 [SMILES: Cc1nnc(-c2nn(-c3ccccc3)c(NC(=O)Oc3ccccc3)c2C)o1] | phenyl (4-methyl-3-(5-methyl-1,3,4-oxadiazol-2-yl)-1-phenyl-1H-pyrazol-5-yl)carbamate | MS (apci) m/z = 376.1 (M + H). |
| 215 | 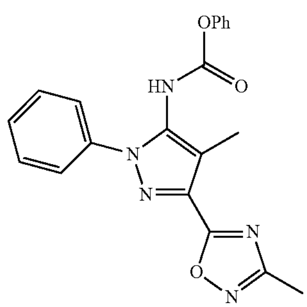 [SMILES: Cc1noc(-c2nn(-c3ccccc3)c(NC(=O)Oc3ccccc3)c2C)n1] | phenyl 4-methyl-3-(3-methyl-1,2,4-oxadiazol-5-yl)-1-phenyl-1H-pyrazol-5-ylcarbamate | MS (apci) m/z = 376.1 (M + H). |
| 216 | 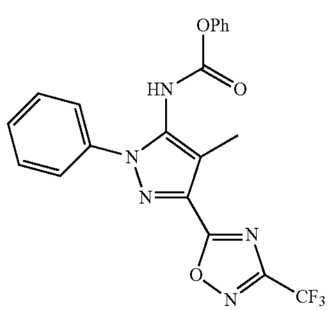 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |

-continued

| Intermediate # | Structure | Name | Data |
|---|---|---|---|
| 217 | 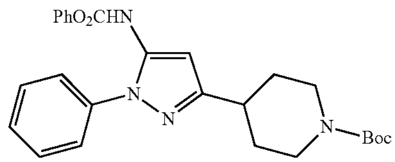 | tert-butyl 4-(5-((phenoxycarbonyl)amino)-1-phenyl-1H-pyrazol-3-yl)piperidine-1-carboxylate | MS (apci) m/z = 463.3 (M + H) |
| 218 | 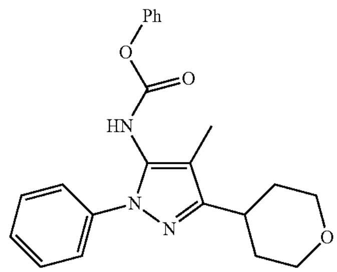 [SMILES: Cc1c(C2CCOCC2)nn(-c2ccccc2)c1NC(=O)Oc1ccccc1] | phenyl (4-methyl-1-phenyl-3-(tetrahydro-2H-pyran-4-yl)-1H-pyrazol-5-yl)carbamate | MS (apci) m/z = 378.2 (M + H) |
| 219 | 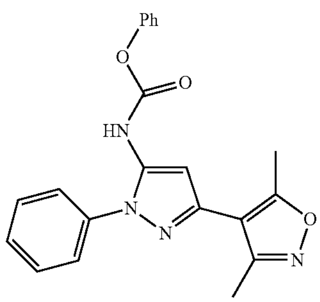 [SMILES: Cc1noc(C)c1-c1cc(NC(=O)Oc2ccccc2)n(-c2ccccc2)n1] | phenyl (3-(3,5-dimethylisoxazol-4-yl)-1-phenyl-1H-pyrazol-5-yl)carbamate | $^1$H NMR (CDCl$_3$) δ 7.56-7.64 (m, 4H), 7.48-7.52 (m, 1H), 7.40 (t, 2H), 7.26 (t, 2H), 7.16 (br s, 2H), 6.71 (br s, 1H), 2.60 (s, 3H) 2.46 (s, 3H) |
| 220 | 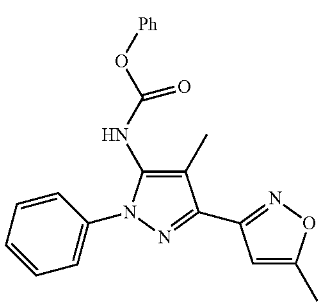 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$H NMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |
| 221 | 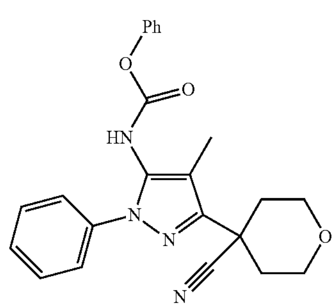 [SMILES: Cc1c(C2(C#N)CCOCC2)nn(-c2ccccc2)c1NC(=O)Oc1ccccc1] | phenyl (3-(4-cyanotetrahydro-2H-pyran-4-yl)-4-methyl-1-phenyl-1H-pyrazol-5-yl)carbamate | $^1$H NMR (CDCl$_3$) δ 7.06-7.56 (m, 9H), 6.75 (br s, 1H), 6.51 (s, 1H), 4.04 (d, 2H) 3.89 (t, 2H), 2.20-2.39 (m, 4H), 2.28 (s, 3H) |

-continued

| Intermediate # | Structure | Name | Data |
| --- | --- | --- | --- |
| 222 | 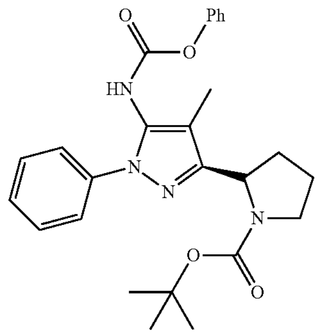 | (R)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |
| 223 | 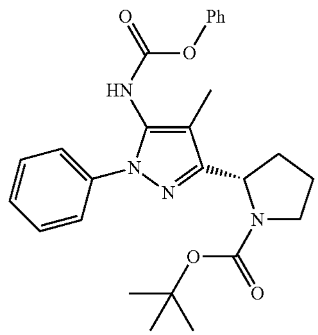 [SMILES: Cc1c([C@@H]2CCCN2C(=O)OC(C)(C)C)nn(-c2ccccc2)c1NC(=O)Oc1ccccc1] | (S)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |
| 224 | 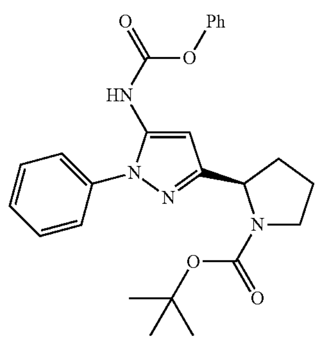 [SMILES: CC(C)(C)OC(=O)N1CCC[C@@H]1c1cc(NC(=O)Oc2ccccc2)n(-c2ccccc2)n1] | (R)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 225 | 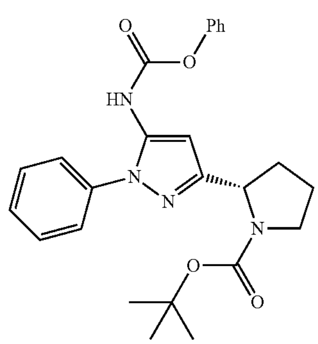 [SMILES: CC(C)(C)OC(=O)N1CCC[C@H]1c1cc(NC(=O)Oc2ccccc2)n(-c2ccccc2)n1] | (S)-tert-butyl 2-(5-((phenoxycarbonyl)amino)-1-phenyl-1H-pyrazol-3-yl)pyrrolidine-1-carboxylate | MS (apci) m/z = 449.2 (M + H) |

| Intermediate # | Structure | Name | Data |
|---|---|---|---|
| 226 | 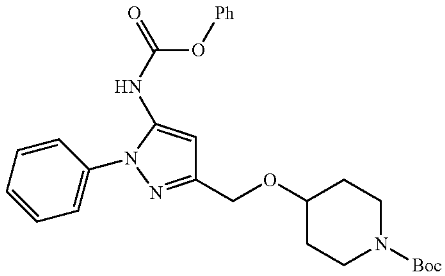 [SMILES: CC(C)(C)OC(=O)N1CCC(OCc2cc(NC(=O)Oc3ccccc3)n(-c3ccccc3)n2)CC1] | tert-butyl 4-((5-((phenoxycarbonyl)amino)-1-phenyl-1H-pyrazol-3-yl)methoxy)piperidine-1-carboxylate | MS (apci) m/z = 493.2 (M + H) |
| 227 | 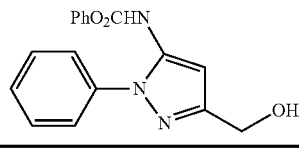 | phenyl (3-(hydroxymethyl)-1-phenyl-1H-pyrazol-5-yl)carbamate | MS (apci) m/z = 310.1 (M + H) |

Intermediate 228

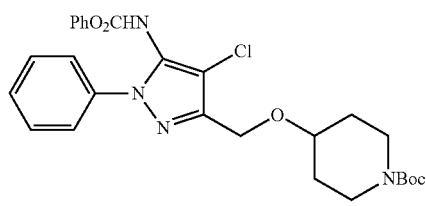

tert-butyl 4-((4-chloro-5-((phenoxycarbonyl)amino)-1-phenyl-1H-pyrazol-3-yl)methoxy)piperidine-1-carboxylate To a suspension of tert-butyl 4-((5-(phenoxycarbonylamino)-1-phenyl-1H-pyrazol-3-yl)methoxy)piperidine-1-carboxylate (Intermediate 226), 98.5 mg, 0.200 mmol) in DCM (2.0 mL) was added pyridinium 4-methylbenzenesulfonate (PPTS) (5.03 mg, 0.020 mmol) and N-chlorosuccinimide (40.1 mg, 0.300 mmol). The resulting solution was stirred at ambient temperature for 8 days. The mixture was diluted with water and CH$_2$Cl$_2$, the organic layer was separated and the aqueous was extracted with CH$_2$Cl$_2$ (2×). The combined organic fractions were dried over MgSO$_4$, filtered and concentrated. The residue was purified by silica chromatography using 30-40% EtOAc/hexanes gradient elution to afford the title compound as an orange oil (73.5 mg, 70% yield). MS (apci) m/z=527.2 (M+H).

Intermediate 229

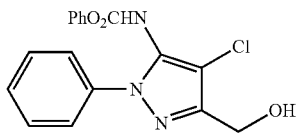

Phenyl (4-chloro-3-(hydroxymethyl)-1-phenyl-1H-pyrazol-5-yl)carbamate

Prepared from phenyl 3-(hydroxymethyl)-1-phenyl-1H-pyrazol-5-ylcarbamate (Intermediate 227) using the procedure outlined for the preparation of tert-butyl 4-((4-chloro-5-((phenoxycarbonyl)amino)-1-phenyl-1H-pyrazol-3-yl)methoxy)piperidine-1-carboxylate (Intermediate 228). In this instance, the compound was isolated a white solid (108 mg, 28%). MS (apci) m/z=344.0 (M+H).

Intermediate 230

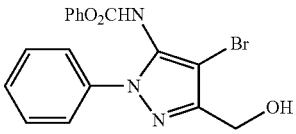

Phenyl (4-bromo-3-(hydroxymethyl)-1-phenyl-1H-pyrazol-5-yl)carbamate

To a suspension of phenyl 3-(hydroxymethyl)-1-phenyl-1H-pyrazol-5-ylcarbamate (Intermediate 227, 100 mg, 0.323 mmol) in CH$_2$Cl$_2$ (1.6 mL) was added pyridinium 4-methylbenzenesulfonate (PPTS) (8.12 mg, 0.0323 mmol) and N-bromosuccinimide (86.3 mg, 0.485 mmol). The reaction mixture was stirred for 16 hours at ambient temperature. The resulting suspension was filtered and the collected solid washed briefly with CH$_2$Cl$_2$ and dried in vacuum to afford the title compound a white solid (48.5 mg, 39%). MS (apci) m/z=388.0 (M+H).

The following pyrazole intermediates were made according to the methods described for the preparation of Intermediate 228, 229 or 230.

| Intermediate | Structure | Name | MS (apci) m/z |
|---|---|---|---|
| 231 | 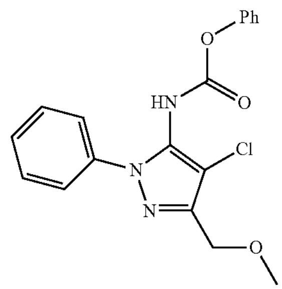 [SMILES: COCc1nn(-c2ccccc2)c(NC(=O)Oc2ccccc2)c1Cl] | phenyl (4-chloro-3-(methoxymethyl)-1-phenyl-1H-pyrazol-5-yl)carbamate | 358.1 (M + H) |
| 232 | 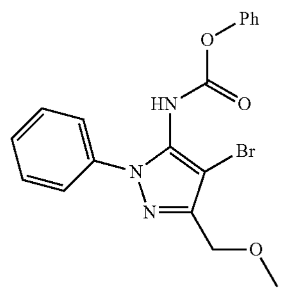 [SMILES: COCc1nn(-c2ccccc2)c(NC(=O)Oc2ccccc2)c1Br] | phenyl (4-bromo-3-(methoxymethyl)-1-phenyl-1H-pyrazol-5-yl)carbamate | 402.2 (M + H) |
| 233 | 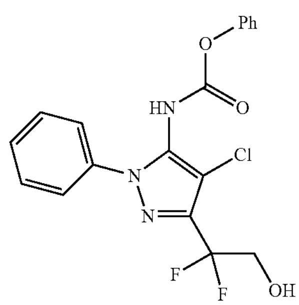 [SMILES: O=C(Nc1c(Cl)c(C(F)(F)CO)nn1-c1ccccc1)Oc1ccccc1] | phenyl (4-chloro-3-(1,1-difluoro-2-hydroxyethyl)-1-phenyl-1H-pyrazol-5-yl)carbamate | 394.1 (M + H) |
| 234 | 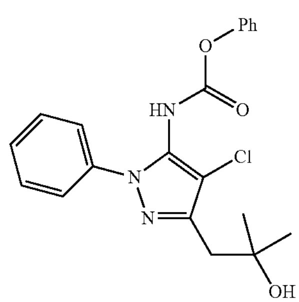 [SMILES: CC(C)(O)Cc1nn(-c2ccccc2)c(NC(=O)Oc2ccccc2)c1Cl] | phenyl (4-chloro-3-(2-hydroxy-2-methylpropyl)-1-phenyl-1H-pyrazol-5-yl)carbamate | 386.1 (M + H) |
| 235 | 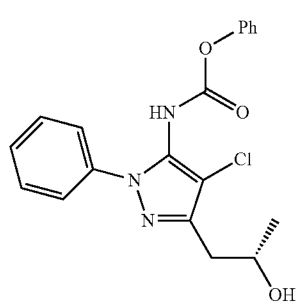 [SMILES: C[C@H](O)Cc1nn(-c2ccccc2)c(NC(=O)Oc2ccccc2)c1Cl] | (S)-phenyl (4-chloro-3-(2-hydroxypropyl)-1-phenyl-1H-pyrazol-5-yl)carbamate | 372.1 (M + H) |

| Intermediate | Structure | Name | MS (apci) m/z |
|---|---|---|---|
| 236 | 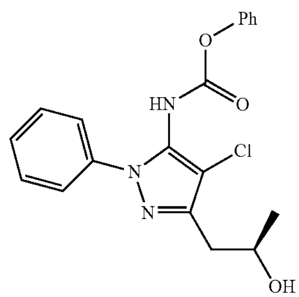 [SMILES: C[C@@H](O)Cc1nn(-c2ccccc2)c(NC(=O)Oc2ccccc2)c1Cl] | (R)-phenyl (4-chloro-3-(2-hydroxypropyl)-1-phenyl-1H-pyrazol-5-yl)carbamate | 372.1 (M + H) |
| 237 | 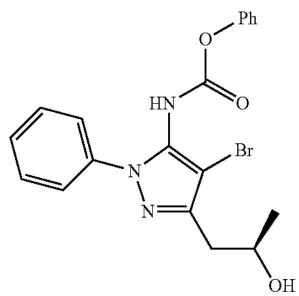 [SMILES: C[C@@H](O)Cc1nn(-c2ccccc2)c(NC(=O)Oc2ccccc2)c1Br] | (R)-phenyl (4-bromo-3-(2-hydroxypropyl)-1-phenyl-1H-pyrazol-5-yl)carbamate | 416.0 (M + H) |
| 238 | 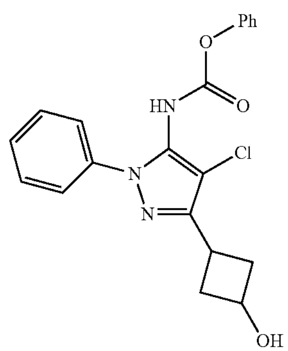 [SMILES: O=C(Nc1c(Cl)c(C2CC(O)C2)nn1-c1ccccc1)Oc1ccccc1] | phenyl (4-chloro-3-(3-hydroxycyclobutyl)-1-phenyl-1H-pyrazol-5-yl)carbamate | 384.1 (M + H) |
| 239 | 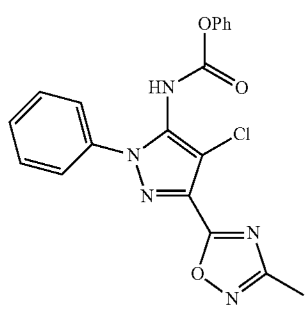 [SMILES: Cc1noc(-c2nn(-c3ccccc3)c(NC(=O)Oc3ccccc3)c2Cl)n1] | phenyl 4-chloro-3-(3-methyl-1,2,4-oxadiazol-5-yl)-1-phenyl-1H-pyrazol-5-ylcarbamate | 396.0 (M + H) |
| 240 | 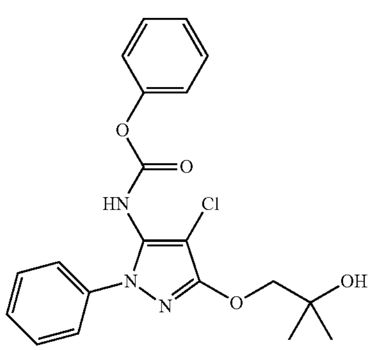 | phenyl (4-chloro-3-(2-hydroxy-2-methylpropoxy)-1-phenyl-1H-pyrazol-5-yl)carbamate | 446.1 (M + H) |

| Intermediate | Structure | Name | MS (apci) m/z |
|---|---|---|---|
| 241 | 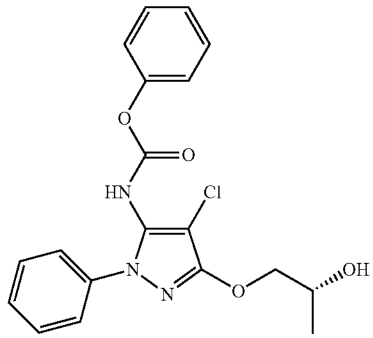 [SMILES: C[C@@H](O)COc1nn(-c2ccccc2)c(NC(=O)Oc2ccccc2)c1Cl] | phenyl (4-chloro-3-(2-hydroxy-2-methylpropoxy)-1-phenyl-1H-pyrazol-5-yl)carbamate | 388.1 (M + H) |
| 242 | 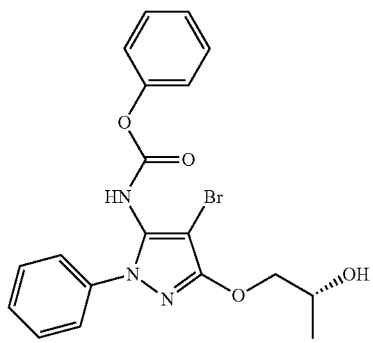 [SMILES: C[C@@H](O)COc1nn(-c2ccccc2)c(NC(=O)Oc2ccccc2)c1Br] | phenyl (4-bromo-3-(2-hydroxy-2-methylpropoxy)-1-phenyl-1H-pyrazol-5-yl)carbamate | 433.0 (M + H) |
| 243 | 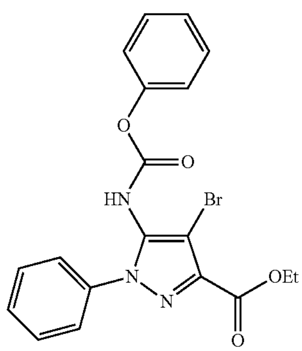 [SMILES: CCOC(=O)c1nn(-c2ccccc2)c(NC(=O)Oc2ccccc2)c1Br] | ethyl 4-bromo-5-((phenoxycarbonyl)amino)-1-phenyl-1H-pyrazole-3-carboxylate | 430.0 (M + H) |

Intermediate 245

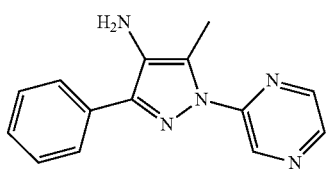 [SMILES: Cc1c(N)c(-c2ccccc2)nn1-c1cnccn1]

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine. To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with H$_2$O (30 mL). The green suspension was stirred for 1 hour and the solid was collected via vacuum filtration. The collected solid was washed with H$_2$O and dried in vacuum. The solid was suspended in EtOH (25 mL) and concentrated HCl (500 µL) was added. The mixture was heated at reflux for 20 hours, cooled to ambient temperature and diluted with chilled H$_2$O (75 mL). The mixture was treated with 1M NaOH to pH=7 and was extracted with Et$_2$O (3×). The combined extracts were washed with saturated NaCl and dried over MgSO$_4$. The dried solution was filtered through packed Celite® and concentrated. The residual green-yellow solid was purified on a SiO$_2$ column using step gradient elution (25% CH$_2$Cl$_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine. To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 μL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with H₂O and mixed. The resulting orange suspension treated with 2M HCl to pH=1 and the mixture was extracted with Et₂O (3×). The aqueous portion was treated with 2M NaOH to pH=8 and extracted with EtOAc (3×). The combined EtOAc extracts were washed with saturated NaCl and dried over MgSO₄/activated carbon. The solution was eluted through a SiO₂ plug eluting with EtOAc. The eluent was concentrated to give the title compound as a light yellow wax (33 mg, 13%). MS (esi) m/z=252.2 (M+H).

Intermediate 246

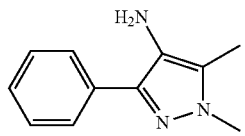

1,5-dimethyl-3-phenyl-1H-pyrazol-4-amine

Step A: 1,5-dimethyl-4-nitroso-3-phenyl-1H pyrazole: To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. Et₂O (50 mL) and H₂O (10 mL) were added to the mixture followed by slow addition of saturated Na₂CO₃ until pH=8 was obtained. The organic layer was removed and the aqueous layer was extracted with Et₂O (2×). The combined organic fractions were dried over Na₂SO₄, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine: To a solution of 1,5-dimethyl-4-nitroso-3-phenyl-1H-pyrazole (1.32 g, 6.60 mmol) in MeOH (50 mL) was added Pd(OH)₂ on carbon (200 mg, 20 wt %, 0.286 mmol) and the reaction mixture was shaken under 50 psi of H₂ for 3 hours at ambient temperature. The reaction mixture was evacuated, purged with N₂ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate 247

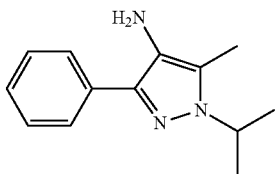 [SMILES: Cc1c(N)c(-c2ccccc2)nn1C(C)C]

1-isopropyl-5-methyl-3-phenyl-1H-pyrazol-4-amine

The title compound was prepared according to the method described for Intermediate 246, using isopropylhydrazine hydrochloride in place of methylhydrazine in Step A to provide 620 mg (57%) of the title compound over 2 steps. MS (apci) m/z=216.1 (M+H).

Intermediate 248

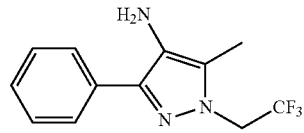 [SMILES: Cc1c(N)c(-c2ccccc2)nn1CC(F)(F)F]

5-methyl-3-phenyl-1-(2,2,2-trifluoroethyl)-1H-pyrazol-4-amine

Step A: 5-methyl-4-nitroso-3-phenyl-1-(2,2,2-trifluoroethyl)-1H-pyrazole: The title compound was prepared using (2,2,2-trifluoroethyl)hydrazine in place of methylhydrazine in Step A of the procedure described for the preparation of 1,5-dimethyl-3-phenyl-1H-pyrazol-4-amine (Intermediate 246). The compound was isolated as a green solid (999 mg, 71%). ¹H NMR (CDCl₃) δ 7.60-7.73 (m, 5H), 4.70 (q, 2H), 2.27 (t, 3H).

Step B: 5-methyl-3-phenyl-1-(2,2,2-trifluoroethyl)-1H-pyrazol-4-amine: To a mixture of 5-methyl-4-nitroso-3-phenyl-1-(2,2,2-trifluoroethyl)-1H-pyrazole (50 mg, 0.186 mmol) and Zn dust (60.7 mg, 0.929 mmol) in EtOH (0.4 mL) was added concentrated HCl (17.0 μL, 0.204 mmol) and the mixture was heated at reflux for 3 hours. The mixture was cooled to ambient temperature and was diluted with MeOH and filtered. The filtrate was concentrated and the residue was diluted in water. The aqueous mixture was treated with saturated NaHCO₃ until pH=10 was achieved. The mixture was extracted with DCM (3×) and the combined extracts were dried over Na₂SO₄, filtered and concentrated afford the title compound as a yellow oil (47.1 mg, 99.4% yield). MS (apci) m/z=256.1 (M+H).

Intermediate 249

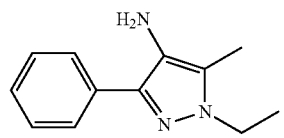

1-ethyl-5-methyl-3-phenyl-1H-pyrazol-4-amine

Step A: 1-ethyl-5-methyl-4-nitroso-3-phenyl-1H-pyrazole: The title compound was prepared according to the procedure described for the preparation of Intermediate 246, using ethylhydrazine oxalate in place of methylhydrazine in Step A. 1-Ethyl-5-methyl-4-nitroso-3-phenyl-1H-pyrazole was isolated as a green oil (288 mg, 26%). ¹H NMR (CDCl₃) δ 8.19 (d, 2H), 7.46-7.50 (m, 3H), 4.15 (q, 2H), 2.43 (s, 3H), 1.50 (t, 3H). The minor regioisomer, 1-ethyl-3-methyl-4- nitroso-5-phenyl-1H-pyrazole, was also obtained as a blue-green solid (165 mg, 15%). $^1$H NMR (CDCl$_3$) δ 7.71 (dd, 2H), 7.59 (m, 3H), 4.17 (q, 2H), 2.28 (s, 3H), 1.51 (t, 3H).

Step B: 1-ethyl-5-methyl-3-phenyl-1H-pyrazol-4-amine: Prepared according to the procedure described for the preparation of Intermediate 248, using 1-ethyl-5-methyl-4-nitroso-3-phenyl-1H-pyrazole in Step B. the title compound was isolated as a light purple solid (281 mg, 104%). MS (apci) m/z=202.1 (M+H).

Intermediate 250

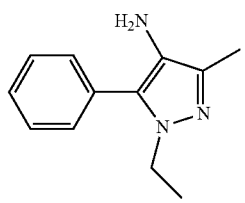

1-ethyl-3-methyl-5-phenyl-1H-pyrazol-4-amine

Prepared according to the procedure described for the preparation of Intermediate 249, using 1-ethyl-3-methyl-4-nitroso-5-phenyl-1H-pyrazole in Step A. The title compound was prepared according to Step B. The compound was isolated as a colorless oil (82.4 mg, 52.5%) after purification by reverse-phase chromatography. MS (apci) m/z=202.1 (M+H).

Intermediate 251

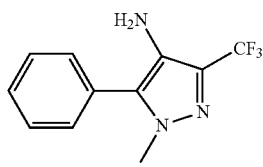 [SMILES: Cn1nc(C(F)(F)F)c(N)c1-c1ccccc1]

1-methyl-5-phenyl-3-(trifluoromethyl)-1H-pyrazol-4-amine

Step A: 4,4,4-trifluoro-2-(hydroxyimino)-1-phenylbutane-1,3-dione: A solution of 4,4,4-trifluoro-1-phenylbutane-1,3-dione (5.00 g, 23.1 mmol) in HOAc (46.3 mL) was chilled to 10° C. and sodium nitrite (1.84 g, 26.6 mmol) in water (6.0 mL) was added. The mixture was stirred at ambient temperature for 90 minutes and was diluted with H$_2$O (150 mL). The mixture was extracted with Et$_2$O (3×) and the combined organic fractions were carefully washed with saturated NaHCO$_3$ until pH=9. The Et$_2$O solution was washed with H$_2$O and saturated NaCl and was dried over MgSO$_4$. The dried solution was filtered and concentrated to afford the title compound as a yellow foam (4.21 g, 74.2% yield). MS (apci) m/z=244.1 (M−H).

Step B: 4-nitroso-3-phenyl-5-(trifluoromethyl)-1H-pyrazole: A solution of hydrazine monohydrate (0.204 g, 4.08 mmol) in EtOH (5 mL) was cooled to 0° C. and 4,4,4-trifluoro-2-(hydroxyimino)-1-phenylbutane-1,3-dione (1.00 g, 4.08 mmol) in EtOH (15 mL) was added. The reaction mixture was stirred at ambient temperature for 3 hours, excess powdered MgSO$_4$ was added and the mixture was heated at 60° C. for 16 hours. The mixture was cooled to ambient temperature, filtered and concentrated to afford the crude title compound as a green solid (78.7 mg, 8.0%) that was taken directly to the next step. MS (apci) m/z=240.0 (M−H).

Step C: 1-methyl-5-phenyl-3-(trifluoromethyl)-1H-pyrazol-4-amine: To a solution of 4-nitroso-3-phenyl-5-(trifluoromethyl)-1H-pyrazole (78.7 mg, 0.326 mmol) in DMF (1.6 mL) was added NaH (14.4 mg, 0.359 mmol) and the mixture was stirred at ambient temperature for 30 minutes. The mixture was treated with methyl iodide (40.6 μL, 0.653 mmol) and stirred for 17 hours. The reaction mixture was directly purified by reverse phase HPLC using 20-100% acetonitrile/water gradient elution to provide a light blue solid (40.2 mg). The solid was dissolved in EtOH (0.35 mL) and was subjected to the reduction procedure described in Step B of the preparation of 5-methyl-3-phenyl-1-(2,2,2-trifluoroethyl)-1H-pyrazol-4-amine (Intermediate 248). The title compound was obtained as white solid (25.1 mg, 66.1%).

Intermediate 252

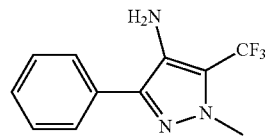 [SMILES: Cn1nc(-c2ccccc2)c(N)c1C(F)(F)F]

1-methyl-3-phenyl-5-(trifluoromethyl)-1H-pyrazol-4-amine

Step A: 1-methyl-4-nitroso-3-phenyl-5-(trifluoromethyl)-1H-pyrazole. To a solution of methylhydrazine (0.214 mL, 4.08 mmol) in EtOH (20 mL) was added 4,4,4-trifluoro-2-(hydroxyimino)-1-phenylbutane-1,3-dione (Intermediate 251, Step A; 1.00 g, 4.079 mmol). The reaction mixture was stirred at ambient temperature for 1 hour and excess MgSO$_4$ was added. The mixture was stirred at 60° C. for 48 hours and was cooled to ambient temperature. The mixture was filtered and the filtrate concentrated to a green residue. The residue was purified by silica gel chromatography using a 10-30% EtOAc/hexanes gradient for elution to provide the title compound as a green solid (482 mg, 46%). $^1$H NMR (CDCl$_3$) δ 7.89 (d, 2H), 7.45-7.52 (m, 3H), 4.15 (s, 3H).

Step B: 1-methyl-3-phenyl-5-(trifluoromethyl)-1H-pyrazol-4-amine. Prepared from 1-methyl-4-nitroso-3-phenyl-5-(trifluoromethyl)-1H-pyrazole according to the method described for the preparation of Intermediate 248, Step B. The title compound was obtained as white solid (309 mg, 68%). $^1$H NMR (CDCl$_3$) δ 7.65 (d, 2H), 7.45 (t, 2H), 7.35 (t, 1H), 3.93 (s, 3H), 3.52 (br s, 2H).

SYNTHETIC EXAMPLES

Example 1

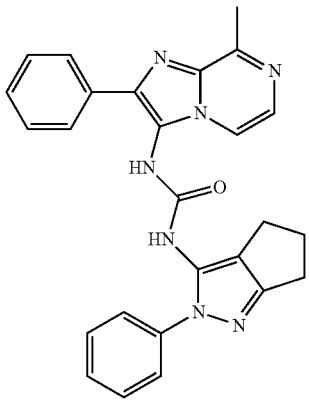 [SMILES: Cc1nccn2c(NC(=O)Nc3c4c(nn3-c3ccccc3)CCC4)c(-c3ccccc3)nc12]

1-(8-methyl-2-phenylimidazo[1,2-a]pyrazin-3-yl)-3-(2-phenyl-2,4,5,6-tetrahydrocyclopenta[c]pyrazol-3-yl)urea To a suspension of 8-methyl-2-phenylimidazo[1,2-a]pyrazin-3-amine dihydrochloride [Preparation A1] (50 mg, 0.17 mmol) and phenyl (2-phenyl-2,4,5,6-tetrahydrocyclopenta[c]pyrazol-3-yl)carbamate [Intermediate 28] (59 mg, 0.19 mmol) in DMA (2 mL) was added DIEA (103 μL, 0.59 mmol). The solution was stirred at ambient temperature for 16 hours then partitioned between saturated $NH_4Cl$ (20 mL) and EtOAc (20 mL). The resulting precipitate was filtered, washed with EtOAc and $Et_2O$ then dried under vacuum to afford the title compound (42 mg, 56% yield) as a white solid. MS (apci) m/z=450.0 (M+H).

Example 2

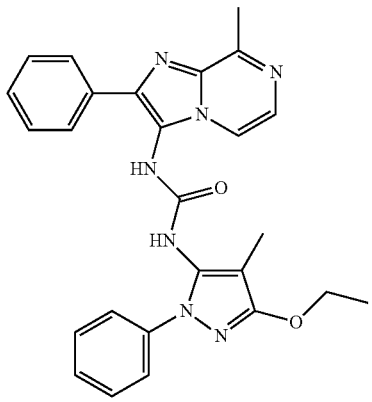 [SMILES: CCOc1nn(-c2ccccc2)c(NC(=O)Nc2c(-c3ccccc3)nc3c(C)nccn23)c1C]

1-(3-ethoxy-4-methyl-1-phenyl-1H-pyrazol-5-yl)-3-(8-methyl-2-phenylimidazo[1,2-a]pyrazin-3-yl)urea Prepared according to the procedure of Example 1, substituting phenyl (2-phenyl-2,4,5,6-tetrahydrocyclopenta[c]pyrazol-3-yl)carbamate [Intermediate 28] with phenyl 3-ethoxy-4-methyl-1-phenyl-1H-pyrazol-5-ylcarbamate [Intermediate 8] to afford the title compound (21 mg, 26% yield) as a yellow solid. MS (apci) m/z=468.1 (M+H).

Example 3

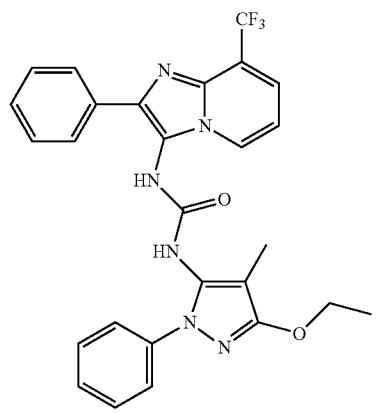 [SMILES: CCOc1nn(-c2ccccc2)c(NC(=O)Nc2c(-c3ccccc3)nc3c(C(F)(F)F)cccn23)c1C]

1-(3-ethoxy-4-methyl-1-phenyl-1H-pyrazol-5-yl)-3-(2-phenyl-8-(trifluoromethyl)imidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-phenyl-8-(trifluoromethyl)imidazo[1,2-a]pyridin-3-amine [Preparation A5] to afford the title compound (34 mg, 41% yield) as a cream solid. MS (apci) m/z=521.2 (M+H).

Example 4

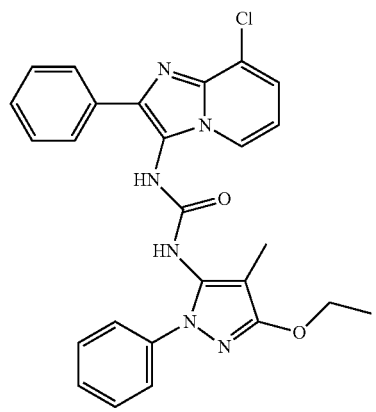

1-(8-chloro-2-phenylimidazo[1,2-a]pyridin-3-yl)-3-(3-ethoxy-4-methyl-1-phenyl-1H-pyrazol-5-yl)urea Prepared according to the procedure of Example 2, substituting 8-methyl-2-phenylimidazo[1,2-a]pyrazin-3-amine dihydrochloride [Preparation A1] with 8-chloro-2-phenylimidazo[1,2-a]pyridin-3-amine hydrochloride [Preparation A4] to afford the title compound (41 mg, 47% yield) as a cream solid. MS (apci) m/z=487.2 (M+H).

Example 5

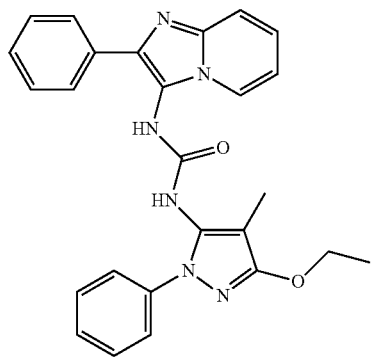 [SMILES: CCOc1nn(-c2ccccc2)c(NC(=O)Nc2c(-c3ccccc3)nc3ccccn23)c1C]

1-(3-ethoxy-4-methyl-1-phenyl-1H-pyrazol-5-yl)-3-(2-phenylimidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-phenylimidazo[1,2-a]pyridin-3-amine [Preparation A2] to afford the title compound (53 mg, 49% yield) as a cream solid. MS (apci) m/z=453.2 (M+H).

Example 6

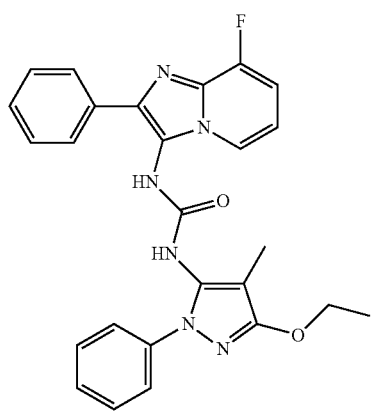 [SMILES: CCOc1nn(-c2ccccc2)c(NC(=O)Nc2c(-c3ccccc3)nc3c(F)cccn23)c1C]

1-(3-ethoxy-4-methyl-1-phenyl-1H-pyrazol-5-yl)-3-(8-fluoro-2-phenylimidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 8-fluoro-2-phenylimidazo[1,2-a]pyridin-3-amine dihydrochloride [Preparation A6] to afford the title compound (12 mg, 19% yield) as a white powder. MS (apci) m/z=471.2 (M+H).

Example 7

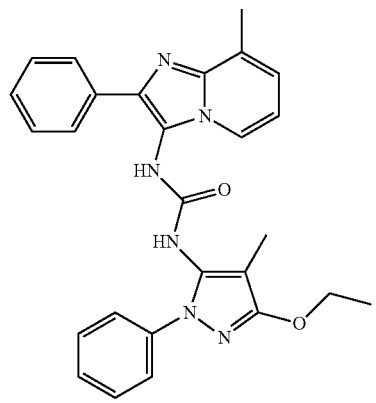

1-(3-ethoxy-4-methyl-1-phenyl-1H-pyrazol-5-yl)-3-(8-methyl-2-phenylimidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 8-methyl-2-phenylimidazo[1,2-a]pyridin-3-amine dihydrochloride [Preparation A3] to afford the title compound (58 mg, 74% yield) as a white powder. MS (apci) m/z=467.2 (M+H).

Example 8

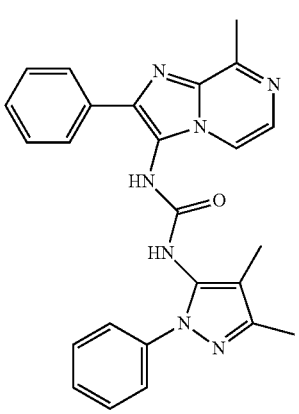 [SMILES: Cc1nn(-c2ccccc2)c(NC(=O)Nc2c(-c3ccccc3)nc3c(C)nccn23)c1C]

1-(3,4-dimethyl-1-phenyl-1H-pyrazol-5-yl)-3-(8-methyl-2-phenylimidazo[1,2-a]pyrazin-3-yl)urea Prepared according to the procedure of Example 1, substituting phenyl (2-phenyl-2,4,5,6-tetrahydrocyclopenta[c]pyrazol-3-yl)carbamate [Intermediate 28] with phenyl (3,4-dimethyl-1-phenyl-1H-pyrazol-5-yl)carbamate [Intermediate 16] to afford the title compound (38 mg, 52% yield) as a pale yellow solid. MS (apci) m/z=438.2 (M+H).

Example 9

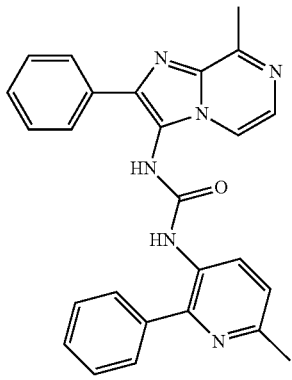 [SMILES: Cc1ccc(NC(=O)Nc2c(-c3ccccc3)nc3c(C)nccn23)c(-c2ccccc2)n1]

1-(8-methyl-2-phenylimidazo[1,2-a]pyrazin-3-yl)-3-(6-methyl-2-phenylpyridin-3-yl)urea Prepared according to the procedure of Example 1, substituting phenyl (2-phenyl-2,4,5,6-tetrahydrocyclopenta[c]pyrazol-3-yl)carbamate [Intermediate 28] with phenyl (6-methyl-2-phenylpyridin-3-yl)carbamate [Intermediate 29] to afford the title compound (38 mg, 52% yield) as a pale yellow solid. MS (apci) m/z=435.2 (M+H).

Example 10

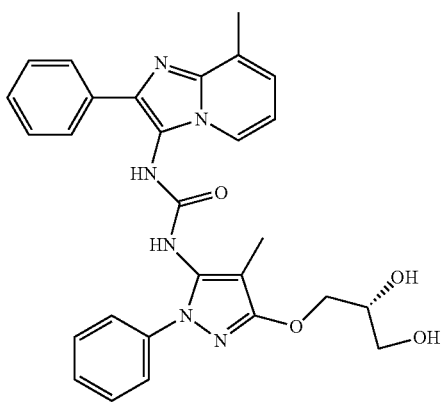 [SMILES: Cc1c(OC[C@H](O)CO)nn(-c2ccccc2)c1NC(=O)Nc1c(-c2ccccc2)nc2c(C)cccn12]

(R)-1-(3-(2,3-dihydroxypropoxy)-4-methyl-1-phenyl-1H-pyrazol-5-yl)-3-(8-methyl-2-phenylimidazo[1,2-a]pyridin-3-yl)urea Step A: Preparation of (S)-1-(3-((2,2-dimethyl-1,3-dioxolan-4-yl)methoxy)-4-methyl-1-phenyl-1H-pyrazol-5-yl)-3-(8-methyl-2-phenylimidazo[1,2-a]pyridin-3-yl)urea: To a suspension of 8-methyl-2-phenylimidazo[1,2-a]pyridin-3-amine dihydrochloride [Preparation A3] (31.8 mg, 0.11 mmol) and (S)-phenyl 3-((2,2-dimethyl-1,3-dioxolan-4-yl)methoxy)-4-methyl-1-phenyl-1H-pyrazol-5-yl carbamate [Intermediate 10] (50 mg, 0.12 mmol) in DMA (2 mL) was added DIEA (65 µL, 0.38 mmol). The solution was stirred at ambient temperature for 16 hours then partitioned between saturated NH₄Cl (20 mL) and EtOAc (20 mL). The aqueous layer was extracted with EtOAc (2×10 mL) and the combined organic phases were washed with water (4×10 mL) and brine (10 mL) then dried over Na₂SO₄, filtered and concentrated under vacuum. The residue was purified by silica column chromatography eluting with 2% MeOH/DCM to afford (S)-1-(3-((2,2-dimethyl-1,3-dioxolan-4-yl)methoxy)-4-methyl-1-phenyl-1H-pyrazol-5-yl)-3-(8-methyl-2-phenylimidazo[1,2-a]pyridin-3-yl)urea (55 mg, 93% yield) as a yellow/green solid. MS (apci) m/z=553.3 (M+H).

Step B: Preparation of (R)-1-(3-(2,3-dihydroxypropoxy)-4-methyl-1-phenyl-1H-pyrazol-5-yl)-3-(8-methyl-2-phenylimidazo[1,2-a]pyridin-3-yl)urea: A solution of (S)-1-(3-((2,2-dimethyl-1,3-dioxolan-4-yl)methoxy)-4-methyl-1-phenyl-1H-pyrazol-5-yl)-3-(8-methyl-2-phenylimidazo[1,2-a]pyridin-3-yl)urea (55 mg, 0.10 mmol) in THF (2 mL) was cooled to 0° C. and 1M HCl (2 mL) was added. The solution was stirred at ambient temperature for 3 hours then concentrated to half volume. The solution was treated with 2M NaOH to pH=9-10 then extracted with EtOAc (3×10 mL). The combined organic extracts were washed with brine (10 mL) then dried over Na₂SO₄, filtered and concentrated under vacuum. The residue was triturated with 1:1 DCM/Et₂O, filtered and dried under vacuum to afford the title compound (18 mg, 35% yield) as a pale orange powder. MS (apci) m/z=513.2 (M+H).

Example 11

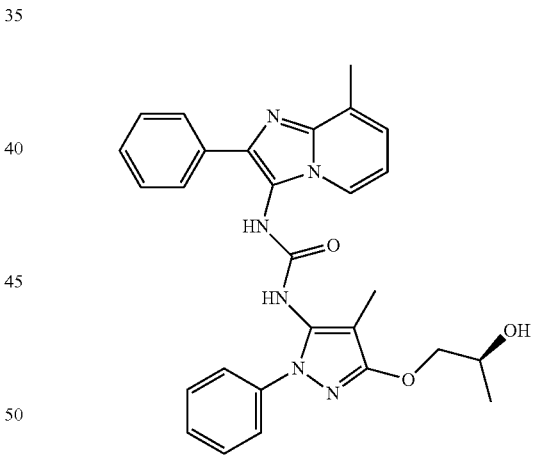

(S)-1-(3-(2-hydroxypropoxy)-4-methyl-1-phenyl-1H-pyrazol-5-yl)-3-(8-methyl-2-phenylimidazo[1,2-a]pyridin-3-yl)urea Prepared according to the procedure of Example 10, substituting (S)-phenyl 3-((2,2-dimethyl-1,3-dioxolan-4-yl)methoxy)-4-methyl-1-phenyl-1H-pyrazol-5-yl carbamate [Intermediate 10] with (S)-phenyl (3-(2-((tert-butyldimethylsilyl)oxy)propoxy)-4-methyl-1-phenyl-1H-pyrazol-5-yl)carbamate [Intermediate 12] in Step A to afford the title compound (19.5 mg, 60% yield) as a white solid. MS (apci) m/z=497.2 (M+H).

Example 12

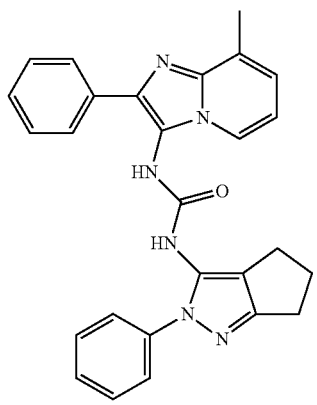 [SMILES: Cc1cccn2c(NC(=O)Nc3c4c(nn3-c3ccccc3)CCC4)c(-c3ccccc3)nc12]

1-(8-methyl-2-phenylimidazo[1,2-a]pyridin-3-yl)-3-(2-phenyl-2,4,5,6-tetrahydrocyclopenta[c]pyrazol-3-yl)urea Prepared according to the procedure of Example 1, substituting 8-methyl-2-phenylimidazo[1,2-a]pyrazin-3-amine dihydrochloride [Preparation A1] with 8-methyl-2-phenylimidazo[1,2-a]pyridin-3-amine dihydrochloride [Preparation A3] to afford the title compound (48 mg, 75% yield) as a white solid. MS (apci) m/z=449.2 (M+H).

Example 13

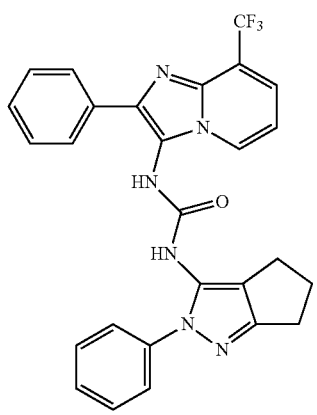 [SMILES: O=C(Nc1c2c(nn1-c1ccccc1)CCC2)Nc1c(-c2ccccc2)nc2c(C(F)(F)F)cccn12]

1-(2-phenyl-2,4,5,6-tetrahydrocyclopenta[c]pyrazol-3-yl)-3-(2-phenyl-8-(trifluoromethyl)imidazo[1,2-a]pyridin-3-yl)urea Prepared according to the procedure of Example 1, substituting 8-methyl-2-phenylimidazo[1,2-a]pyrazin-3-amine dihydrochloride [Preparation A1] with 2-phenyl-8-(trifluoromethyl)imidazo[1,2-a]pyridin-3-amine hydrochloride [Preparation A5] to afford the title compound (47 mg, 66% yield) as a white solid. MS (apci) m/z=503.2 (M+H).

Example 14

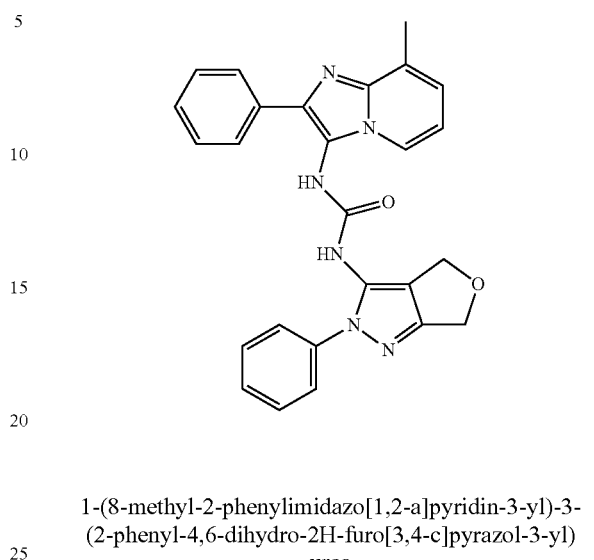

1-(8-methyl-2-phenylimidazo[1,2-a]pyridin-3-yl)-3-(2-phenyl-4,6-dihydro-2H-furo[3,4-c]pyrazol-3-yl)urea Prepared according to the procedure of Example 10, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (2-phenyl-4,6-dihydro-2H-furo[3,4-c]pyrazol-3-yl)carbamate [Intermediate 20] to afford the title compound (12 mg, 18% yield) as a cream powder. MS (apci) m/z=451.2 (M+H).

Example 15

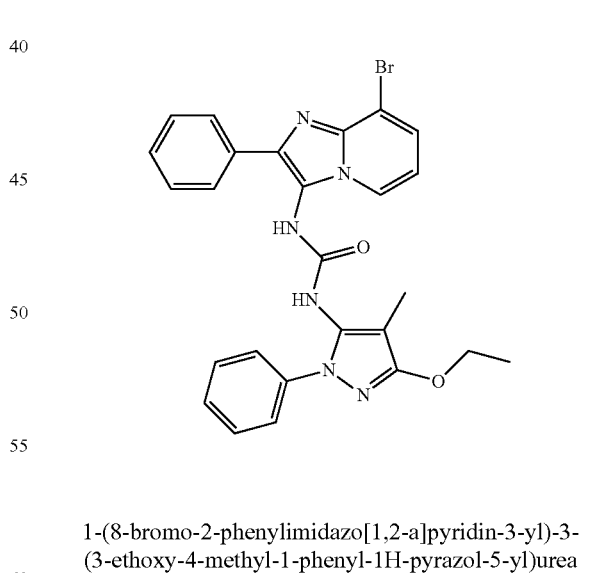

1-(8-bromo-2-phenylimidazo[1,2-a]pyridin-3-yl)-3-(3-ethoxy-4-methyl-1-phenyl-1H-pyrazol-5-yl)urea Prepared according to the procedure of Example 2, substituting 8-methyl-2-phenylimidazo[1,2-a]pyrazin-3-amine dihydrochloride [Preparation A1] with 8-bromo-2-phenylimidazo[1,2-a]pyridin-3-amine dihydrochloride [Preparation A7] to afford the title compound (73 mg, 51% yield) as a pale yellow solid. MS (apci) m/z=533.1 (M+H).

Example 16

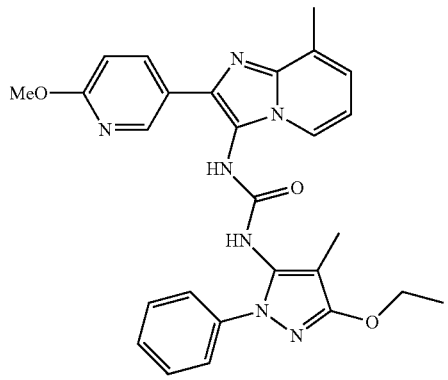 [SMILES: CCOc1nn(-c2ccccc2)c(NC(=O)Nc2c(-c3ccc(OC)nc3)nc3c(C)cccn23)c1C]

1-(3-ethoxy-4-methyl-1-phenyl-1H-pyrazol-5-yl)-3-(2-(6-methoxypyridin-3-yl)-8-methylimidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-(6-methoxypyridin-3-yl)-8-methylimidazo[1,2-a]pyridin-3-amine dihydrochloride [Preparation A11] to afford the title compound (64 mg, 48% yield) as a cream solid. MS (apci) m/z=498.2 (M+H).

Example 17

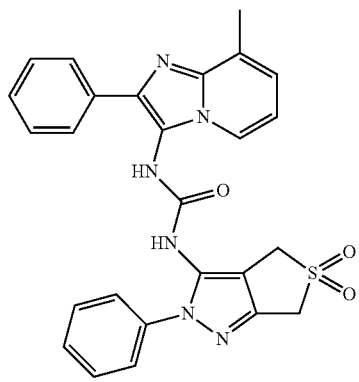 [SMILES: Cc1cccn2c(NC(=O)Nc3c4c(nn3-c3ccccc3)CS(=O)(=O)C4)c(-c3ccccc3)nc12]

1-(5,5-dioxido-2-phenyl-4,6-dihydro-2H-thieno[3,4-c]pyrazol-3-yl)-3-(8-methyl-2-phenylimidazo[1,2-a]pyridin-3-yl)urea Prepared according to the procedure of Example 10, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (5,5-dioxido-2-phenyl-4,6-dihydro-2H-thieno[3,4-c]pyrazol-3-yl)carbamate [Intermediate 21] to afford the title compound (24 mg, 40% yield) as a white solid. MS (apci) m/z=499.1 (M+H).

Example 18

1-(5,5-dioxido-2-phenyl-4,6-dihydro-2H-thieno[3,4-c]pyrazol-3-yl)-3-(2-phenyl-8-(trifluoromethyl)imidazo[1,2-a]pyridin-3-yl)urea Prepared according to the procedure of Example 17, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] to afford the title compound (9 mg, 13% yield) as a white solid. MS (apci) m/z=553.1 (M+H).

Example 19

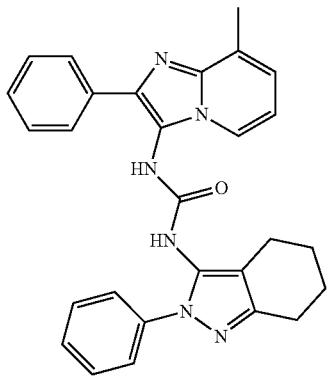 [SMILES: Cc1cccn2c(NC(=O)Nc3c4c(nn3-c3ccccc3)CCCC4)c(-c3ccccc3)nc12]

1-(8-methyl-2-phenylimidazo[1,2-a]pyridin-3-yl)-3-(2-phenyl-4,5,6,7-tetrahydro-2H-indazol-3-yl)urea Prepared according to the procedure of Example 10, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (2-phenyl-4,5,6,7-tetrahydro-2H-indazol-3-yl)carbamate [Intermediate 18] to afford the title compound (50 mg, 80% yield) as a white solid. MS (apci) m/z=463.2 (M+H).

Example 20

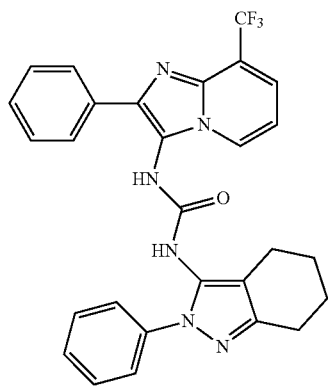 [SMILES: O=C(Nc1c2c(nn1-c1ccccc1)CCCC2)Nc1c(-c2ccccc2)nc2c(C(F)(F)F)cccn12]

1-(2-phenyl-4,5,6,7-tetrahydro-2H-indazol-3-yl)-3-(2-phenyl-8-(trifluoromethyl)imidazo[1,2-a]pyridin-3-yl)urea Prepared according to the procedure of Example 19, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] to afford the title compound (51 mg, 73% yield) as a pale yellow solid. MS (apci) m/z=517.2 (M+H).

Example 21

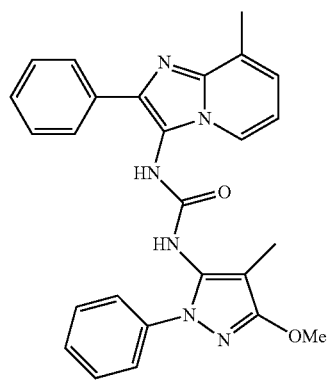 [SMILES: COc1nn(-c2ccccc2)c(NC(=O)Nc2c(-c3ccccc3)nc3c(C)cccn23)c1C]

1-(3-methoxy-4-methyl-1-phenyl-1H-pyrazol-5-yl)-3-(8-methyl-2-phenylimidazo[1,2-a]pyridin-3-yl)urea Prepared according to the procedure of Example 10, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (3-methoxy-4-methyl-1-phenyl-1H-pyrazol-5-yl)carbamate [Intermediate 9] to afford the title compound (34 mg, 53% yield) as a white solid. MS (apci) m/z=453.2 (M+H).

Example 22

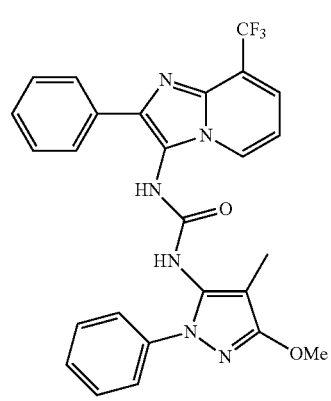 [SMILES: COc1nn(-c2ccccc2)c(NC(=O)Nc2c(-c3ccccc3)nc3c(C(F)(F)F)cccn23)c1C]

1-(3-methoxy-4-methyl-1-phenyl-1H-pyrazol-5-yl)-3-(2-phenyl-8-(trifluoromethyl)imidazo[1,2-a]pyridin-3-yl)urea Prepared according to the procedure of Example 21, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] to afford the title compound (35 mg, 49% yield) as a pale yellow solid. MS (apci) m/z=507.2 (M+H).

Example 23

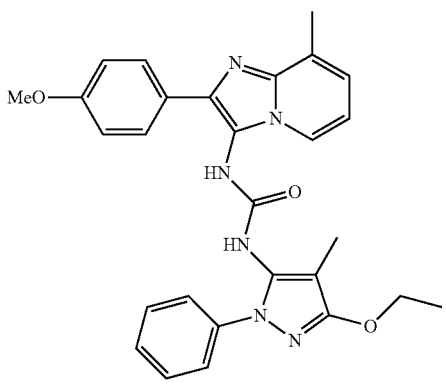 [SMILES: CCOc1nn(-c2ccccc2)c(NC(=O)Nc2c(-c3ccc(OC)cc3)nc3c(C)cccn23)c1C]

1-(3-ethoxy-4-methyl-1-phenyl-1H-pyrazol-5-yl)-3-(2-(4-methoxyphenyl)-8-methylimidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-(4-methoxyphenyl)-8-methylimidazo[1,2-a]pyridin-3-amine dihydrochloride [Preparation A10] to afford the title compound (16 mg, 24% yield) as a cream solid. MS (apci) m/z=497.2 (M+H).

Example 24

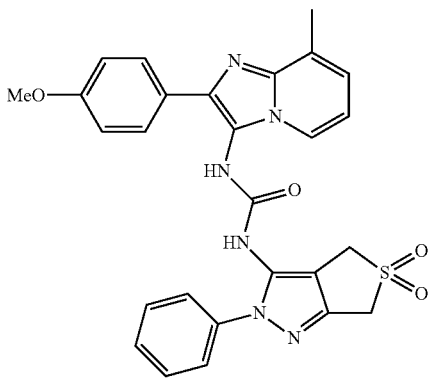 [SMILES: COc1ccc(-c2nc3c(C)cccn3c2NC(=O)Nc2c3c(nn2-c2ccccc2)CS(=O)(=O)C3)cc1]

1-(5,5-dioxido-2-phenyl-4,6-dihydro-2H-thieno[3,4-c]pyrazol-3-yl)-3-(2-(4-methoxyphenyl)-8-methyl-imidazo[1,2-a]pyridin-3-yl)urea Prepared according to the procedure of Example 23, substituting phenyl (3-ethoxy-4-methyl-1-phenyl-1H-pyrazol-5-yl)carbamate [Intermediate 8] with phenyl (5,5-dioxido-2-phenyl-4,6-dihydro-2H-thieno[3,4-c]pyrazol-3-yl) carbamate [Intermediate 21] to afford the title compound (31 mg, 47% yield) as a white powder. MS (apci) m/z=529.2 (M+H).

Example 25

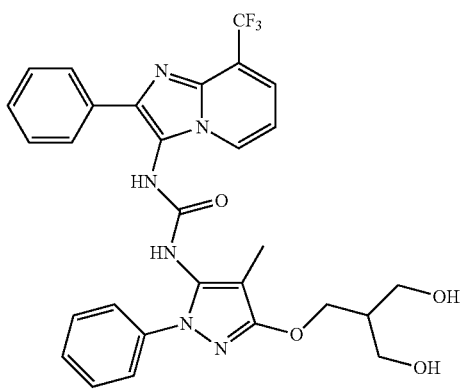 [SMILES: Cc1c(OCC(CO)CO)nn(-c2ccccc2)c1NC(=O)Nc1c(-c2ccccc2)nc2c(C(F)(F)F)cccn12]

1-(3-(3-hydroxy-2-(hydroxymethyl)propoxy)-4-methyl-1-phenyl-1H-pyrazol-5-yl)-3-(2-phenyl-8-(trifluoromethyl)imidazo[1,2-a]pyridin-3-yl)urea Step A: Preparation of (2,2-dimethyl-1,3-dioxan-5-yl)methanol: To a suspension of 2-(hydroxymethyl)propane-1,3-diol (5.0 g, 47.1 mmol) in THF (100 mL) was added pTsOH (269 mg, 1.41 mmol) followed by 2,2-dimethoxypropane (6.72 mL, 54.7 mmol). The solution was stirred for 3 hours at ambient temperature then treated with pTsOH (200 mg) and stirred at ambient temperature for 48 hours. Triethylamine (3 mL) was added and the mixture concentrated under vacuum. The residue was purified silica column chromatography eluting with 5% MeOH/DCM to afford (2,2-dimethyl-1,3-dioxan-5-yl)methanol (5.04 g, 73% yield) as a colorless liquid. $^1$H NMR (CDCl$_3$) δ 4.02 (dd, J=12.0, 4.1 Hz, 2H), 3.74-3.80 (m, 4H), 1.90 (t, J=5.1 Hz, 1H), 1.78-1.88 (m, 1H), 1.45 (s, 3H), 1.40 (s, 3H) ppm.

Step B: Preparation of (2,2-dimethyl-1,3-dioxan-5-yl) methyl methanesulfonate: To a solution of (2,2-dimethyl-1,3-dioxan-5-yl)methanol (1.0 g, 6.84 mmol) in DCM (30 mL) at 0° C. was added triethylamine (1.43 mL, 10.3 mmol) followed by mesyl chloride (0.58 mL, 7.52 mmol). The mixture was allowed to warm slowly to ambient temperature over 16 hours then partitioned between 0.5 M HCl (40 mL) and DCM (20 mL). The aqueous layer was extracted with DCM (2×20 mL) and the combined organic phases were washed with brine (20 mL), dried over Na$_2$SO$_4$, filtered and concentrated (2,2-dimethyl-1,3-dioxan-5-yl)methyl methanesulfonate (1.29 g, 84% yield) as a colorless oil. $^1$H NMR (CDCl$_3$) δ 4.41 (d, J=7.3 Hz, 2H), 4.08 (dd, J=12.5, 3.6 Hz, 2H), 3.77 (dd, J=12.5, 3.9 Hz, 2H), 3.04 (s, 3H), 2.03-1.98 (m, 1H), 1.46 (s, 3H), 1.39 (s, 3H) ppm.

Step C: Preparation of 3-(2,2-dimethyl-1,3-dioxan-5-yl) methoxy)-4-methyl-1-phenyl-1H-pyrazol-5-amine: To a solution of 5-amino-4-methyl-1-phenyl-1H-pyrazol-3(2H)-one [Intermediate 1, Step A] (500 mg, 2.64 mmol) in DMF (5 mL) was added K$_2$CO$_3$ (1.10 g, 7.93 mmol) followed by a solution of (2,2-dimethyl-1,3-dioxan-5-yl)methyl methanesulfonate (711 mg, 3.17 mmol). The mixture was warmed to 50° C. and stirred for 16 hours then and treated with water (30 mL). The aqueous was extracted with EtOAc (3×20 mL) and the combined organic phases were washed with water (5×10 mL) and brine (10 mL) then dried over Na$_2$SO$_4$, filtered and concentrated under vacuum. The residue was purified by silica column chromatography eluting with 4:1 to 2:1 hexanes/EtOAc to afford 3-((2,2-dimethyl-1,3-dioxan-5-yl)methoxy)-4-methyl-1-phenyl-1H-pyrazol-5-amine (198 mg, 24% yield) as a yellow gum. MS (apci) m/z=318.1 (M+H).

Step D: Preparation of phenyl (3-(3-hydroxy-2-(hydroxymethyl)propoxy)-4-methyl-1-phenyl-1H-pyrazol-5-yl)carbamate: To a solution of 3-((2,2-dimethyl-1,3-dioxan-5-yl)methoxy)-4-methyl-1-phenyl-1H-pyrazol-5-amine (198 mg, 0.62 mmol) in EtOAc (5 mL) was added 2M NaOH (780 μL, 1.56 mmol) followed by phenyl chloroformate (117 μL, 0.94 mmol). The mixture was stirred at ambient temperature for 16 hours then partitioned between water (20 mL) and EtOAc (20 mL). The aqueous layer was extracted with EtOAc (2×20 mL) and the combined organic phases were washed with saturated NaHCO$_3$ (20 mL) and brine (20 mL) then dried over Na$_2$SO$_4$, filtered and concentrated under vacuum. The residue was purified by silica column chromatography eluting with 2-4% MeOH/DCM to afford phenyl (3-(3-hydroxy-2-(hydroxymethyl)propoxy)-4-methyl-1-phenyl-1H-pyrazol-5-yl)carbamate (75 mg, 30% yield) as a cream foam. MS (apci) m/z=398.2 (M+H).

Step E: Preparation of 1-(3-(3-hydroxy-2-(hydroxymethyl)propoxy)-4-methyl-1-phenyl-1H-pyrazol-5-yl)-3-(2-phenyl-8-(trifluoromethyl)imidazo[1,2-a]pyridin-3-yl)urea: To a suspension of phenyl-8-(trifluoromethyl)imidazo[1,2-a]pyridin-3-amine hydrochloride [Preparation A5] (27 mg, 0.08 mmol) and phenyl (3-(3-hydroxy-2-(hydroxymethyl) propoxy)-4-methyl-1-phenyl-1H-pyrazol-5-yl)carbamate (37 mg, 0.09 mmol) in DMA (1 mL) was added DIEA (44 μL, 0.25 mmol). The solution was stirred at ambient temperature for 16 hours then partitioned between saturated NH$_4$Cl (20 mL) and EtOAc (20 mL). The aqueous layer extracted with EtOAc (2×10 mL) and the combined organic phases were washed with water (4×10 mL) and brine (10 mL) then dried over Na$_2$SO$_4$, filtered and concentrated under vacuum. The residue was triturated with DCM, filtered and dried to afford the title compound (19 mg, 34% yield) as a light yellow powder. MS (apci) m/z=581.2 (M+H).

Example 26

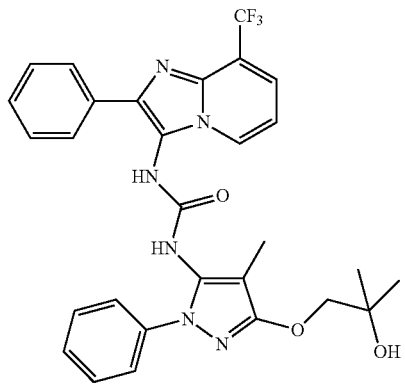 [SMILES: Cc1c(OCC(C)(C)O)nn(-c2ccccc2)c1NC(=O)Nc1c(-c2ccccc2)nc2c(C(F)(F)F)cccn12]

1-(3-(2-hydroxy-2-methylpropoxy)-4-methyl-1-phenyl-1H-pyrazol-5-yl)-3-(2-phenyl-8-(trifluoromethyl)imidazo[1,2-a]pyridin-3-yl)urea Prepared according to the procedure of Example 21, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] and phenyl (3-methoxy-4-methyl-1-phenyl-1H-pyrazol-5-yl)carbamate [Intermediate 9] with phenyl (3-(2-hydroxy-2-methylpropoxy)-4-methyl-1-phenyl-1H-pyrazol-5-yl)carbamate [Intermediate 11] to afford the title compound (37 mg, 41% yield) as a pale yellow solid. MS (apci) m/z=565.2 (M+H).

Example 27

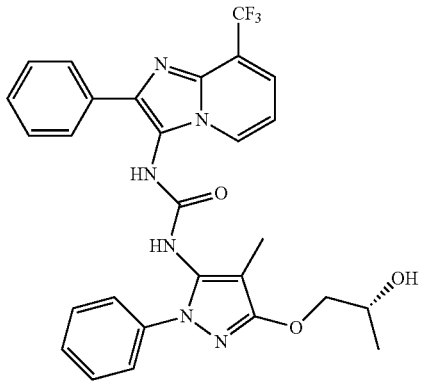 [SMILES: Cc1c(OC[C@@H](C)O)nn(-c2ccccc2)c1NC(=O)Nc1c(-c2ccccc2)nc2c(C(F)(F)F)cccn12]

(R)-1-(3-(2-hydroxypropoxy)-4-methyl-1-phenyl-1H-pyrazol-5-yl)-3-(2-phenyl-8-(trifluoromethyl)imidazo[1,2-a]pyridin-3-yl)urea Prepared according to the procedure of Example 21, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] and phenyl (3-methoxy-4-methyl-1-phenyl-1H-pyrazol-5-yl)carbamate [Intermediate 9] with (R)-phenyl (3-(2-hydroxypropoxy)-4-methyl-1-phenyl-1H-pyrazol-5-yl)carbamate [Intermediate 30] to afford the title compound (25 mg, 48% yield) as a pale yellow solid. MS (apci) m/z=551.2 (M+H).

Example 28

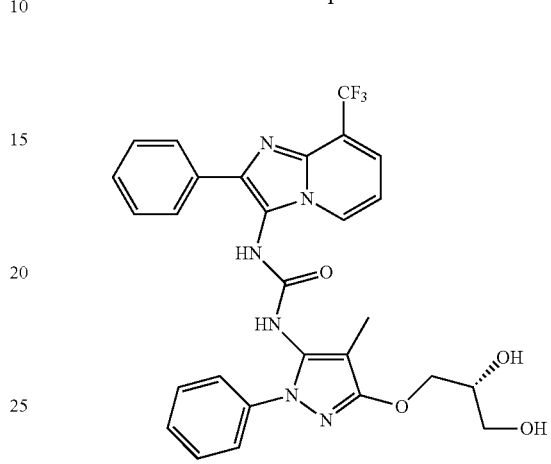

(R)-1-(3-(2,3-dihydroxypropoxy)-4-methyl-1-phenyl-1H-pyrazol-5-yl)-3-(2-phenyl-8-(trifluoromethyl)imidazo[1,2-a]pyridin-3-yl)urea Prepared according to the procedure of Example 10, substituting 8-methyl-2-phenylimidazo[1,2-a]pyridin-3-amine dihydrochloride [Preparation A3] with 2-phenyl-8-(trifluoromethyl)imidazo[1,2-a]pyridin-3-amine hydrochloride [Preparation A5] to afford the title compound (31 mg, 35% yield) as a cream powder. MS (apci) m/z=567.2 (M+H).

Example 29

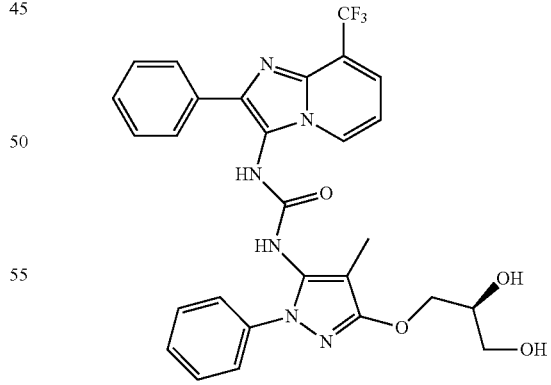

(S)-1-(3-(2,3-dihydroxypropoxy)-4-methyl-1-phenyl-1H-pyrazol-5-yl)-3-(2-phenyl-8-(trifluoromethyl)imidazo[1,2-a]pyridin-3-yl)urea Prepared according to the procedure of Example 28, substituting (S)-phenyl 3-((2,2-dimethyl-1,3-dioxolan-4-yl)

methoxy)-4-methyl-1-phenyl-1H-pyrazol-5-yl carbamate [Intermediate 10] with (R)-phenyl 3-((2,2-dimethyl-1,3-dioxolan-4-yl)methoxy)-4-methyl-1-phenyl-1H-pyrazol-5-yl carbamate [Intermediate 14] to afford the title compound (32 mg, 52% yield) as a pale yellow powder. MS (apci) m/z=567.2 (M+H).

Example 30

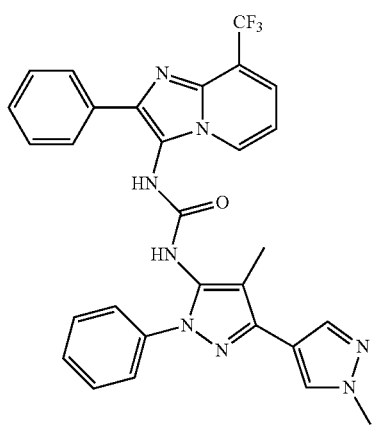 [SMILES: Cc1c(-c2cnn(C)c2)nn(-c2ccccc2)c1NC(=O)Nc1c(-c2ccccc2)nc2c(C(F)(F)F)cccn12]

1-(1',4-dimethyl-1-phenyl-1H,1'H-[3,4'-bipyrazol]-5-yl)-3-(2-phenyl-8-(trifluoromethyl)imidazo[1,2-a]pyridin-3-yl)urea Prepared according to the procedure of Example 28, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (1',4-dimethyl-1-phenyl-1H,1'H-[3,4'-bipyrazol]-5-yl)carbamate [Intermediate 25] to afford the title compound (33 mg, 37% yield) as a pale yellow powder. MS (apci) m/z=557.2 (M+H).

Example 31

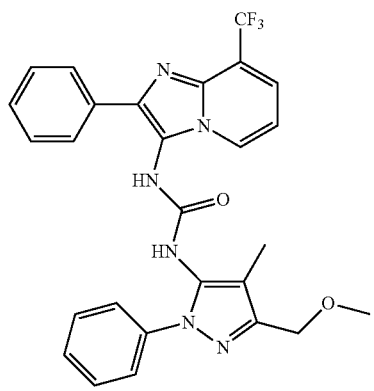 [SMILES: COCc1nn(-c2ccccc2)c(NC(=O)Nc2c(-c3ccccc3)nc3c(C(F)(F)F)cccn23)c1C]

1-(3-(methoxymethyl)-4-methyl-1-phenyl-1H-pyrazol-5-yl)-3-(2-phenyl-8-(trifluoromethyl)imidazo[1,2-a]pyridin-3-yl)urea Prepared according to the procedure of Example 28, substituting (S)-phenyl 3-((2,2-dimethyl-1,3-dioxolan-4-yl)methoxy)-4-methyl-1-phenyl-1H-pyrazol-5-yl carbamate [Intermediate 10] with phenyl (3-(methoxymethyl)-4-methyl-1-phenyl-1H-pyrazol-5-yl)carbamate [Intermediate 23] to afford the title compound (34 mg, 51% yield) as a pale yellow solid. MS (apci) m/z=521.2 (M+H).

Example 32

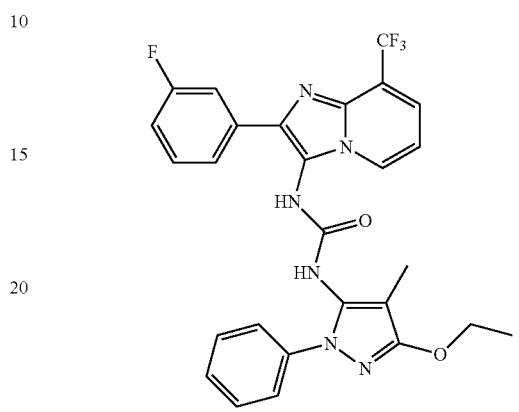

1-(3-ethoxy-4-methyl-1-phenyl-1H-pyrazol-5-yl)-3-(2-(3-fluorophenyl)-8-(trifluoromethyl)imidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-(3-fluorophenyl)-8-(trifluoromethyl)imidazo[1,2-a]pyridin-3-amine hydrochloride [Preparation A8] to afford the title compound (37 mg, 32% yield) as a beige solid. MS (apci) m/z=539.2 (M+H).

Example 33

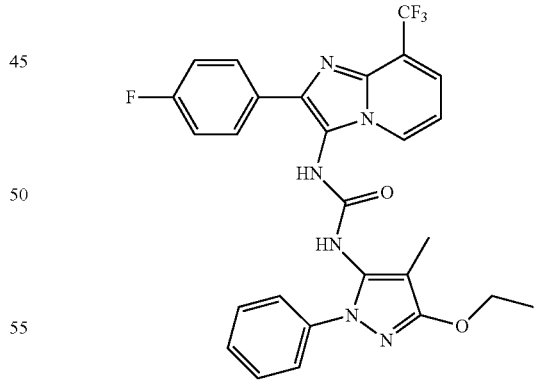

1-(3-ethoxy-4-methyl-1-phenyl-1H-pyrazol-5-yl)-3-(2-(4-fluorophenyl)-8-(trifluoromethyl)imidazo[1,2-a]pyridin-3-yl)urea Prepared according to the procedure of Example 2, substituting 8-methyl-2-phenylimidazo[1,2-a]pyrazin-3-amine dihydrochloride [Preparation A1] with 2-(4-fluorophenyl)-8-(trifluoromethyl)imidazo[1,2-a]pyridin-3-amine hydrochloride [Preparation A9] to afford the title compound (46 mg, 56% yield) as a cream solid. MS (apci) m/z=539.2 (M+H).

Example 34

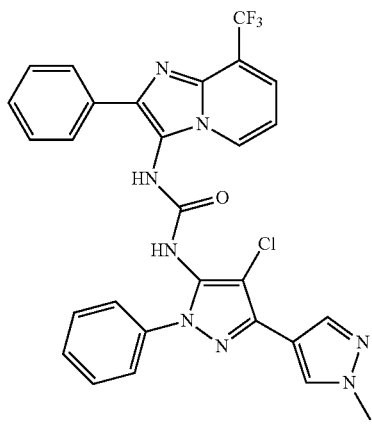 [SMILES: Cn1cc(-c2nn(-c3ccccc3)c(NC(=O)Nc3c(-c4ccccc4)nc4c(C(F)(F)F)cccn34)c2Cl)cn1]

1-(4-chloro-1'-methyl-1-phenyl-1H,1'H-[3,4'-bipyrazol]-5-yl)-3-(2-phenyl-8-(trifluoromethyl)imidazo[1,2-a]pyridin-3-yl)urea To a solution of phenyl (1'-methyl-1-phenyl-1H,1'H-[3,4'-bipyrazol]-5-yl)carbamate [Intermediate 25] (50 mg, 0.14 mmol) in DCM (2 mL) was added NCS (20 mg, 0.15 mmol) followed by PPTS (3.5 mg, 0.01 mmol). The solution was stirred at ambient temperature for 48 hours then treated with 2-phenyl-8-(trifluoromethyl)imidazo[1,2-a]pyridin-3-amine hydrochloride [Preparation A5] (44 mg, 0.14 mmol) followed by DIEA (121 µL, 0.7 mmol). After stirring for a further 24 hours the mixture was partitioned between DCM (10 mL) and saturated NaHCO₃ (10 mL) and the aqueous layer extracted with DCM (2×10 mL). The combined organic phases were washed with brine (10 mL), dried over Na₂SO₄, filtered and concentrated under vacuum. The residue was purified by silica column chromatography eluting with 2% MeOH/DCM to afford the title compound (7 mg, 9% yield) as a beige solid. MS (apci) m/z=577.2 (M+H).

Example 35

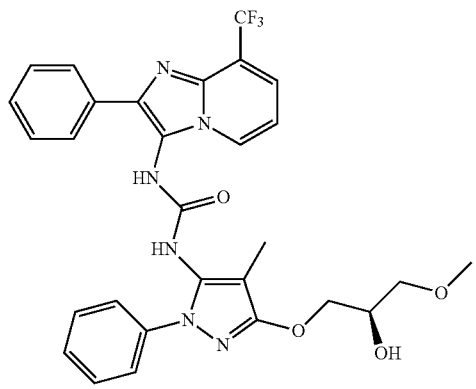 [SMILES: COC[C@@H](O)COc1nn(-c2ccccc2)c(NC(=O)Nc2c(-c3ccccc3)nc3c(C(F)(F)F)cccn23)c1C]

(R)-1-(3-(2-hydroxy-3-methoxypropoxy)-4-methyl-1-phenyl-1H-pyrazol-5-yl)-3-(2-phenyl-8-(trifluoromethyl)imidazo[1,2-a]pyridin-3-yl)urea Step A: Preparation of (R)-phenyl (3-(2-((tert-butyldimethylsilyl)oxy)-3-methoxypropoxy)-4-methyl-1-phenyl-1H-pyrazol-5-yl)carbamate: A solution of (R)-3-(2-(tert-butyldimethylsilyloxy)-3-methoxypropoxy)-4-methyl-1-phenyl-1H-pyrazol-5-amine [Intermediate 27] (0.910 g, 2.32 mmol) in EtOAc (12 mL) was cooled to 0° C. NaOH (2.90 mL, 2M, 5.81 mmol) and phenylchloroformate (0.437 mL, 3.49 mmol) were added sequentially and the mixture was stirred for 5 minutes. The mixture was allowed to reach ambient temperature and stirred for 18 hours. The mixture was diluted with hexanes (12 mL) and washed with H₂O (2×), saturated NaCl and dried over MgSO₄/activated carbon. Solution eluted through a SiO₂ plug (60 mL c-frit, 1/2 full of SiO₂, MgSO₄ cap layer) eluting with 50% EtOAc-hexanes. Filtrate was concentrated and the residue suspended in hexanes and stirred vigorously for 30 minutes. Solid collected, washed with hexanes and dried under vacuum to afford (R)-phenyl (3-(2-((tert-butyldimethylsilyl)oxy)-3-methoxypropoxy)-4-methyl-1-phenyl-1H-pyrazol-5-yl)carbamate (869 mg, 73% yield) as a white solid. MS (apci) m/z=512.3 (M+H).

Step B: Preparation of (R)-1-(3-(2-((tert-butyldimethylsilyl)oxy)-3-methoxypropoxy) -4-methyl-1-phenyl-1H-pyrazol-5-yl)-3-(2-phenyl-8-(trifluoromethyl)imidazo[1,2-a]pyridin-3-yl)urea: To a suspension of 2-phenyl-8-(trifluoromethyl)imidazo[1,2-a]pyridin-3-amine hydrochloride (30 mg, 0.96 mmol) [Preparation A5] and (R)-phenyl (3-(2-((tert-butyldimethylsilyl)oxy)-3-methoxypropoxy)-4-methyl-1-phenyl-1H-pyrazol-5-yl)carbamate (53.4 mg, 0.10 mmol) in DMA (1 mL) was added DIEA (58 µL, 0.34 mmol). The solution was stirred at ambient temperature for 16 hours then partitioned between saturated NH₄Cl (20 mL) and EtOAc (10 mL). The aqueous layer was extracted with EtOAc (2×10 mL) and the combined organic phases were washed with water (5×10 mL) and brine (10 mL) then dried over Na₂SO₄, filtered and concentrated under vacuum. The residue was purified by silica column chromatography eluting with 2:1 hexanes/EtOAc to afford (R)-1-(3-(2-((tert-butyldimethylsilyl)oxy)-3-methoxypropoxy)-4-methyl-1-phenyl-1H-pyrazol-5-yl)-3-(2-phenyl-8-(trifluoromethyl)imidazo[1,2-a]pyridin-3-yl)urea (46 mg, 69% yield) as a bright yellow solid. MS (apci) m/z=695.3 (M+H).

Step C: Preparation of (R)-1-(3-(2-hydroxy-3-methoxypropoxy)-4-methyl-1-phenyl-1H-pyrazol-5-yl)-3-(2-phenyl-8-(trifluoromethyl)imidazo[1,2-a]pyridin-3-yl)urea: A solution of (R)-1-(3-(2-((tert-butyldimethylsilyl)oxy)-3-methoxypropoxy)-4-methyl-1-phenyl-1H-pyrazol-5-yl)-3-(2-phenyl-8-(trifluoromethyl)imidazo[1,2-a]pyridin-3-yl)urea (46 mg, 0.066 mmol) in THF (3 mL) was treated with aqueous 1M HCl (3 mL) and stirred at ambient temperature for 3 hours. The mixture was concentrated to half volume and basified to pH12 with 1N NaOH. This was extracted with EtOAc (3×10 mL) and the combined organic phases were washed with brine (10 mL), dried over Na₂SO₄, filtered and concentrated under vacuum. The residue was triturated with DCM, filtered and dried under vacuum to afford the title compound (20.5 mg, 53% yield) as a white solid. MS (apci) m/z=581.2 (M+H).

Example 36

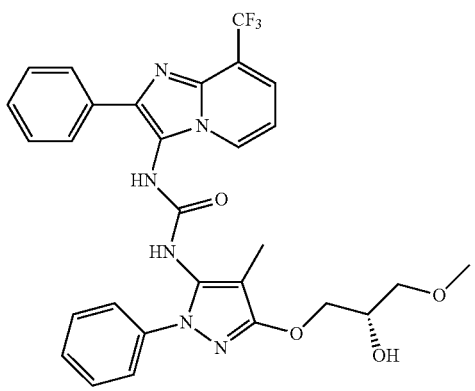 [SMILES: COC[C@H](O)COc1nn(-c2ccccc2)c(NC(=O)Nc2c(-c3ccccc3)nc3c(C(F)(F)F)cccn23)c1C]

(S)-1-(3-(2-hydroxy-3-methoxypropoxy)-4-methyl-
1-phenyl-1H-pyrazol-5-yl)-3-(2-phenyl-8-(trifluo-
romethyl)imidazo[1,2-a]pyridin-3-yl)urea Prepared according to the procedure of Example 35, substituting (R)-3-(2-(tert-butyldimethylsilyloxy)-3-methoxypropoxy)-4-methyl-1-phenyl-1H-pyrazol-5-amine [Intermediate 27] with (S)-3-(2-((tert-butyldimethylsilyl)oxy)-3-methoxypropoxy)-4-methyl-1-phenyl-1H-pyrazol-5-amine [Intermediate 26] in Step A to afford the title compound (17 mg, 44% yield) as a cream solid. MS (apci) m/z=581.2 (M+H).

Example 37

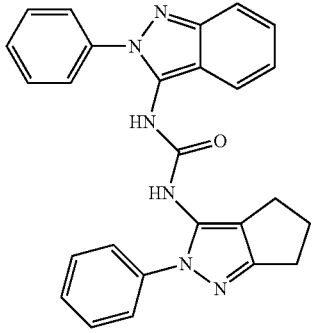 [SMILES: O=C(Nc1c2c(nn1-c1ccccc1)CCC2)Nc1c2ccccc2nn1-c1ccccc1]

1-(2-phenyl-2,4,5,6-tetrahydrocyclopenta[c]pyrazol-
3-yl)-3-(2-phenyl-2H-indazol-3-yl)urea Step A: Preparation of 1-(2-iodophenyl)-2-phenyldiazene: To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO₃ until basic. The mixture was extracted with EtOAc (3x) and the combined extracts were washed with water, saturated NaCl and dried over MgSO₄. The solution was filtered, concentrated and the residue purified by reverse phase chromatography to provide the title compound as a red solid (0.880 g, 63% yield). $^1$H NMR (CDCl$_3$) δ 7.23-7.39 (m, 3H), 7.64 (d, 1H), 7.56-7.51 (m, 3H), 7.45 (t, 1H), 7.1 (t, 1H).

Step B: Preparation of 2-(phenyldiazenyl)benzonitrile: To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with DCM. The combined filtrate and washes were concentrated to provide the title compound as red-orange solid that was dried in vacuum (0.280 g, 95% yield). $^1$H NMR (CDCl$_3$) δ 8.03-8.06 (m, 2H), 7.88 (dd, 2H), 7.71 (t, 1H), 7.54-7.58 (m, 4H).

Step C: Preparation of 2-phenyl-2H-indazol-3-amine: A mixture of 2-(phenyldiazenyl)benzonitrile (0.28 g, 1.35 mmol) and SnCl$_2$ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO₃ and extracted with DCM (2x). The combined organic layers were dried over MgSO$_4$, filtered and concentrated to provide the title compound as a light purple solid that was dried in vacuum (0.241 g, 85% yield). $^1$H NMR (CDCl$_3$) δ 7.69 (d, 2H), 7.52-7.58 (m, 3H), 7.47 (d, 2H), 7.26 (t, 1H), 6.90 (t, 1H), 4.28 (br s, 2H).

Step D: Preparation of 1-(2-phenyl-2,4,5,6-tetrahydrocyclopenta[c]pyrazol-3-yl)-3-(2-phenyl-2H-indazol-3-yl)urea: To a suspension of 2-phenyl-2H-indazol-3-amine (20 mg, 0.096 mmol) and phenyl (2-phenyl-2,4,5,6-tetrahydrocyclopenta[c]pyrazol-3-yl)carbamate [Intermediate 28] (33.6 mg, 0.105 mmol) in DMA (1 mL) was added DIEA (33 μL, 0.191 mmol). The reaction mixture was stirred at ambient temperature for 2 hours, then was diluted with saturated aqueous NH$_4$Cl (20 mL) and extracted with EtOAc (3×10 mL). The combined organic phases were washed with water (4×10 mL) and brine (10 mL) then dried over Na$_2$SO$_4$ and concentrated. The crude product was triturated in DCM, filtered and washed with DCM to afford the product as a white solid (24.4 mg, 59% yield). MS (apci) m/z=435.2 (M+H).

Example 38

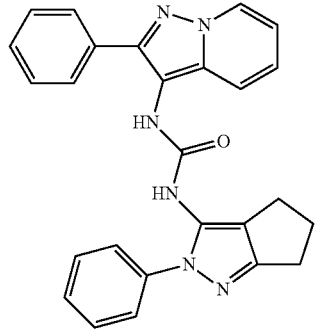 [SMILES: O=C(Nc1c(-c2ccccc2)nn2ccccc12)Nc1c2c(nn1-c1ccccc1)CCC2]

1-(2-phenyl-2,4,5,6-tetrahydrocyclopenta[c]pyrazol-
3-yl)-3-(2-phenylpyrazolo pyridin-3-yl)urea Step A: Preparation of Ethyl 2-phenylpyrazolo[1,5-a]pyridine-3-carboxylate: To a solution of 1-aminopyridinium iodide (2.22 g, 10.0 mmol) in DMF (20 mL) was added K$_2$CO$_3$ (1.93 g, 14.0 mmol) and ethyl 3-phenylpropiolate (3.30 mL, 20.0 mmol). The mixture was stirred at ambient temperature for 18 hours and was poured into chilled water (100 mL). The mixture was stirred for 30 minutes and was filtered through packed Celite®, rinsing with EtOAc and H₂O. The organic layer was removed and was washed with H₂O (4×), dried over MgSO₄, filtered and concentrated. The residual dark red-orange oil was purified by silica chromatography using a 10-50% EtOAc/hexanes gradient elution to furnish the title compound as a yellow solid (1.75 g, 65.7% yield). MS (apci) m/z=267.0 (M+H).

Step B: Preparation of 2-phenylpyrazolo[1,5-a]pyridine-3-carboxylic acid hydrochloride: To solution of ethyl 2-phenylpyrazolo[1,5-a]pyridine-3-carboxylate (1.72 g, 6.46 mmol) in EtOH (10 mL) was added 2M NaOH (16.1 mL, 32.3 mmol) and the reaction mixture was heated at reflux for 7 hours. The reaction mixture was cooled to ambient temperature and was cooled in an ice bath. The mixture was acidified with concentrated HCl and the resulting suspension was collected by vacuum filtration. The product cake was washed with water and dried in vacuum to afford the title compound as a gold solid (1.69 g, 95.2% yield). MS (apci) m/z=195.2 ((M+H)—CO₂).

Step C: Preparation of 2-phenylpyrazolo[1,5-a]pyridine: A mixture of 2-phenylpyrazolo[1,5-a]pyridine-3-carboxylic acid hydrochloride (1.00 g, 3.64 mmol) in polyphosphoric acid (41.6 m, 364 mmol) was heated at 80° C. for 17 hours. The resulting gelatinous mixture was cooled to ambient temperature and ice water was added (150 mL). The mixture was stirred until a granular suspension began to form. The suspension was transferred to water (350 mL) and the mixture stirred until a fine granular suspension resulted. The solid was collected by vacuum filtration, washed with water and dried in vacuum to afford the title compound as an orange solid (0.84 g, 118%) that was used directly in the next step. MS (apci) m/z=195.2 (M+H).

Step D: Preparation of 3-nitroso-2-phenylpyrazolo[1,5-a]pyridine: To a solution of 2-phenylpyrazolo[1,5-a]pyridine (0.84 g, 2.85 mmol) in acetic acid (2.85 mL, 51.4 mmol) was added NaNO₂ (0.295 g, 4.28 mmol) in water (1.43 mL) dropwise over 10 minutes (vigorous bubbling observed). The mixture was stirred for 20 minutes and was quenched with ice. The resulting suspension was warmed to ambient temperature and the solid collected by vacuum filtration. The collected solid was washed with water and dried in vacuum to provide the title compound as a dark green solid (0.380 g, 59.6%). MS (apci) m/z=224.1 (M+H).

Step E: Preparation of 2-phenylpyrazolo[1,5-a]pyridin-3-amine: To a mixture of 3-nitroso-2-phenylpyrazolo[1,5-a]pyridine (0.380 g, 1.70 mmol) and Zn dust (0.557 g, 8.51 mmol) in EtOH (3.81 mL) was added concentrated HCl (0.156 mL, 1.87 mmol). The mixture was heated at reflux for 3 hours and was cooled to ambient temperature. The mixture was diluted with MeOH, filtered and the Zn cake washed with MeOH. The combined filtrate and washes were concentrated and the residue was partitioned into water and DCM. The organic layer was removed and the aqueous portion was treated with saturated NaHCO₃ to achieve pH=10. The mixture was extracted with DCM (3×) and the combined extracts were washed with saturated NaCl, dried over MgSO₄, filtered and concentrated. The residue was dried in vacuum to furnish the title compound as brown solid (0.304 g, 85.5% yield). MS (apci) m/z=210.1 (M+H). ¹H NMR (CDCl₃) δ 8.31 (d, 1H), 7.91 (d, 2H), 7.49 (t, 2H), 7.38 (t, 2H), 6.96 (dd, 1H), 6.64 (t, 1H), 3.21 (br s, 2H).

Step F: Preparation of 1-(2-phenyl-2,4,5,6-tetrahydrocyclopenta[c]pyrazol-3-yl)-3-(2-phenyl-2H-indazol-3-yl)urea: To a suspension of 2-phenylpyrazolo[1,5-a]pyridin-3-amine (20 mg, 0.0956 mmol) and phenyl (2-phenyl-2,4,5,6-tetrahydrocyclopenta[c]pyrazol-3-yl)carbamate [Intermediate 28] (33.6 mg, 0.105 mmol) in DMA (1 mL) was added DIEA (17 µL, 0.096 mmol). The reaction mixture was stirred at ambient temperature for 1 hour, then was diluted with saturated aqueous NH₄Cl (20 mL) and extracted with EtOAc (3×10 mL). The combined organic phases were washed with water (4×10 mL) and brine (10 mL) then dried over MgSO₄, filtered and concentrated. The crude product was triturated in DCM, filtered and washed with DCM to afford the product as a green-brown solid (19.8 mg, 48% yield). MS (apci) m/z=435.2 (M+H).

Example 39

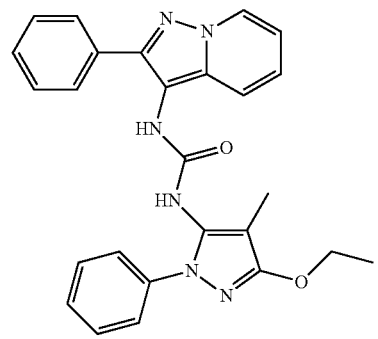 [SMILES: CCOc1nn(-c2ccccc2)c(NC(=O)Nc2c(-c3ccccc3)nn3ccccc23)c1C]

1-(3-ethoxy-4-methyl-1-phenyl-1H-pyrazol-5-yl)-3-(2-phenylpyrazolo[1,5-a]pyridin-3-yl)urea Prepared according to the procedure of Example 38, replacing phenyl (2-phenyl-2,4,5,6-tetrahydrocyclopenta[c]pyrazol-3-yl)carbamate [Intermediate 28] with phenyl (3-ethoxy-4-methyl-1-phenyl-1H-pyrazol-5-yl)carbamate [Intermediate 8] (35.5 mg, 0.105 mmol) in Step F. The reaction mixture was stirred at ambient temperature for 17 hours, then filtered and washed with DCM to afford the product as a white solid (21.8 mg, 50% yield). MS (apci) m/z=453.2 (M+H).

What is claimed is:

1. A compound of Formula I:

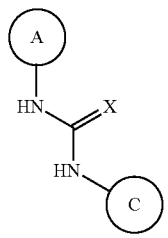

or stereoisomers, tautomers, or pharmaceutically acceptable salts, or solvates, wherein:
X is O;
Ring A is formula A-1, A-2, or A-4

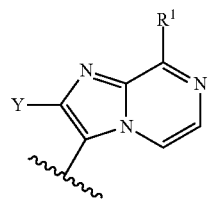
A-1

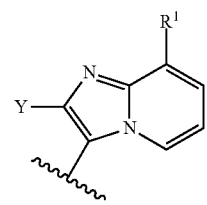
A-2

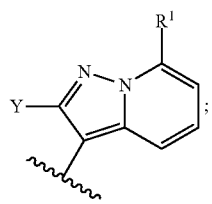
A-4 ;

R¹ is H, halogen, or (1-3C)alkyl [optionally substituted with 1-5 fluoros];
Y is Ar¹ or or hetAr¹;
Ar¹ is phenyl optionally substituted with one or more substituents independently selected from halogen and (1-3C)alkoxy [optionally substituted with 1-5 fluoros];
hetAr¹ is pyridyl optionally substituted with (1-3C)alkoxy [optionally substituted with 1-5 fluoros];
Ring C is formula C-1

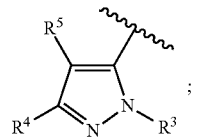
C-1 ;

R³ is Ar² ;
Ar² is phenyl;
R⁴ is (1-6C)alkyl, (1-6C)alkoxy, hydroxy(1-6C)alkoxy, dihydroxy(2-6C)alkoxy, hetAr⁴, or hydroxy(1-3C alkoxy)(1-6C)alkoxy;
hetAr⁴ is a 5-6 membered heteroaryl ring having 1-3 ring nitrogen atoms and optionally substituted with one or more substituents independently selected from (1-6C) alky
and
R⁵ is (1-6C)alkyl; or
R⁴ and R⁵ together with the atoms to which they are attached form a 5-6 membered saturated carbocyclic ring, or
R⁴ and R⁵ together with the atoms to which they are attached form 5-6 membered saturated heterocyclic ring having a ring heteroatom selected from O or S, wherein said sulfur ring atom is optionally oxidized to SO₂.

2. A compound according to claim 1, wherein:
R⁴ is (1-6C)alkyl, (1-6C)alkoxy, hydroxy(1-6C)alkoxy, dihydroxy(2-6C)alkoxy, hetAr⁴ or hydroxy(1-3C alkoxy)(1-6C)alkoxy; and
R⁵ is (1-6C)alkyl.

3. A compound according to claim 1, wherein:
R⁴ and R⁵ together with the atoms to which they are attached form a 5-6 membered saturated carbocyclic ring, or
R⁴ and R⁵ together with the atoms to which they are attached form a 5-6 membered saturated heterocyclic ring having a ring heteroatom selected from O or S, wherein said sulfur ring atom is optionally oxidized to SO₂.

4. A compound according to claim 1, selected from

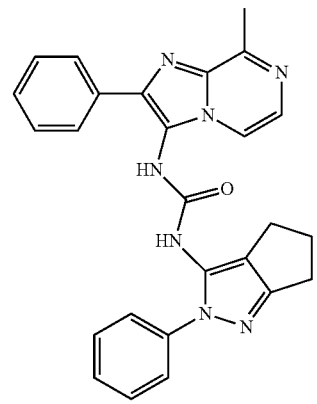

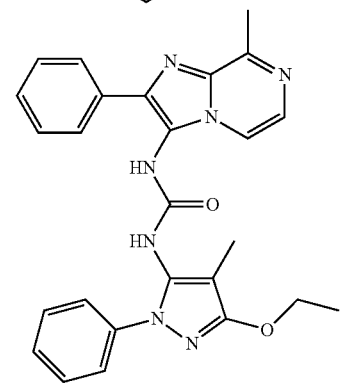

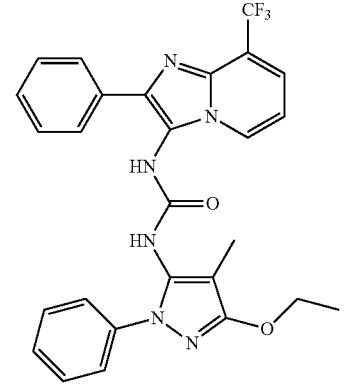

181
-continued
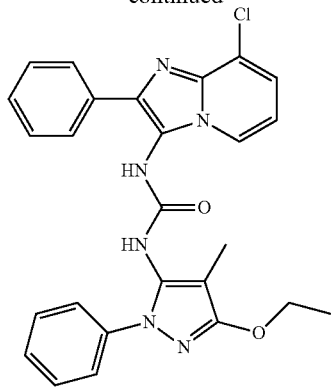
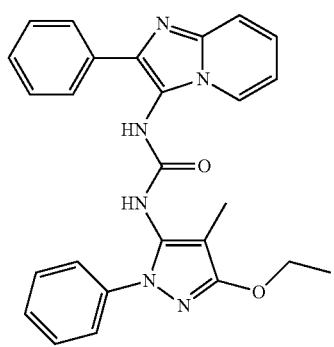
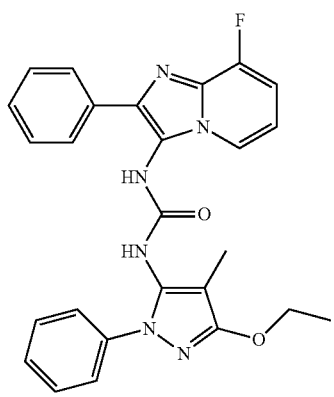
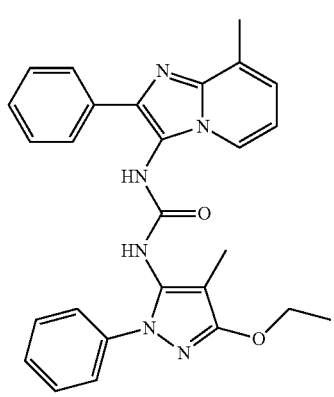
182
-continued
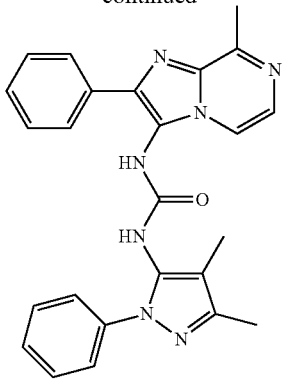
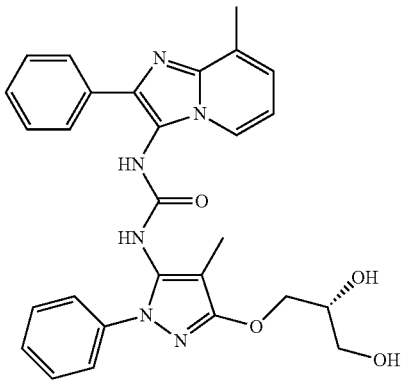
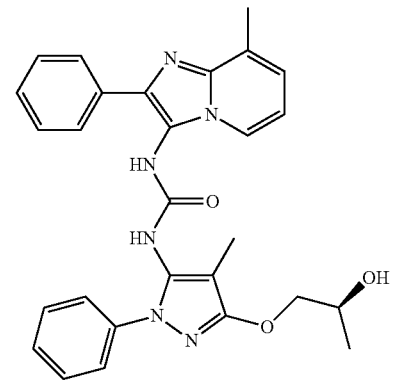
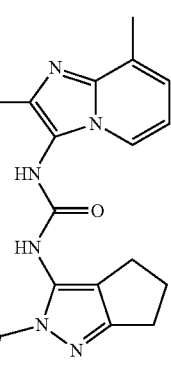

183
-continued
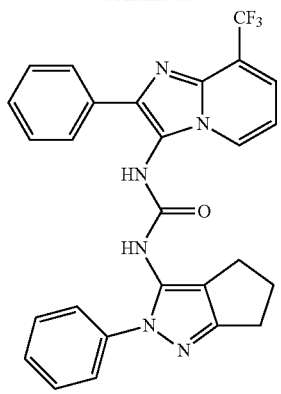
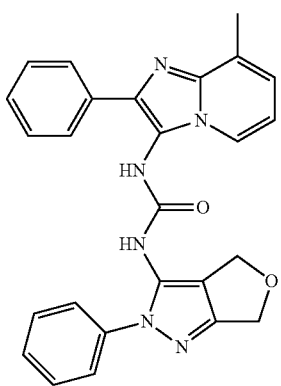
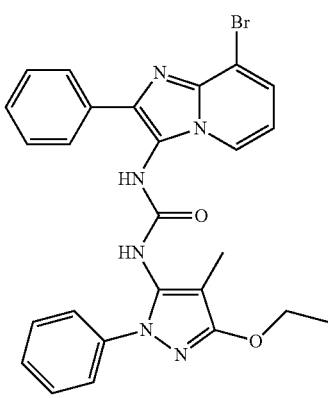
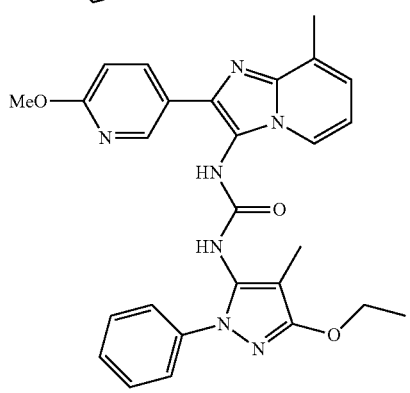
184
-continued
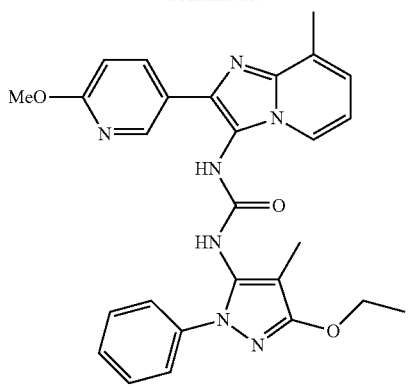
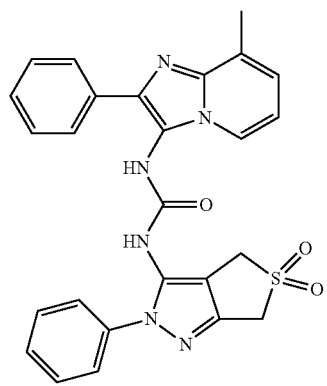
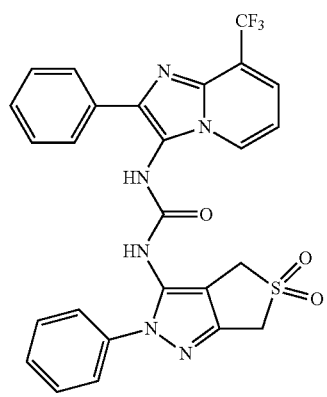
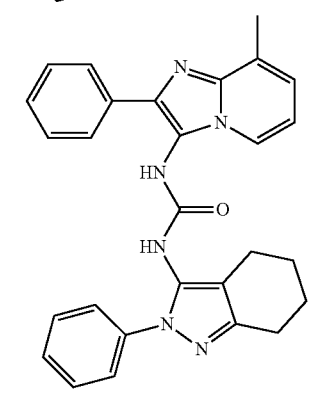

185
-continued
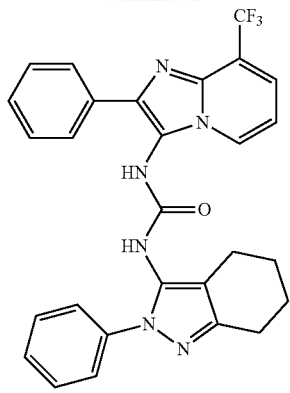
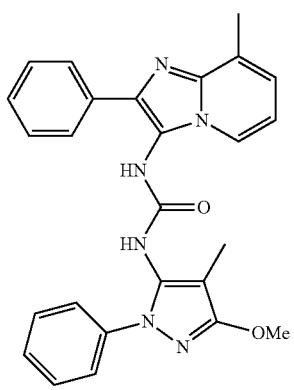
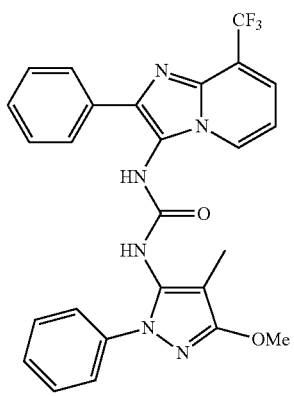
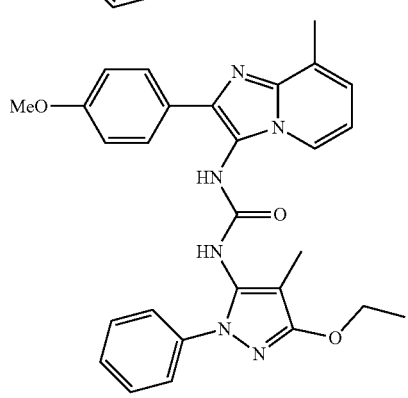
186
-continued
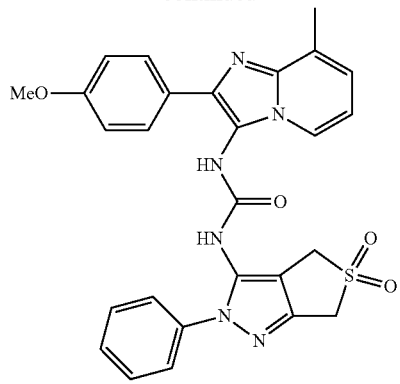
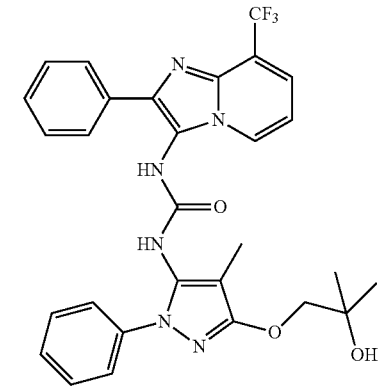
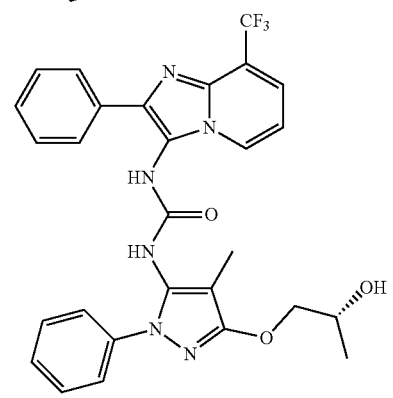

187
-continued
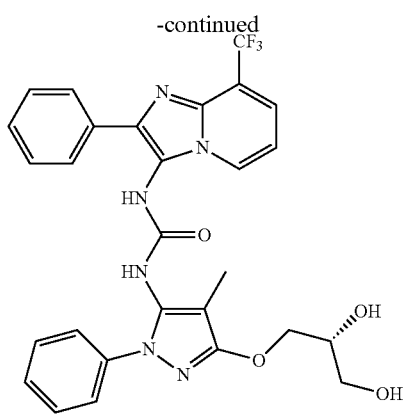
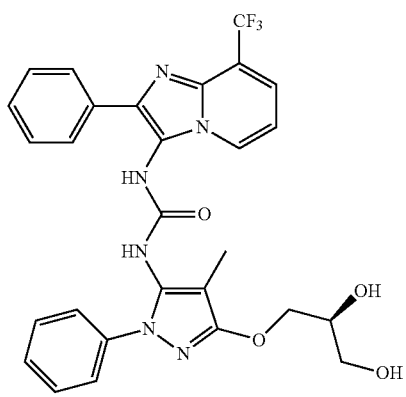
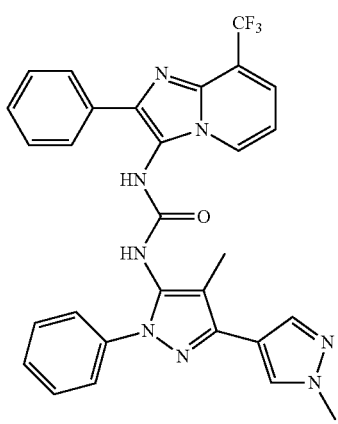
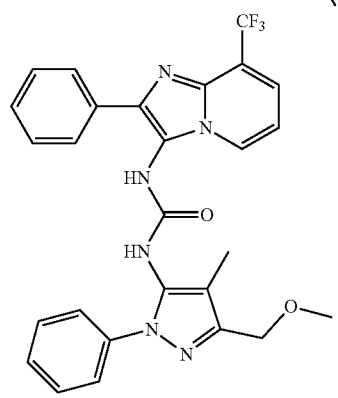
188
-continued
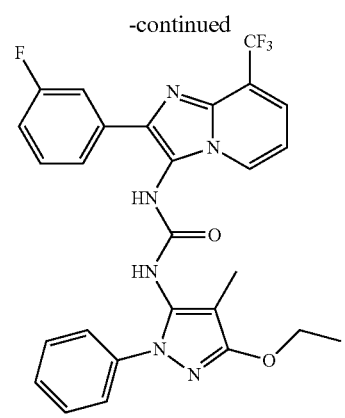
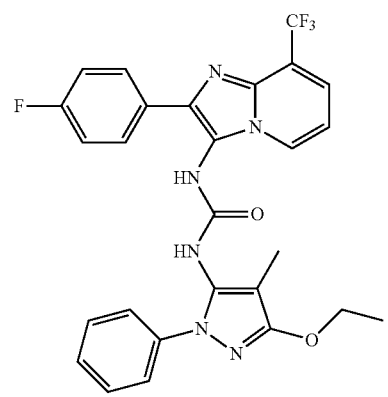
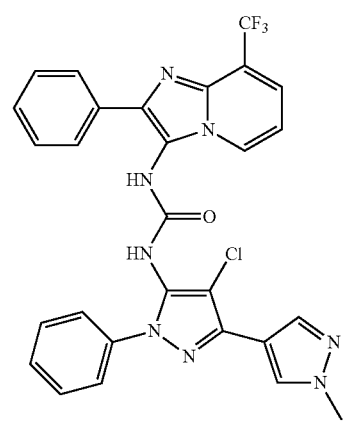
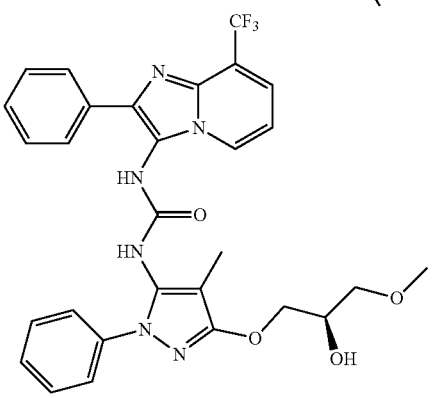

-continued

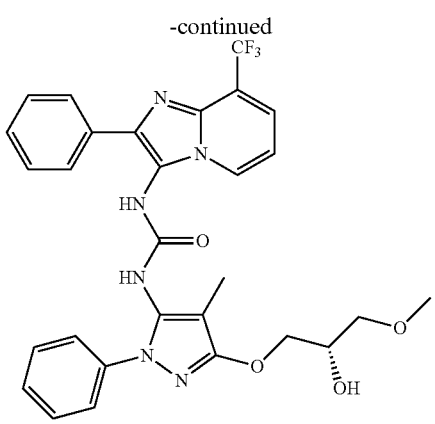

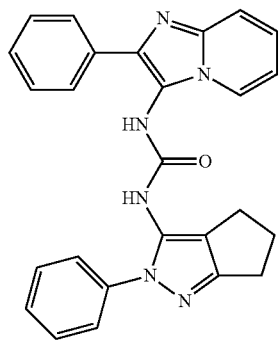

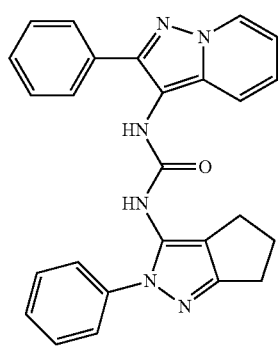

and

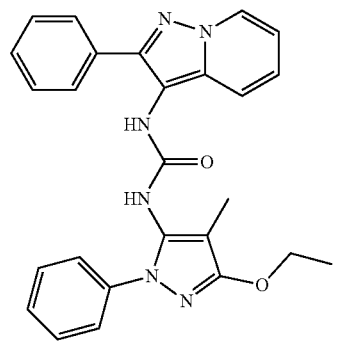

or a pharmaceutically acceptable salt thereof.

5. A pharmaceutical composition, which comprises a compound of Formula I as defined in claim 1 or a pharmaceutically acceptable salt thereof, and a pharmaceutically acceptable diluent or carrier.

6. A process for the preparation of a compound of claim 1, which comprises:

(a) coupling a corresponding compound having the formula II

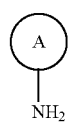
II with a corresponding compound having the formula III

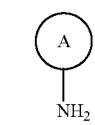
III in the presence carbonyldiimidazole or triphosgene and a base; or
or (c) coupling a corresponding compound having the formula II

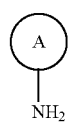
II with a corresponding compound having the formula IV

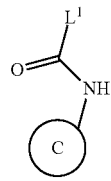
IV where $L^1$ is a leaving group, in the presence of a base; or (d) coupling a corresponding compound having the formula V

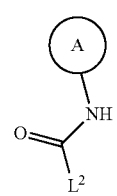
V where $L^2$ is a leaving group, with a corresponding compound having the formula III

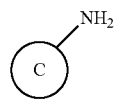　III in the presence of a base; or (e) activating a corresponding compound having the formula VI

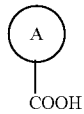　VI with diphenylphosphoryl azide followed by coupling the activated intermediate with a corresponding compound having the formula III

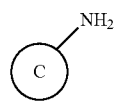　III in the presence a base; or (f) coupling a corresponding compound having the formula II

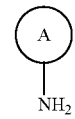　II with a corresponding compound having the formula VII

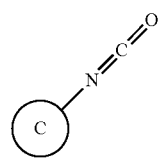　VII in the presence of a base; and optionally removing protecting groups and optionally preparing a pharmaceutically acceptable salt thereof.

* * * * *

UNITED STATES PATENT AND TRADEMARK OFFICE
CERTIFICATE OF CORRECTION

PATENT NO. : 9,822,118 B2
APPLICATION NO. : 14/442503
DATED : November 21, 2017
INVENTOR(S) : Shelley Allen et al.

Page 1 of 1

It is certified that error appears in the above-identified patent and that said Letters Patent is hereby corrected as shown below:

In the Claims

Column 179, Line 60, Claim 1, please delete "alky" and insert -- alkyl --;

Column 189, Lines 20-32, Claim 4, please delete the following structure:

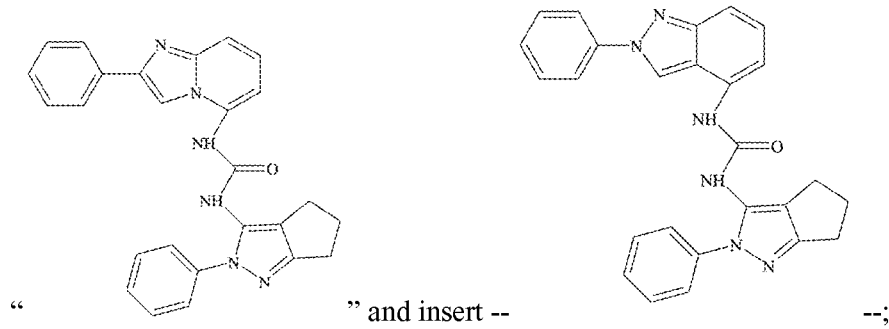

Column 190, Lines 28-29, Claim 6, please delete "base; or or" and insert -- base; or -- therefor.

Signed and Sealed this
Twenty-fourth Day of April, 2018

Andrei Iancu
*Director of the United States Patent and Trademark Office*